(12) United States Patent
Kore et al.

(10) Patent No.: US 8,211,637 B2
(45) Date of Patent: Jul. 3, 2012

(54) PROTEINASE K INHIBITORS, METHODS AND COMPOSITIONS THEREFOR

(75) Inventors: Anilkumar R. Kore, Austin, TX (US); Muthian Shanmugasundaram, Austin, TX (US)

(73) Assignee: Life Technologies Corporation, Carlsbad, CA (US)

( * ) Notice: Subject to any disclaimer, the term of this patent is extended or adjusted under 35 U.S.C. 154(b) by 334 days.

(21) Appl. No.: 12/642,322

(22) Filed: Dec. 18, 2009

(65) Prior Publication Data

US 2010/0159482 A1 Jun. 24, 2010

Related U.S. Application Data

(60) Provisional application No. 61/139,279, filed on Dec. 19, 2008.

(51) Int. Cl.
*C12Q 1/68* (2006.01)

(52) U.S. Cl. ........ 435/6.1; 435/6.12; 514/21.9; 530/330

(58) Field of Classification Search .................... 435/6.1, 435/6.12; 514/21.9; 530/330
See application file for complete search history.

(56) References Cited

U.S. PATENT DOCUMENTS

| | | | |
|---|---|---|---|
| 4,596,789 A | 6/1986 | Dutta et al. | |
| 4,691,007 A | 9/1987 | Dutta et al. | |
| 4,910,190 A | 3/1990 | Bergeson et al. | |
| 4,997,932 A | 3/1991 | Reardon et al. | |
| 5,008,245 A | 4/1991 | Digenis | |
| 5,055,450 A | 10/1991 | Edwards et al. | |
| 5,194,588 A | 3/1993 | Edwards et al. | |
| 5,284,829 A | 2/1994 | McKerrow et al. | |
| 5,364,763 A | 11/1994 | Kacian | |
| 5,414,132 A | 5/1995 | Stein et al. | |
| 5,554,516 A | 9/1996 | Kacian et al. | |
| 5,726,021 A | 3/1998 | Britschgi et al. | |
| 5,726,158 A | 3/1998 | Edwards et al. | |
| 5,871,628 A | 2/1999 | Dabiri et al. | |
| 5,871,975 A | 2/1999 | Kacian et al. | |
| 5,907,068 A | 5/1999 | Stein et al. | |
| 5,939,262 A | 8/1999 | Pasloske et al. | |
| 6,111,096 A | 8/2000 | Laugharn, Jr. et al. | |
| 6,204,375 B1 | 3/2001 | Lader | |
| 6,218,105 B1 | 4/2001 | Hall et al. | |
| 6,218,531 B1 | 4/2001 | Ekenberg | |
| 6,265,165 B1 | 7/2001 | Xu et al. | |
| 6,313,285 B1 | 11/2001 | Butler et al. | |
| 6,329,179 B1 | 12/2001 | Kopreski | |
| 6,528,641 B2 | 3/2003 | Lader | |
| 6,583,301 B1 | 6/2003 | Eaton et al. | |
| 6,664,379 B1 | 12/2003 | Kudlicki et al. | |
| 6,740,647 B1 | 5/2004 | Baucke et al. | |
| 6,825,340 B2 | 11/2004 | Pasloske et al. | |
| 7,001,724 B1 | 2/2006 | Greenfield | |
| 7,067,298 B2 | 6/2006 | Latham et al. | |
| 7,163,793 B2 | 1/2007 | Kudlicki et al. | |
| 7,214,484 B2 | 5/2007 | Weber et al. | |
| 7,964,350 B1 | 6/2011 | Fekete et al. | |
| 2001/0049133 A1 | 12/2001 | McCabe et al. | |
| 2002/0026046 A1 | 2/2002 | Pasloske et al. | |
| 2002/0172972 A1 | 11/2002 | Tabor et al. | |
| 2002/0177139 A1 | 11/2002 | Greenfield et al. | |
| 2003/0170617 A1 | 9/2003 | Pasloske | |
| 2004/0038213 A1 | 2/2004 | Kwon | |
| 2004/0115658 A1 | 6/2004 | Weber et al. | |
| 2005/0009045 A1 | 1/2005 | Greenfield et al. | |
| 2005/0014169 A1 | 1/2005 | Latham et al. | |
| 2005/0069953 A1 | 3/2005 | Fang et al. | |
| 2005/0158783 A1 | 7/2005 | Simms | |
| 2005/0277121 A1 | 12/2005 | Pasloske et al. | |
| 2006/0068480 A1 | 3/2006 | Christophers et al. | |
| 2006/0115844 A1 | 6/2006 | Finkelstein et al. | |
| 2006/0148006 A1 | 7/2006 | Fang et al. | |
| 2006/0188892 A1 | 8/2006 | Latham et al. | |
| 2006/0269536 A1 | 11/2006 | Deperthes et al. | |
| 2007/0032418 A1 | 2/2007 | Shapiro et al. | |

FOREIGN PATENT DOCUMENTS

| | | |
|---|---|---|
| EP | 0410411 | 1/1991 |
| EP | 1044984 | 10/2000 |
| EP | 1476573 | 1/2010 |
| WO | WO 93/15228 | 8/1993 |
| WO | WO 94/26867 | 11/1994 |
| WO | WO 96/00228 | 1/1996 |
| WO | WO 00/17320 | 3/2000 |
| WO | WO 01/21830 | 3/2001 |
| WO | WO 01/42507 | 6/2001 |
| WO | WO 03/002716 | 1/2003 |
| WO | WO 03/064605 | 8/2003 |
| WO | WO 2010/071833 | 6/2010 |

OTHER PUBLICATIONS

Applied Biosystems, "Testing of beta-formulation of Cells-to-cDNA III," Powerpoint presentation to GlaxoSmithKline, Aug. 3, 2006.

Applied Biosystems, "TaqMan® MicroRNA Cells-to-$C_T$™ Kit" Product Bulletin, Nov. 2007.

Baum et al., "Regulation of Expression of Cytochrome *P*-450 2D mRNA in Rat Brain with Steroid Hormones", *Brain Research*, 765, 1997, 67-73.

Betzel, C. et al. "Active-site geometry of proteinase K", *FEBS LETTERS*, vol. 197, No. 1-2, 1986, 105-110.

Dhamne, C. et al. "The chloromethylketone protease inhibitor AAPF(CMK) also targets ATP-dependent helicases and SAP-domain proteins", *Journal of Cellular Biochemistry*, vol. 100, No. 3, 2007, 716-726.

Fekete et al., Applied Biosystems "Streamlined, High-throughput Assessment of siRNA-mediated Gene Knockdown in 384-well Plates by Performing qRT-PCT from Cell Lysates" Abstract, presentation at Merck, Mar. 7, 2007.

Fink, et al., "Immunostaining and Laser-Assisted Cell Picking for mRNA Analysis," *Laboratory Investigation*, 80:3, 327-333, 2000.

(Continued)

Primary Examiner — David Lukton

(57) ABSTRACT

The synthesis, biological evaluation, and molecular modeling of alkoxysuccinyl-peptidyl-haloalkyl ketones for use as proteinase K inhibitors are described. Sample preparation processes for in situ RNA or DNA analysis using such inhibitors, methods and compositions therefor are provided.

13 Claims, 11 Drawing Sheets

OTHER PUBLICATIONS

Fink, et al., "Immunostaining for Cell Picking and Real-Time mRNA Quantitation," *American Journal of Pathology*, 157:5, 2000, 1459-1466.

Fung, et al., "PCR amplification of mRNA directly from a crude cell lystate prepared by thermophilic protease digestion," *Nucleic Acids Research*, 19:15, 4300, 1991.

GeneChoice, "cDNA Direct from Cells RT Kit" from pgcsci.com/genechoice/GeneChoice_18.html, downloaded Jan. 28, 2002.

Invitrogen CellsDirect™ One-Step qRT-PCR Kits User Manual, Aug. 16, 2006.

Invitrogen SuperScript™ III Platinum® CellsDirect Two-Step qRT-PCR Kit Instruction Manual, Nov. 12, 2004.

Ivarsson, et al., "Evaluation of the Effects of DNase Treatment on Signal Specificity in RT-PCR and in Situ RT-PCR", *BioTechniques*, 25, 630-638, 1998.

Jena, et al. "Amplification of genes, single transcripts and cDNA libraries from one cell and direct sequence analysis of amplified products derived from one molecule," *Journal of Immunological Methods*, 190, 1996, 199-213.

Jiang, et al., "A rapid RT-PCR method for detection of intact RNA in formalin-fixed paraffin-embedded tissues," *Nucleic Acids Research*, 23:15, 1995, 3071-3072.

Kher, et al., "Direct in situ reverse transcriptase-polymerase chain reaction", *Am. J. Physiol. Cell Physiol.*, 281, 2001, C726-C732.

Klebe, et al., "RT-PCR Without RNA Isolation", *BioTechniques*, 21, 1996, 1094-1100.

Kobs, "Isolation of RNA from Plant, Yeast and Bacteria", *Promega Notes*, No. 68, 1998, 28-31.

Kore, et al., "Synthesis and application of MeOSuc-Ala-Ala-Pro-Phe-CH2Cl as potent proteinase K inhibitor," *Bioorganic & Medicinal Chemistry Letters*, vol. 19, 2009, 1296-1300.

Martinez, et al., "Non-radioactive localization of nucleic acids by direct in situ PCR and in situ RT-PCR in paraffin-embedded sections," *J. Histochem. Cytochem.*, 43:8, 1995, 739-747.

Navia, et al., "Structure of human neutrophil elastase in complex with a peptide chloromethyl ketone inhibitor at 1.84-Å resolution," *Proc. Natl. Acad. Sci. USA*, vol. 86, 1989, 7-11.

New England Biolabs Catalog, 1993-1994. p. 96.

O'Brien, et al., "RT-PCR Assay for Detection of Transcripts from Very Few Cells Using Whole Cell Lysates," *BioTechniques*, 16:4, 1994, 586-590.

Peet, N. P. et al. "Synthesis of Peptidyl Fluoromethyl Ketones and Peptidyl α-Keto Esters as Inhibitors of Porcine Pancreatic Elastase, Human Neutrophil Elastase, and Rat and Human Neutrophil Cathepsin G", *Journal of Medicinal Chemistry*, vol. 33, No. 1, 1990, 394-407.

Pereira, P. J. et al. "The 2.2 Å Crystal Structure of Hhuman Chymase in Complex with Succinyl-Ala-Ala-Pro-Phe-chloromethylketone: Structural Explanation for its Dipeptidyl Carboxypeptidase Specificity", *Journal of Molecular Biology*, vol. 286. No. 1, 1999, 163-173.

Powers, J.C., "Reaction of Serine Proteases with Halomethyl Ketones," *Methods in Enzymology*, vol. 46, 1977, 197-208.

Powers, et al., "Specificity of Porcine Pancreatic Elastase, Human Leukocyte Elastase and Cathepsin G," *Biochimicia et Biosysica Acts*, vol. 485, 1977, 156-166.

Price et al., "Properties of Chromatographically Purified Bovine Pancreatic Deoxyribonuclease", *J. Biol. Chem.*, 244(4), 1969, 917-923.

Promega, "RNase-Free DNase", Feb. 2000, 1-4.

Qiagen, Qiagen FastLane Kits—from Sample Direct to Result, Jan. 2007.

Qiagen, "RNeasy Mini Handbook", Jun. 2001, 30-41.

Reilly, et al. "The degradation of human lung elastin by neutrophil proteinases", *Biochimica et Biophysica Acta*, vol. 621, 1980, 147-157.

Roche Applied Science, "Proteinase K," Version 3, Jan. 2003.

RNA Stat60™, Tel-Test Inc., Frendswood, TX, isotexdiagnostics.com/rna_stat-60_reagent.html, cited in Baum et al. 1997.

Sellner et al, "Reverse Transcriptase Inhibits Taq Polymerase Activity", Nucl. Acids. Res., 20(7), 1992, 1487-1490.

Shi, et al., "Direct reverse transcription-polymerase chain reaction from whole blood without RNA extraction," *Genetic Analysis: Biomolecular Engineering*, 9:5-6, 1992, 149-150.

Sigma-Aldrich, "Product Information: Proteinase K," Catalog No. P6556, 2003.

Simon, et al., "Detection of Phosphatidylinositol Glycan Class A Gene Transcripts by RT in Situ PCR Hybridization: A Comparative Study Using Fluorescein, Texas Red, and Digoxigenin-11 dUTP for Color Detection," *J. Histochem. Cytochem.*, 45:12, 1997, 1659-1664.

Stahlberg et al., "Properties of the Reverse Transcription Reaction in mRNA Quantification", *Clinical Chemistry*, 50(3), 2004, 509-515.

Stein, R., "Catalysis by Human Leukocyte Elastase: Substrate Structural Dependence of Rate-Limiting Protolytic Catalysis and Operation of the Charge Relay System", *J. Am. Chem. Soc.*, 105, 1983, 5111-5116.

Stein et al., "Mechanism of Inactivation of Human Leukocyte Elastase by a Chloromethyl Ketone: Kinetic and Solvent Isotope Effect Studies", *Biochemistry*, 25, 1986, 5414-5419.

Stratagene SideStep™ QPCRcDNA Synthesis Kit Instruction Manual, 2007.

Tullis, et al., "Calcium Protects DNase I from Proteinase K: A New Method for the Removal of Contaminating RNase from DNase I," *Analytical Biochemistry*, 107, 1980, 260-264.

Wolf et al., "Inhibition of Proteinase K by Methoxysuccinyl-Ala-Ala-Pro-Ala-chloromethyl Ketone", *J. Biol. Chem.*, 266(26), 1991, 17695-17699.

EPO Communication of a notice of opposition file by bioMerieux mailed Oct. 13, 2010 in App No. 03710760.4 (Patent No. 1476573) entered into EP phase from PCT/US03/02439 entitled "Crude Biological Derivatives Competent for Nucleic Acid Detection", Applicant: Ambion, Inc. and English translation thereof.

EPO Communication of a notice of opposition file by Konig Szynka Tilmann von Renesse mailed Oct. 19, 2010 in App No. 03710760.4 entered into EP phase from PCT/US03/02439 (Patent No. 1476573) entitled "Crude Biological Derivatives Competent for Nucleic Acid Detection", Applicant: Ambion, Inc.

International Search Report and Written Opinion mailed Mar. 30, 2010 in PCT App No. PCT/US09/68819.

Notice of Allowance mailed Apr. 11, 2011 in U.S. Appl. No. 12/122,274.

Office Action mailed Nov. 4, 2010 in U.S. Appl. No. 12/122,274.

Office Action mailed Aug. 18, 2010 in U.S. Appl. No. 12/122,274.

SEQUENCE LISTING

```
<160> NUMBER OF SEQ ID NOS: 21

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1

Ala Ala Pro Ala
1

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide

<400> SEQUENCE: 2
```

Ala Ala Pro Val
1

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide

<400> SEQUENCE: 3

Ala Pro Ala Val
1

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide

<400> SEQUENCE: 4

Ala Pro Ala Leu
1

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide

<400> SEQUENCE: 5

Ala Ala Pro Phe
1

<210> SEQ ID NO 6
<211> LENGTH: 4
<212> TYPE: PRT
<213> ORGANISM: Artificial Sequence
<220> FEATURE:
<223> OTHER INFORMATION: Synthetic peptide

<400> SEQUENCE: 6

Ala Pro Ala Phe
1

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide

<400> SEQUENCE: 7

Ala Ala Ala Pro Leu
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide

<400> SEQUENCE: 8

Ala Ala Ala Pro Val

```
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic peptide

<400> SEQUENCE: 9

Ala Ala Ala Pro Phe
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide

<400> SEQUENCE: 10

Ala Ala Pro Leu
1

<210> SEQ ID NO 11
<211> LENGTH: 4
<212> TYPE: PRT
<213> ORGANISM: Artificial Sequence
<220> FEATURE:
<223> OTHER INFORMATION: Synthetic peptide

<400> SEQUENCE: 11

Ala Ala Pro Tyr
1

<210> SEQ ID NO 12
<211> LENGTH: 4
<212> TYPE: PRT
<213> ORGANISM: Artificial Sequence
<220> FEATURE:
<223> OTHER INFORMATION: Synthetic peptide

<400> SEQUENCE: 12

Ala Ala Pro Trp
1

<210> SEQ ID NO 13
<211> LENGTH: 4
<212> TYPE: PRT
<213> ORGANISM: Artificial Sequence
<220> FEATURE:
<223> OTHER INFORMATION: Synthetic peptide

<400> SEQUENCE: 13

Ala Ala Pro Ile
1

<210> SEQ ID NO 14
<211> LENGTH: 4
<212> TYPE: PRT
<213> ORGANISM: Artificial Sequence
<220> FEATURE:
<223> OTHER INFORMATION: Synthetic peptide

<400> SEQUENCE: 14

Ala Ala Pro Thr
1
```

```
<210> SEQ ID NO 15
<211> LENGTH: 5
<212> TYPE: PRT
<213> ORGANISM: Artificial Sequence
<220> FEATURE:
<223> OTHER INFORMATION: Synthetic peptide

<400> SEQUENCE: 15

Ala Ala Ala Pro Ile
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic peptide

<400> SEQUENCE: 16

Ala Ala Ala Pro Thr
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic peptide

<400> SEQUENCE: 17

Ala Ala Pro Ala Val
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic peptide

<400> SEQUENCE: 18

Ala Ala Pro Ala Leu
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic peptide

<400> SEQUENCE: 19

Ala Ala Pro Ala Phe
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic peptide

<400> SEQUENCE: 20

Ala Ala Pro Ala Ala
1               5

<210> SEQ ID NO 21
```

```
<211> LENGTH: 5
<212> TYPE: PRT
<213> ORGANISM: Artificial Sequence
<220> FEATURE:
<223> OTHER INFORMATION: Synthetic peptide

<400> SEQUENCE: 21

Ala Ala Pro Ala Ile
1               5
```

PROTEINASE K INHIBITORS, METHODS AND COMPOSITIONS THEREFOR

The present application claims the benefit of U.S. Provisional Patent Application No. 61/139,279 filed Dec. 19, 2008, which application is incorporated by reference herein in its entirety.

FIELD

The present teachings generally relate to compositions, processes, methods, and kits for use of peptide proteinase K inhibitors, particularly for preparation of samples containing genetic material for analysis, detection and/or quantitation.

INTRODUCTION

Certain peptidyl chloromethyl ketones were among the first affinity labels developed for serine proteases and they were among the first active site-directed irreversible inhibitors reported for any enzyme. Wolf, W. M. et al. (*Journal of Biological Chemistry* 1991, 266, 17695) has reported an X-ray study at 2.2 Å resolution of a crystal structure of the transition state analog complex formed covalently between proteinase K and methoxysuccinyl-AlaAlaProAla-chloromethyl ketone (SEQ ID NO:1). The chloromethyl ketone group was reported to be covalently linked with His69(Nε) and Ser224(Oγ) to form the transition state analog. The peptide portion of the inhibitor is said to be in an extended conformation and fills the substrate recognition site as the central strand of a three-stranded antiparallel beta-pleated sheet. The X-ray study is cited as clearly showing that binding of proline interferes with peptide binding to proteinase K. The reference suggests that more effective inhibitors would have the proline substituted by another amino acid to avoid the steric interference with the recognition site.

Pending U.S. patent application Ser. No. 12/122,274 filed May 16, 2008 entitled "Sample Preparation for In Situ Nucleic Acid Analysis, Methods and Compositions Therefor," hereby incorporated by reference in its entirety, provides for use of certain tetrapeptide inhibitors of proteinase K, particularly methoxysuccinyl-AlaAlaProVal-chloromethyl ketone (SEQ ID NO:2), for preparation of samples containing genetic material for analysis.

The synthesis and biological evaluation of further methoxysuccinyl peptide chloromethyl ketones for use as proteinase K inhibitors are described herein.

SUMMARY

In some embodiments of a proteinase K inhibitor, a composition comprising at least one alkoxysuccinyl-peptidyl-haloalkyl ketone is provided, wherein the total binding free energy value of alkoxysuccinyl-peptidyl-haloalkyl ketone binding to proteinase K is equal to or lower than the total binding free energy value of methoxysuccinyl-AlaAlaProVal-chloromethyl ketone binding to proteinase K, and wherein the halo of haloalkyl is mono- or di-chloro, bromo, or iodo and the alkyl of haloalkyl or alkoxy is $C_1$-$C_3$ alkyl. Experimental studies provided herein demonstrate that such compositions possess inhibitory activity for proteinase K. Test inhibitors were evaluated experimentally and then evaluated using molecular modeling. Molecular modeling calculations provided values for total binding free energy for the binding of inhibitor to the proteinase K. A base value for total binding free energy was provided by the molecular modeling calculations with the inhibitor, methoxysuccinyl-AlaAlaProVal-chloromethyl ketone, and proteinase K.

In some embodiments, the least one alkoxysuccinyl-peptidyl-haloalkyl ketone comprises a peptidyl sequence of SEQ ID NO:3 to SEQ ID NO:21, wherein the halo of haloalkyl is mono- or di-chloro, bromo, or iodo and the alkyl of haloalkyl or alkoxy is $C_1$-$C_3$ alkyl. In some embodiments, the least one alkoxysuccinyl-peptidyl-haloalkyl ketone comprises a peptidyl sequence of SEQ ID NO:5, SEQ ID NO:7, or SEQ ID NO:9, wherein the halo of haloalkyl is mono- or di-chloro, bromo, or iodo and the alkyl of haloalkyl or alkoxy is $C_1$-$C_3$ alkyl.

In some embodiments of using a proteinase K inhibitor, a method of reducing activity of proteinase K is provided herein. The method comprises contacting proteinase K with a composition comprising at least one alkoxysuccinyl-peptidyl-haloalkyl ketone, wherein the total binding free energy value of alkoxysuccinyl-peptidyl-haloalkyl ketone binding to proteinase K is equal to or lower than the total binding free energy value of methoxysuccinyl-AlaAlaProVal-chloromethyl ketone binding to proteinase K, wherein the halo of haloalkyl is mono- or di-chloro, bromo, or iodo and the alkyl of haloalkyl or alkoxy is $C_1$-$C_3$ alkyl, and wherein activity of proteinase K is reduced thereby.

In some embodiments of use, a method of reducing activity of proteinase K comprises contacting proteinase K with a composition comprising at least one alkoxysuccinyl-peptidyl-haloalkyl ketone having a peptidyl sequence of SEQ ID NO:3 to SEQ ID NO:21, wherein the halo of haloalkyl is mono- or di-chloro, bromo, or iodo and the alkyl of haloalkyl or alkoxy is $C_1$-$C_3$ alkyl. In some embodiments, the halo group is a chloro group, the alkyl group is a methyl ($C_1$) group, and the alkoxy group is methoxy (MeO). In some embodiments, the least one alkoxysuccinyl-peptidyl-haloalkyl ketone comprises a peptidyl sequence of SEQ ID NO:5, SEQ ID NO:7, or SEQ ID NO:9, wherein the halo of haloalkyl is mono- or di-chloro, bromo, or iodo and the alkyl of haloalkyl or alkoxy is $C_1$-$C_3$ alkyl. The contacting is for a time and at a temperature such that proteinase K activity is reduced as compared to activity in the absence of the inhibitor.

Sample preparation process embodiments provided by teachings herein include a process for preparing a sample containing RNA for in situ analysis of RNA or a surrogate thereof. In some embodiments, a process for preparing a sample containing RNA for in situ analysis of RNA or a surrogate thereof is provided. The process comprises contacting the sample containing RNA with a lysis mixture under conditions and for a time to produce a lysate, wherein the lysis mixture comprises proteinase K or an enzymatically active mutant or variant thereof, a polypeptide having deoxyribonuclease activity, and a surfactant that substantially lacks fluorescence between 300 nm and 750 nm when in use for in situ analysis of RNA or a surrogate thereof, wherein the lysis mixture is substantially free of a cation chelator; and admixing the lysate with a stop mixture at substantially the same temperature as the contacting step to form a stopped mixture, wherein the stop mixture comprises a cation chelator effective to inactivate the polypeptide having deoxyribonuclease activity, and at least one alkoxysuccinyl-peptidyl-haloalkyl ketone wherein the total binding free energy value of alkoxysuccinyl-peptidyl-haloalkyl ketone binding to proteinase K is equal to or lower than the total binding free energy value of methoxysuccinyl-AlaAlaProVal-chloromethyl ketone binding to proteinase K, wherein the halo of haloalkyl is mono- or di-chloro, bromo, or iodo and the alkyl of haloalkyl or alkoxy is $C_1$-$C_3$ alkyl, and wherein the stopped mixture is thereby prepared for in situ analysis of RNA or a surrogate thereof.

In some embodiments, the process comprises contacting the sample containing RNA with a lysis mixture under conditions and for a time to produce a lysate, and admixing the lysate with a stop mixture at substantially the same temperature as the contacting step to form a stopped mixture. For such embodiments, the lysis mixture comprises proteinase K or an enzymatically active mutant or variant thereof, a polypeptide having deoxyribonuclease activity, and a surfactant that substantially lacks fluorescence between 300 nm and 750 nm when in use for in situ analysis of RNA or a surrogate thereof. Also, for such embodiments, the lysis mixture is substantially free of a cation chelator. The stop mixture comprises a cation chelator effective to inactivate the polypeptide having deoxyribonuclease activity, and an inhibitor of proteinase K comprising at least one alkoxysuccinyl-peptidyl-haloalkyl ketone having a peptidyl sequence of SEQ ID NO:3 to SEQ ID NO:21, wherein the halo of haloalkyl is mono- or di-chloro, bromo, or iodo and the alkyl of haloalkyl or alkoxy is $C_1$-$C_3$ alkyl. The resultant stopped mixture is compatible with in situ reverse transcriptase and DNA polymerase reactions. In some embodiments, the stop mixture further comprises a peptide or molecule having ribonuclease inhibitory activity. In some embodiments, the least one alkoxysuccinyl-peptidyl-haloalkyl ketone comprises a peptidyl sequence of SEQ ID NO:5, SEQ ID NO:7, or SEQ ID NO:9, wherein the halo of haloalkyl is mono- or di-chloro, bromo, or iodo and the alkyl of haloalkyl or alkoxy is $C_1$-$C_3$ alkyl.

In certain embodiments, the stopped mixture can be further combined with reagents for reverse transcription to form a first amplification mixture and, in some embodiments, the first amplification mixture is placed in contact with reagents for quantitative polymerase chain reaction (qPCR) amplification. In some embodiments, reagents for qPCR amplification comprise a green, yellow or orange emitter, and the process further comprises carrying out in situ analysis of the DNA, RNA, or a surrogate thereof comprising detecting fluorescence of the green, yellow, or orange emitter, respectively.

For certain embodiments, the sample preparation process of contacting and admixing are carried out at substantially the same temperature, which temperature is from 15° C. to 30° C., 16° C. to 28° C. or 19° C. to 25° C. as further described below.

In some embodiments, a process for preparing a sample containing RNA for in situ analysis of RNA or a surrogate thereof is provided, which process comprises contacting the sample containing RNA with a lysis mixture at 16° C. to 28° C. for a time to produce a lysate, and admixing the lysate with a stop mixture at substantially the same temperature as the contacting step to form a stopped mixture. For such embodiments, the lysis mixture comprises proteinase K or an enzymatically active mutant or variant thereof, DNase I, and a surfactant comprising TRITON X-114™ at a concentration from 0.02% to 3%, or 0.05% to 2%, or 0.05% to 1%, THESIT™ at a concentration of 0.01% to 5%, or 0.02% to 3%, or 0.05% to 2%, or 0.05% to 1%, or 0.05% to 0.5%, or 0.05% to 0.3%, TRITON X-100™ at a concentration of 0.05% to 3%, or 0.05% to 1%, or 0.05% to 0.3%, NONIDET P-40™ at a concentration of 0.05% to 5%, or 0.1% to 3%, or 0.1% to 2%, or 0.1% to 1% or 0.1% to 0.3% or 0.1% to 5%, or a combination thereof, and wherein the lysis mixture is substantially free of a cation chelator. Also for such embodiments, the stop mixture comprises a cation chelator in an amount effective to inactivate DNase I, and a proteinase K inhibitor comprising at least one alkoxysuccinyl-peptidyl-haloalkyl ketone having a peptidyl sequence of SEQ ID NO:3 to SEQ ID NO:21, wherein the halo of haloalkyl is mono- or di-chloro, bromo, or iodo and the alkyl of haloalkyl or alkoxy is $C_1$-$C_3$ alkyl. In some embodiments, the least one alkoxysuccinyl-peptidyl-haloalkyl ketone comprises a peptidyl sequence of SEQ ID NO:5, SEQ ID NO:7, or SEQ ID NO:9, wherein the halo of haloalkyl is mono- or di-chloro, bromo, or iodo and the alkyl of haloalkyl or alkoxy is $C_1$-$C_3$ alkyl. In some embodiments, the lysis mixture further comprises a calcium salt, a reducing agent, or a combination thereof. In some embodiments, the cation chelator of the stop mixture comprises ethylene glycol tetraacetic acid (EGTA). In further embodiments, the stop mixture comprises a ribonuclease inhibitor.

Sample preparation processes for samples containing DNA for in situ analysis of DNA or a surrogate thereof are provided by other embodiments herein. In some embodiments, a process for preparing a sample containing DNA for in situ analysis of DNA or a surrogate thereof is provided. The process comprises contacting the sample containing DNA with a lysis mixture under conditions and for a time to produce a lysate, wherein the lysis mixture comprises proteinase K or an enzymatically active mutant or variant thereof, and a surfactant that substantially lacks fluorescence between 300 nm and 750 nm when in use for in situ analysis of DNA or a surrogate thereof; and admixing the lysate with a stop mixture at substantially the same temperature as the contacting step to form a stopped mixture, wherein the stop mixture comprises at least one alkoxysuccinyl-peptidyl-haloalkyl ketone wherein the total binding free energy value of alkoxysuccinyl-peptidyl-haloalkyl ketone binding to proteinase K is equal to or lower than the total binding free energy value of methoxysuccinyl-AlaAlaProVal-chloromethyl ketone binding to proteinase K, wherein the halo of haloalkyl is mono- or di-chloro, bromo, or iodo and the alkyl of haloalkyl or alkoxy is $C_1$-$C_3$ alkyl, and wherein the stopped mixture is thereby prepared for in situ analysis of DNA or a surrogate thereof.

In further embodiments, a sample preparation process comprises contacting the sample containing DNA with a lysis mixture at 16° C. to 28° C. for a time and under conditions to produce a lysate, and admixing the lysate with a stop mixture at substantially the same temperature as the contacting step. For such embodiments, the lysis mixture comprises proteinase K, and a surfactant comprising TRITON X-114™ at a concentration from 0.02% to 3%, or 0.05% to 2%, or 0.05% to 1%, THESIT™ at a concentration of 0.01% to 5%, or 0.02% to 3%, or 0.05% to 2%, or 0.05% to 1%, or 0.05% to 0.5%, or 0.05% to 0.3%, TRITON X-100™ at a concentration of 0.05% to 3%, or 0.05% to 1%, or 0.05% to 0.3%, NONIDET P-40™ at a concentration in the lysis mixture of 0.05% to 5%, or 0.1% to 3%, or 0.1% to 2%, or 0.1% to 1% or 0.1% to 0.3%, or 0.1%-5%, or a combination thereof. In further embodiments, the lysis mixture comprises a peptide with ribonuclease activity. In addition, embodiments of the stop mixture comprise an inhibitor of proteinase K comprising at least one alkoxysuccinyl-peptidyl-haloalkyl ketone having a peptidyl sequence of SEQ ID NO:3 to SEQ ID NO:21, wherein the halo of haloalkyl is mono- or di-chloro, bromo, or iodo and the alkyl of haloalkyl or alkoxy is $C_1$-$C_3$ alkyl. In some embodiments, the least one alkoxysuccinyl-peptidyl-haloalkyl ketone comprises a peptidyl sequence of SEQ ID NO:5, SEQ ID NO:7, or SEQ ID NO:9, wherein the halo of haloalkyl is mono- or di-chloro, bromo, or iodo and the alkyl of haloalkyl or alkoxy is $C_1$-$C_3$ alkyl. Such an inhibitor has little to no inhibitory activity on DNA polymerase activity.

In some embodiments provided herein, a stop mixture is provided as a composition of matter. In some embodiments, a composition for inhibition of exogenously added proteinase K and DNase in a cell lysis mixture comprises a cation chelator, at least one alkoxysuccinyl-peptidyl-haloalkyl ketone wherein the total binding free energy value of alkoxysuccinyl-peptidyl-haloalkyl ketone binding to proteinase K is equal to or lower than the total binding free energy value of methoxysuccinyl-AlaAlaProVal-chloromethyl ketone binding to proteinase K, and wherein the halo of haloalkyl is mono- or di-chloro, bromo, or iodo and the alkyl of haloalkyl or alkoxy is $C_1$-$C_3$ alkyl; and an inhibitor of a ribonuclease.

In some embodiments, a stop mixture composition comprises a cation chelator; at least one alkoxysuccinyl-peptidyl-haloalkyl ketone having a peptidyl sequence of SEQ ID NO:3 to SEQ ID NO:21, wherein the halo of haloalkyl is mono- or di-chloro, bromo, or iodo and the alkyl of haloalkyl or alkoxy is $C_1$-$C_3$ alkyl; and an inhibitor of a ribonuclease. In some embodiments, the least one alkoxysuccinyl-peptidyl-haloalkyl ketone comprises a peptidyl sequence of SEQ ID NO:5, SEQ ID NO:7, or SEQ ID NO:9, wherein the halo of haloalkyl is mono- or di-chloro, bromo, or iodo and the alkyl of haloalkyl or alkoxy is $C_1$-$C_3$ alkyl. In some embodiments, the haloalkyl ketone is chloromethyl ketone and the alkoxy is methoxy.

For certain embodiments, kits for preparation of a sample containing RNA for in situ detection of RNA or a surrogate thereof are provided. In some embodiments, such a kit comprises lysis mixture components comprising proteinase K or an enzymatically active mutant or variant thereof, a surfactant that substantially lacks fluorescence between 300 nm and 750 nm when in use for in situ analysis of RNA or a surrogate thereof, and a polypeptide having deoxyribonuclease activity, wherein the lysis solution components are substantially free of a cation chelator; and stop mixture components comprising: a cation chelator, and at least one alkoxysuccinyl-peptidyl-haloalkyl ketone wherein the total binding free energy value of alkoxysuccinyl-peptidyl-haloalkyl ketone binding to proteinase K is equal to or lower than the total binding free energy value of methoxysuccinyl-AlaAlaProVal-chloromethyl ketone binding to proteinase K, and wherein the halo of haloalkyl is mono- or di-chloro, bromo, or iodo and the alkyl of haloalkyl or alkoxy is $C_1$-$C_3$ alkyl.

In some embodiments, such kits comprise lysis solution components comprising proteinase K or an enzymatically active mutant or variant thereof; a surfactant comprising TRITON X-114™, THESIT™, TRITON X-100™, NONIDET P-40™, or a combination thereof; and a polypeptide having deoxyribonuclease activity; wherein the lysis solution components are substantially free of a cation chelator. The kits may also comprise stop mixture components comprising a cation chelator, at least one alkoxysuccinyl-peptidyl-haloalkyl ketone having a peptidyl sequence of SEQ ID NO:3 to SEQ ID NO:21, wherein the halo of haloalkyl is mono- or di-chloro, bromo, or iodo and the alkyl of haloalkyl or alkoxy is $C_1$-$C_3$ alkyl, and optionally, a ribonuclease inhibitor. In some embodiments, the least one alkoxysuccinyl-peptidyl-haloalkyl ketone comprises a peptidyl sequence of SEQ ID NO:5, SEQ ID NO:7, or SEQ ID NO:9, wherein the halo of haloalkyl is mono- or di-chloro, bromo, or iodo and the alkyl of haloalkyl or alkoxy is $C_1$-$C_3$ alkyl. The stop mixture components may also include a reducing agent.

For certain embodiments, kits for preparation of a sample containing DNA for in situ detection of DNA or a surrogate thereof are provided. In some embodiments, such a kit comprises lysis mixture components comprising proteinase K or an enzymatically active mutant or variant thereof, and a surfactant that substantially lacks fluorescence between 300 nm and 750 nm when in use for in situ analysis of RNA or a surrogate thereof, and stop mixture components comprising at least one alkoxysuccinyl-peptidyl-haloalkyl ketone wherein the total binding free energy value of alkoxysuccinyl-peptidyl-haloalkyl ketone binding to proteinase K is equal to or lower than the total binding free energy value of methoxysuccinyl-AlaAlaProVal-chloromethyl ketone binding to proteinase K, and wherein the halo of haloalkyl is mono- or di-chloro, bromo, or iodo and the alkyl of haloalkyl or alkoxy is $C_1$-$C_3$ alkyl.

In some embodiments for in situ detection of DNA, kits comprise lysis solution components comprising proteinase K or an enzymatically active mutant or variant thereof; a surfactant comprising TRITON X-114™, THESIT™, TRITON X-100™, NONIDET P-40™, or a combination thereof. The kits may also comprise stop mixture components comprising at least one alkoxysuccinyl-peptidyl-haloalkyl ketone having a peptidyl sequence of SEQ ID NO:3 to SEQ ID NO:21, wherein the halo of haloalkyl is mono- or di-chloro, bromo, or iodo and the alkyl of haloalkyl or alkoxy is $C_1$-$C_3$ alkyl; and optionally, a deoxyribonuclease inhibitor. In some embodiments, the least one alkoxysuccinyl-peptidyl-haloalkyl ketone comprises a peptidyl sequence of SEQ ID NO:5, SEQ ID NO:7, or SEQ ID NO:9, wherein the halo of haloalkyl is mono- or di-chloro, bromo, or iodo and the alkyl of haloalkyl or alkoxy is $C_1$-$C_3$ alkyl. The stop mixture components may also include a reducing agent.

Kit embodiments can further comprise one or more reagents for reverse transcription, such as reverse transcriptase, a reverse primer, dNTPs or a reverse transcriptase buffer, or can further comprise one or more reagents for PCR, such as a DNA polymerase, for example.

In some embodiments, processes and compositions are compatible with downstream nucleic acid detection methods using methods such as reverse transcription, polymerase chain reaction, qPCR, qRT-PCR, melt curve analysis, sequencing, message amplification, preamplification, detection, linear amplification for array analysis, and others that use CYANINE™ 3 or CYANINE™ 5 in array analysis, for example. As an example of compatibility with in situ nucleic acid detection methods, Examples 2 and 3 herein provide results from both indirect linked assays and direct assays of inhibitory activity on proteinase K. The indirect linked assays provide for contacting proteinase K with a test inhibitor, then adding reverse transcriptase followed by components for amplification, and detecting the resulting amplicon during real time PCR. The direct assays provide for contacting proteinase K with a test inhibitor, then adding BSA to test for residual proteinase K activity. Both assays demonstrate inhibition of proteinase K by inhibitors provided herein.

In some embodiments herein, a method for identifying an alkoxysuccinyl-peptidyl-haloalkyl ketone as a proteinase K inhibitor wherein the halo of haloalkyl is mono- or di-chloro, bromo, or iodo and the alkyl of haloalkyl or alkoxy is C1-C3 alkyl, comprises one or more of steps a, and b as follows. Step a is determining the total binding free energy value of a candidate alkoxysuccinyl-peptidyl-haloalkyl ketone to proteinase K, and identifying the candidate alkoxysuccinyl-peptidyl-haloalkyl ketone as a proteinase K inhibitor when the total binding free energy value is equal to or lower than a total binding free energy value of methoxysuccinyl-AlaAla-ProVal-chloromethyl ketone binding to proteinase K. Step b is contacting proteinase K with a candidate alkoxysuccinyl-peptidyl-haloalkyl ketone under reaction conditions to allow a complex to form, followed by contacting a proteinase K substrate with the complex, and identifying the candidate alkoxysuccinyl-peptidyl-haloalkyl ketone as a proteinase K inhibitor when the substrate is substantially undigested as compared to an amount of digestion of the substrate in the presence of a proteinase K-methoxysuccinyl-AlaAlaProVal-chloromethyl ketone complex under equivalent conditions. In some embodiments, the method comprises step b and the reaction conditions include a cellular lysate preparation comprising exogenously added proteinase K. In some embodiments, the proteinase K substrate contacted with the complex is a reverse transcriptase.

Sample preparation processes provided by embodiments herein are useful for any method where RNA or DNA is analyzed, e.g., detected or quantitated. Stopped samples may be used for genotyping analysis, gene expression analysis, copy number analysis, DNA methylation analysis, SNP genotyping, plant cell genotyping, or RNA analysis including, for example, analysis, detection or quantitation of mRNA and noncoding RNA such as, for example, rRNA, siRNA, snRNA, or miRNA.

Sample preparation embodiments presented by teachings herein provide surprisingly fast, efficient, and ambient temperature production of a lysate that is RT and PCR ready due, in part, to provision of conditions under which proteinase K and a deoxyribonuclease can carry out enzymatic activity at the same time and in the same reaction mixture. Sample preparation embodiments presented herein can be performed on cells that are in suspension or on cells that are attached to a growth surface such as for 96- or 384-well culture plates. These and other features of the present teachings will become more apparent from the description herein.

DRAWINGS

The skilled artisan will understand that the drawings, described below, are for illustration purposes only. The drawings are not intended to limit the scope of the present teachings in any way.

FIG. 1 provides a plot of average cycle threshold versus various concentrations of the known proteinase K inhibitor MeOSuc-AAPV-CH$_2$Cl (SEQ ID NO:2; positive control), and for four test inhibitors MeOSuc-APAV-CH$_2$Cl (SEQ ID NO:3), MeOSuc-APAL-CH$_2$Cl (SEQ ID NO:4), MeOSuc-AAPF-CH$_2$Cl (SEQ ID NO:5), and MeOSuc-APAF-CH$_2$Cl (SEQ ID NO:6) ranging in concentration from 1 mM to 0.05 mM in a stopped mixture using the TaqMan® Gene Expression Cells-to-C$_T$™ Kit (Applied Biosystems, Foster City, Calif.) as described in Example 2. MeOSuc-AAPF-CH$_2$Cl (SEQ ID NO:5) demonstrates inhibitory activity for proteinase K to as low a concentration as 0.05 mM in the stopped mixture.

FIG. 2 provides a Bioanalyzer protein gel showing residual proteinase K activity after exposure of the proteinase K to the test inhibitor MeOSuc-AAPF-CH$_2$Cl (SEQ ID NO:5). The substrate for proteinase K is bovine serum albumin (BSA) which has a molecular weight of about 70 kD. Proteinase K is at about 35 kDa. The lanes of FIG. 2 are as follows from left to right: Ladder; BSA only; No BSA (proteinase K only); MeOSucAAPF-CH$_2$Cl (SEQ ID NO:5) in the stopped mixture at 1 mM, 0.75 mM, 0.5 mM, 0.25 mM, 0.125 mM, and 0 mM.

FIG. 3 provides data from a protein gel in which the marker ladder ranges in size from 10 kD to 250 kD, intact Ultrapure BSA substrate (Applied Biosystems) is at about 70 Kd, and proteinase K is at about 35 kDa. The lanes of FIG. 3 are as follows: Ladder, BSA, No BSA (proteinase K only), 0.75 mM MeOSuc-AAPV-CH$_2$Cl (SEQ ID NO:2), 0.75 mM MeOSuc-AAPF-CH$_2$Cl (SEQ ID NO:5), 0.5 mM MeOSuc-AAPV-CH$_2$Cl (SEQ ID NO:2), 0.5 mM MeOSuc-AAPF-CH$_2$Cl (SEQ ID NO:5), 0.250 mM MeOSuc-AAPV-CH$_2$Cl (SEQ ID NO:2), 0.250 mM MeOSuc-AAPF-CH$_2$Cl (SEQ ID NO:5), 0.125 mM MeOSuc-AAPV-CH$_2$Cl (SEQ ID NO:2), 0.125 mM MeOSuc-AAPF-CH$_2$Cl (SEQ ID NO:5), 0.065 mM MeOSuc-AAPV-CH$_2$Cl (SEQ ID NO:2), 0.065 mM MeOSuc-AAPF-CH$_2$Cl (SEQ ID NO:5), 0 mM MeOSuc-AAPV-CH$_2$Cl (SEQ ID NO:2), and 0 mM MeOSuc-AAPF-CH$_2$Cl (SEQ ID NO:5). The MeOSuc-AAPF-CH$_2$Cl (SEQ ID NO:5) compound was capable of inhibiting proteinase K at concentrations at least half that of MeOSuc-AAPV-CH$_2$Cl (SEQ ID NO:2), (compare the lanes at 0.5 mM and at 0.25 mM).

FIG. 4A-FIG. 4D provide molecular model building showing protein-inhibitor interactions for MeOSuc-AAPF-CH$_2$Cl (SEQ ID NO:5) (FIG. 4A and FIG. 4B) and for MeOSuc-AAPV-CH$_2$Cl (SEQ ID NO:2) (FIG. 4C and FIG. 4D) based on coordinates of proteinase K or elastase in a complex with MeOSuc-AAPA-CH$_2$Cl (SEQ ID NO:1) as described in Example 4. MSFCK, MeOSuc-AlaAlaProPhe-CH$_2$Cl (SEQ ID NO:5); MSVCK, MeOSuc-AlaAlaProVal-CH$_2$Cl (SEQ ID NO:2).

FIG. 5 provides a plot of average cycle threshold versus various concentrations of each compound in the stopped reactions. Results are provided for the proteinase K tetrapeptide inhibitor MeOSuc-AAPV-CH$_2$Cl (SEQ ID NO:2) (positive control), and for three test pentapeptide inhibitors MeOSuc-AAAPL-CH$_2$Cl (SEQ ID NO:7), MeOSuc-AAAPV-CH$_2$Cl (SEQ ID NO:8), and MeOSuc-AAAPF-CH$_2$Cl (SEQ ID NO:9) ranging in concentration from 1 mM to 0 mM in the stopped mixtures using the TaqMan® Gene Expression Cells-to-C$_T$™ Kit (Applied Biosystems, Foster City, Calif.) as described in Example 6. Control reactions included 100% heat killed mixtures in which proteinase K activity is fully inactivated, control non-heat killed PK, and control Xeno™ RNA template (Xeno Control).

FIG. 6 provides data showing the detection of β-actin in HeLa cell cultures using methods herein, which data thereby validate use of the present methods in vitro. Results are provided for the control inhibitor MeOSuc-AAPV-CH$_2$Cl (SEQ ID NO:2), MeOSuc-AAAPL-CH$_2$Cl (SEQ ID NO:7) (designated A3PL), MeOSuc-AAAPV-CH$_2$Cl (SEQ ID NO:8) (designated A3PV), MeOSuc-AAPL-CH$_2$Cl (SEQ ID NO:10) and MeOSuc-AAAPF-CH$_2$Cl (SEQ ID NO:9) (designated A3 PF). The stop solution control contains 1 mM methoxysuccinyl-AAPV-chloromethyl ketone (SEQ ID NO:2).

FIG. 7 provides data from a protein gel in which the marker ladder ranges in size from 10 kDa to 260 kDa, intact Ultrapure BSA substrate (Applied Biosystems) is at about 70 Kd, and proteinase K is at about 35 kDa. The lanes of FIG. 7 are as follows: Ladder (Novex® Sharp Pre-Stained Protein Standard (Invitrogen, Carlsbad Calif.)), BSA control, BSA+proteinase K control, 1 mM MeOSuc-AAPV-CH$_2$Cl (SEQ ID NO:2) as a positive control, and MeOSuc-AAAPL-CH$_2$Cl (SEQ ID NO:7) at 1 mM, 0.75 mM, 0.5 mM, 0.25 mM, 0.10 mM, 0.05 mM, and 0.0 mM and as provided in Example 8. The MeOSuc-AAAPL-CH$_2$Cl (SEQ ID NO:7) compound was capable of inhibiting proteinase K at a concentration as low as 0.10 mM in the stopped mixture.

DESCRIPTION OF VARIOUS EMBODIMENTS

Figure 1:
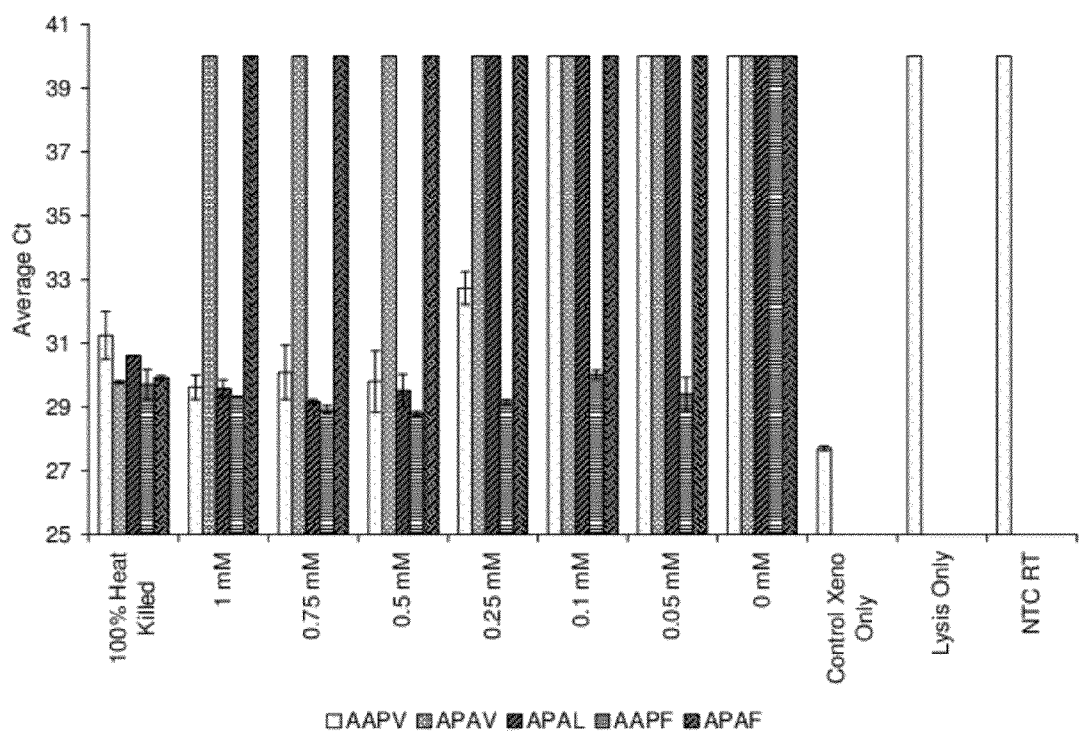

It is to be understood that both the foregoing general description and the following detailed description are exemplary and explanatory only and are not intended to limit the scope of the current teachings. In this application, the use of the singular includes the plural unless specifically stated otherwise. The use of "comprise", "contain", and "include", or modifications of those root words, for example but not limited to, "comprises", "contained", and "including", are not intended to be limiting. Use of "or" means "and/or" unless stated otherwise. The term "and/or" means that the terms before and after can be taken together or separately. For illustration purposes, but not as a limitation, "X and/or Y" can mean "X" or "Y" or "X and Y." As used herein and unless otherwise indicated, the terms "a" and "an" are taken to mean "one," "at least one" or "one or more."

Whenever a range of values is provided herein, the range is meant to include the starting value and the ending value and a value or value range there between unless otherwise specifically stated. For example, "from 0.2 to 0.5" means 0.2, 0.3, 0.4, 0.5; ranges there between such as 0.2-0.3, 0.3-0.4, 0.2-0.4; increments there between such as 0.25, 0.35, 0.225, 0.335, 0.49; increment ranges there between such as 0.26-0.39; and the like.

The section headings used herein are for organizational purposes only and are not to be construed as limiting the subject matter described in any way. All literature and similar materials cited in this application including, but not limited to, patents, patent applications, articles, books, treatises, and internet web pages, regardless of the format of such literature and similar materials, are expressly incorporated by reference in their entirety for any purpose. In the event that one or more of the incorporated literature and similar materials defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Certain trademarked products are cited by teachings herein with reference to surfactants. Generic descriptions for such products are as follows: TRITON X-100™, octylphenol ethoxylate having an average of 9.5 ethoxylate groups (Dow Chemical Company Product Information, Form No. 119-01882, JMS1206); TRITON X-114™, octylphenol ethoxylate having an average of 7.5 ethoxylate groups (Dow Chemical Company Product Information, Form No. 119-01884, JMS 1206); NONIDET P-40™, octylphenolpoly(ethyleneglycolether) (Roche Diagnostics GmbH, Catalog No. 11 332 473 001, July 2005); and THESIT™, dodecyl alcohol polyoxyethylene ether (IUPAC Name 2-dodecoxyethanol; CAS Number 9002-92-0; Chemical Formula $C_{14}H_{30}O_2$).

45. Abbreviations for amino acids in peptide designations herein include one letter or three letter abbreviations including A or Ala for alanine; F or Phe for phenylalanine; I or Ile for isoleucine; L or Leu for leucine; P or Pro for proline; T or Thr for threonine; V or Val for valine, W or Trp for tryptophan, and Y or Tyr for tyrosine. For tetrapeptide inhibitor compounds, the position of each amino acid in the tetrapeptide can be referred to as position 1 (first), position 2 (second), position 3 (third), or position 4 (fourth) when using standard amino acid sequence numbering system beginning at an N-terminal end. Alternatively, in referring to the amino acid positions of a tetrapeptide inhibitor using the Schechter nomenclature referred to in Wolf et al. cited above, the N-terminal amino acid is referred to as in the P4 position, the next amino acid in the sequence is referred to as in the P3 position, the following amino acid in the sequence is referred to as in the P2 position, while the C-terminal amino acid is referred to as in the P1 position.

Standard abbreviations are used for chemicals, such as for example, Suc for succinyl, MeO for methoxy, and CMK for chloromethyl ketone. Other abbreviations are as described herein.

An inhibitor of proteinase K: An inhibitor of proteinase K, as used herein, is an alkoxysuccinyl peptidyl haloalkyl ketone wherein the halo is mono- or di-chloro, iodo or bromo and the alkyl of the haloalkyl or alkoxy is $C_1$ to $C_3$ or active derivatives or analogs thereof. In some embodiments, the peptidyl portion is a tetrapeptide or a pentapeptide. In some embodiments, a total binding free energy value of the alkoxysuccinyl-peptidyl-haloalkyl ketone to proteinase K to form the proteinase K-inhibitor complex is equal to or lower than a total binding free energy value of methoxysuccinyl-AlaAlaProVal-chloromethyl ketone (SEQ ID NO:2) to proteinase K to from a proteinase K-methoxysuccinyl-AlaAlaProVal-chloromethyl ketone (SEQ ID NO:2) complex. In some embodiments, a total binding free energy value of the alkoxysuccinyl-peptidyl-haloalkyl ketone to proteinase K to form the proteinase K-inhibitor complex is greater than a total binding free energy value of methoxysuccinyl-AlaAlaProVal-chloromethyl ketone (SEQ ID NO:2) to proteinase K to from a proteinase K-methoxysuccinyl-AlaAlaProVal-chloromethyl ketone (SEQ ID NO:2) complex. Total binding free energy of an inhibitor to proteinase K to form a proteinase K-inhibitor complex can be determined by use of, for example, Molecular Dynamics, or Monte Carlo methods known to one of skill in the art.

In some embodiments, the peptide portion of the alkoxysuccinyl peptide haloalkyl ketone inhibitor of proteinase K comprises SEQ ID NO:3 to SEQ ID NO:21, or a combination thereof. In some embodiments, the least one alkoxysuccinyl-peptidyl-haloalkyl ketone comprises a peptidyl sequence of SEQ ID NO:5, SEQ ID NO:7, or SEQ ID NO:9, wherein the halo of haloalkyl is mono- or di-chloro, bromo, or iodo and the alkyl of haloalkyl or alkoxy is $C_1$-$C_3$ alkyl.

For convenience, Table 1 provides the assignment of sequence listing identification numbers to the peptidyl portions of some embodiments of alkoxysuccinyl peptide haloalkyl ketone inhibitors.

TABLE 1

| Peptidyl portion of Inhibitor | SEQ ID NO: |
|---|---|
| AAPA | 1 |
| AAPV | 2 |
| APAV | 3 |
| APAL | 4 |
| AAPF | 5 |
| APAF | 6 |
| AAAPL | 7 |
| AAAPV | 8 |
| AAAPF | 9 |
| AAPL | 10 |
| AAPY | 11 |
| AAPW | 12 |
| AAPI | 13 |
| AAPT | 14 |
| AAAPI | 15 |
| AAAPT | 16 |
| AAPAV | 17 |
| AAPAL | 18 |
| AAPAF | 19 |
| AAPAA | 20 |
| AAPAI | 21 |

In some embodiments, an alkoxysuccinyl tetrapeptide haloalkyl ketone inhibitor of proteinase K comprises MeO-Suc-AlaAlaProPhe-CH$_2$Cl (SEQ ID NO:5), MeOSuc-AlaProAlaLeu-CH$_2$Cl (SEQ ID NO:4), MeOSuc-AlaAlaProTyr-CH$_2$Cl (SEQ ID NO:11), MeOSuc-AlaAlaProTrp-CH$_2$Cl (SEQ ID NO:12), MeOSuc-AlaAlaProLeu-CH$_2$Cl (SEQ ID NO:10), MeOSuc-AlaAlaProIle-CH$_2$Cl (SEQ ID NO:13), MeOSuc-AlaAlaProThr-CH$_2$Cl (SEQ ID NO:14), or a combination thereof. In some embodiments, the alkoxysuccinyl tetrapeptide haloalkyl ketone inhibitor of proteinase K is other than MeOSuc-AlaAlaProAla-CH$_2$Cl (SEQ ID NO:1). In some embodiments, the alkoxysuccinyl tetrapeptide haloalkyl ketone inhibitor of proteinase K is other than MeO-Suc-AlaAlaProVal-CH$_2$Cl (SEQ ID NO:2).

In some embodiments, an alkoxysuccinyl pentapeptide haloalkyl ketone inhibitor of proteinase K comprises MeO-Suc-AlaAlaAlaProPhe-CH$_2$Cl (SEQ ID NO:9), MeOSuc-AlaAlaAlaProVal-CH$_2$Cl (SEQ ID NO:8), MeOSuc-AlaAlaAlaProLeu-CH$_2$Cl (SEQ ID NO:7), MeOSuc-AlaAlaAlaProIle-CH$_2$Cl (SEQ ID NO:15), MeOSuc-AlaAlaAlaProThr-CH$_2$Cl (SEQ ID NO:16), or a combination thereof.

In some embodiments, an alkoxysuccinyl peptide haloalkyl ketone inhibitor of proteinase K comprises MeO-Suc-AlaAlaProPhe-CH$_2$Cl (SEQ ID NO:5), MeOSuc-AlaAlaProLeu-CH$_2$Cl (SEQ ID NO:7), or a combination thereof. In some embodiments, the alkoxysuccinyl-peptidyl-haloalkyl ketone is methoxysuccinyl-AAPF-chloromethyl ketone (SEQ ID NO:5) or methoxysuccinyl-AAAPL-chloromethyl ketone (SEQ ID NO:7). In some embodiments, an alkoxysuccinyl peptide haloalkyl ketone inhibitor of proteinase K comprises MeOSuc-AlaProAlaLeu-CH$_2$Cl (SEQ ID NO:4), The inhibitor has essentially no inhibitory effect on reverse transcriptase or on DNA polymerase. Methoxysuccinyl-AAPV-chloromethyl ketone (SEQ ID NO:2) is described by U.S. patent application Ser. No. 12/122,274 as having inhibitory activity for 100 µg/ml proteinase K at a concentration as low as 0.25 mM and as having compatibility with both one-step and two-step RT-PCR reactions. Results presented herein demonstrate that MeOSuc-AlaAlaProPhe-CH$_2$Cl (SEQ ID NO:5) provides unexpectedly better inhibitory activity for proteinase K to as low a concentration of 0.05 mM as compared with the MeOSuc-AlaAlaProVal-CH$_2$Cl (SEQ ID NO:2) inhibitor. Results presented herein also demonstrate unexpected proteinase K inhibitory activity by MeO-Suc-AlaProAlaLeu-CH$_2$Cl (SEQ ID NO:4) (see Example 2), MeOSuc-AlaAlaAlaProLeu-CH$_2$Cl (SEQ ID NO:7) (see Examples 6 and 7), and MeOSuc-AlaAlaAlaProPhe-CH$_2$Cl (SEQ ID NO:9) (see Examples 6 and 7).

Synthesis of the tetrapeptide ketone inhibitors is presented in Example 1 and synthesis of the pentapeptide ketone inhibitors is presented in Example 5. In light of the teachings of Examples 1 and 5, one of skill in the art would be able to choose alkoxysuccinyl and haloalkyl derivatives of the amino acid synthon for synthesis of various alkoxysuccinyl and haloalkyl derivatives of tetrapeptide inhibitors provided herein. For example, while synthesis of the chloromethyl derivatives of tetrapeptide ketones are provided in Example 1, one of skill in the art would be able to synthesize a bromoethyl derivative or an iodopropyl, or any combination of halo groups with methyl, ethyl, or propyl groups by appropriate substitution. A chloromethyl ketone derivative of tyrosine or tryptophan can be synthesized using methods known to one of skill in the art such as for valine, for example, as in Powers et al. (*BBA* 485 (1977) 156-166). Examples 1 and 5 provide synthesis of methoxysuccinyl derivatives using methyl succinimidosuccinate; one of skill in the art in light of Examples 1 and 5 would be able to synthesize an ethoxy- or propoxysuccinyl derivative using an ethyl or propyl succinimidosuccinate, respectively. Synthesis of hexapeptide ketone inhibitors and longer peptidyl ketone inhibitors can be achieved using the chemistry presented in Examples 1 and 5 by adding an amino acid to the C-terminal group of synthons as provided therein.

Temperature: Proteinase K has a broad temperature profile; only at temperatures higher than about 65° C. does the enzyme show decreasing activity. The sample preparation processes of teachings herein include a contacting step to produce a lysate and an admixing step where the lysate is mixed with a stop mixture where the steps are carried out at substantially the same temperature. "Substantially the same temperature" generally refers to an isothermal process of holding the temperature relatively constant during the contacting and admixing steps and, for certain embodiments described herein, means ambient temperature which temperature may change during the day or from lab to lab. In general, the contacting and admixing steps are carried out at substantially the same temperature, which temperature is about 15° C. to 40° C., or about 16° C. to 28° C. or about 19° C. to 26° C., or about 19° C. to 25° C., or about 22° C. to 25° C., or at ambient temperature, or about 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C. An isothermal process is particularly amenable for high throughput analyses.

Sample: The term "sample," as used herein, refers to an in vitro cell, cell culture, virus, bacterial cell, fungal cell, plant cell, bodily sample, or tissue sample that contains genetic material. In certain embodiments, the genetic material of the sample comprises RNA. In other embodiments, the genetic material of the sample is DNA, or both RNA and DNA. In certain embodiments, a tissue sample includes a cell isolated from a subject. A subject includes any organism from which a sample can be isolated. Non-limiting examples of organisms include prokaryotes, eukaryotes or archaebacteria, including bacteria, fungi, animals, plants, or protists. The animal, for example, can be a mammal or a non-mammal. The mammal can be, for example, a rabbit, dog, pig, cow, horse, human, or a rodent such as a mouse or rat. In particular aspects, the tissue sample is a human tissue sample. The tissue sample can be, for example, a blood sample. The blood sample can be whole blood or a blood product (e.g., red blood cells, white blood cells, platelets, plasma, serum). The sample, in other non-limiting embodiments, can be saliva, a cheek, throat, or nasal swab, a fine needle aspirate, a tissue print, cerebral spinal fluid, mucus, lymph, feces, urine, skin, spinal fluid, peritoneal fluid, lymphatic fluid, aqueous or vitreous humor, synovial fluid, tears, semen, seminal fluid, vaginal fluids, pulmonary effusion, serosal fluid, organs, bronchio-alveolar lavage, tumors, frozen cells, or constituents or components of in vitro cell cultures. In other aspects, the tissue sample is a solid tissue sample or a frozen tissue sample. In still further aspects, the sample comprises a virus, bacteria, or fungus. The sample can be an ex vivo tissue or sample or a sample obtained by laser capture microdissection. The sample can be a fixed sample, including as set forth by U.S. Published Patent Application No. 2003/0170617 filed Jan. 28, 2003.

Sample preparation processes provided by teachings herein are for from one cell up to about $10^5$-$10^6$ cells per sample or any range therebetween. For certain cell lines, such as HeLa cells, linear Ct values can be obtained for up to $10^6$ cells per sample preparation. A patient needle biopsy often consists of thousands of cells. A biopsy could be prepared using methods herein, PCR amplified and analyzed by measuring the expression of certain genes, for example.

In some embodiments, the sample is removed from serum components prior to preparation. In some embodiments, the sample is washed with a solution comprising, for example, but not limited to, phosphate-buffered saline (PBS), physiological saline, serum-free media or suitable solution with appropriate tonicity.

In situ analysis of genetic material or a surrogate thereof: The term "in situ analysis," as used herein means that processes provided herein allow DNA or RNA analysis to be carried out in the same tube or on an aliquot of the stopped mixture without centrifugation or extraction. That is, RNA or DNA need not be isolated from the stopped mixture prior to mixing at least a portion of the stopped mixture with a composition comprising reverse transcriptase or another relevant enzyme. The term "or a surrogate thereof," as used herein means a detectable product that represents the RNA or DNA present in the sample, such as an amplified product of the RNA or DNA.

Lysis Mixture: A "lysis mixture," as used herein, comprises components for isothermally lysing a sample and lacks components that can interfere with later detection of DNA or RNA, or a surrogate thereof, using emission detection at wavelengths of 300 nm to 750 nm. A lysis mixture for RNA analysis comprises a lysis solution and a polypeptide having deoxyribonuclease activity. A lysis mixture for DNA analysis lacks a polypeptide having deoxyribonuclease activity and may contain, in some embodiments, a polypeptide having ribonuclease activity. A lysis reaction is a lysis mixture combined with a sample. Incubation of a lysis reaction can be for any range of time between about 1 minute to about 30 minutes, between 2 minutes to about 30 minutes, about 2 minutes to about 20 minutes, about 3 minutes to about 15 minutes, about 4 minutes to about 10 minutes, about 8 minutes, about 7 minutes, about 6 minutes, or about 5 minutes.

A lysis solution comprises, for certain embodiments herein, a Tris-base or Tris-Cl buffer at a pH of about 7.5 to about 8.2 for a range of temperatures such as 19° C. to 25° C., a polypeptide having protease activity, and a surfactant that substantially lacks fluorescence between 300 nm and 750 nm. The lysis solution is used at a lysis-effective concentration. Further, the lysis solution is substantially free of a cation chelator.

Polypeptide having protease activity: In certain embodiments herein, the lysis solution comprises a polypeptide having protease activity such as for example, the serine protease, proteinase K. In addition to or in lieu of proteinase K, the lysis solution can comprise a serine protease such as trypsin, chymotrypsin, elastase, subtilisin, streptogrisin, thermitase, aqualysin, plasmin, cucumisin, or carboxypeptidase A, D, C, or Y. In addition to a serine protease, the lysis solution can comprise a cysteine protease such as papain, calpain, or clostripain; an acid protease such as pepsin, chymosin, or cathepsin; or a metalloprotease such as pronase, thermolysin, collagenase, dispase, an aminopeptidase or carboxypeptidase A, B, E/H, M, T, or U. Proteinase K is stable over a wide pH range (pH 4.0-10.0) and is stable in buffers with denaturing reagents such as urea, SDS and guanidinium salts. Enzymatically active mutants or variants of a protease as described below are considered equivalents to the native protease for purposes of the present disclosure.

A surfactant that substantially lacks fluorescence between 300 nm and 750 nm when in use for in situ analysis of DNA, RNA or a surrogate thereof: In embodiments provided herein, the lysis solution comprises a surfactant at a concentration that has low or no emission at the emission wavelengths of dyes or labels commonly used for detecting RNA or DNA when in use for in situ analysis of DNA, RNA or a surrogate thereof.

A lysis-effective concentration of surfactant in a lysis mixture is a concentration of surfactant at which a sample is considered fully lysed as determined by propidium iodide staining using 1% TRITON X-100™ surfactant as a control. Lysis-effective concentrations of exemplary surfactants range from 0.02% or 0.05% to 3% or more for TRITON X-114™ surfactant, from 0.01% or 0.05% to 5% or more for THESIT™ surfactant, from 0.1% to 5% or more for NONIDET P-40™ surfactant, and from 0.05% to 1% or to 3% for TRITON X-100™ surfactant. When a combination of surfactants is used, the concentration of each surfactant may be lowered from the cited amounts.

For the methods and processes described herein, the lysate is diluted when stop solution is added. The stopped mixture is further diluted when a portion is transferred to a RT-qPCR reaction. The concentration of surfactant in the qPCR reaction is thereby diluted when compared to the concentration of the surfactant in the lysate. The dilution factor may range from a 1.25-fold dilution to a thousand-fold or more dilution.

In some embodiments, concentrations of the above-listed surfactants that, in addition to being lysis-effective, have low or no emission at the emission wavelengths of green emitters (500 nm to 549 nm) when in use for in situ analysis of RNA or a surrogate thereof include TRITON X-114™ surfactant at 0.05% to 1%; THESIT™ surfactant at 0.05% to 0.3%; TRITON X-100™ surfactant at 0.05% to 0.3%; NONIDET P-40™ surfactant at 0.1% to 0.3%, or a combination thereof. Commonly used labeling dyes having emission wavelengths of green emitters include FAM™ dye, FITC, JOE™ dye, Fluorescein-5-EX, succinimidyl ester, Hi FITC, Oregon Green 488, Oregon Green 514, or TET™.

In some embodiments, concentrations of the above-listed surfactants that, in addition to being lysis-effective, have low or no emission at the emission wavelengths of yellow emitters (550 nm to 584 nm) when in use for in situ analysis of RNA or a surrogate thereof include TRITON X-114™ surfactant at 0.05% to 1%; THESIT™ surfactant at 0.05% to 0.3%; TRITON X-100™ surfactant at 0.05% to 0.3%; NONIDET P-40™ surfactant at 0.1% to 0.3%, or a combination thereof. Commonly used labeling dyes having emission wavelengths of yellow emitters include CYANINE™ 3, HEX™, NED™, 5-TAMRA™, Rhodamine, or VIC®.

In some embodiments, concentrations of the above-listed surfactants that, in addition to being lysis-effective, have low or no emission at the emission wavelengths of orange emitters (585 nm to 615 nm) when in use for in situ analysis of RNA or a surrogate thereof include TRITON X-114™ surfactant at 0.05% to 1%; THESIT™ surfactant at 0.05% to 0.3%; TRITON X-100™ surfactant at 0.05% to 0.3%; NONIDET P-40™ surfactant at 0.1% to 0.3%, or a combination thereof. Commonly used labeling dyes having emission wavelengths of orange emitters include CYANINE™ 3.5, Lissamine Rhodamine, ROX™, CAL FLUOR-ORANGE™ or R-Phycoerythrin-TEXAS RED®.

A polypeptide having deoxyribonuclease activity: A polypeptide having deoxyribonuclease activity is present in certain lysis mixtures as set forth in embodiments herein where RNA is to be detected. The polypeptide having deoxyribonuclease activity is dependent upon cations such as $Ca^{++}$ or $Mg^{++}$ for stability and activity. In the case where a polypeptide having deoxyribonuclease activity is obtained with a cation already present, which is commonly the case, additional cations are not needed in the lysis mixture. In the case where a polypeptide having deoxyribonuclease activity is obtained lacking cations, exogenous cations are added to the lysis mixture. A polypeptide having deoxyribonuclease activity can be DNase I or Nuclease BAL-31, both of which are $Ca^{++}$ and $Mg^{++}$-dependent; or exonuclease I, exonuclease III, Lambda exonuclease, CviKI-1 endonuclease, or McrBC endonuclease, all of which are $Mg^{++}$-dependent, or an enzymatically active mutant or variant thereof. A polypeptide having deoxyribonuclease activity can be present in the lysis mixture from 100 U/ml to 600 U/ml in some embodiments and, for other embodiments, about 200 U/ml, about 300 U/ml, about 400 U/ml, about 500 U/ml or any range of concentrations therebetween.

Substantially free of a cation chelator: In general, the lysis mixtures for RNA sample preparation processes are substantially free of a cation chelator. A common cation chelator, such as EDTA, was described as interfering with deoxyribonuclease activity at a concentration of 1 mM in U.S. patent application Ser. No. 12/122,274. Therefore, lysis mixtures provided herein for RNA sample preparation are substantially free of a cation chelator, have less than about 0.1 mM cation chelator, have less than about 0.2 mM cation chelator, have less than about 0.5 mM or have less than 1 mM cation chelator.

Optional Lysis Mixture ingredients: In some embodiments, a calcium salt is present in the lysis mixture in concentrations ranging from 0 mM to 2.5 mM for stabilizing a deoxyribonuclease. The calcium salt can be any calcium salt that provides such function and can be calcium chloride, calcium bromide, calcium acetate, calcium formate, calcium sulfate, or calcium phosphate, for example. In certain embodiments, the calcium salt is $CaCl_2$ and the $CaCl_2$ is present at about 0.1 mM, 0.2 mM, 0.5 mM, 1.0 mM, or 2.0 mM or any range of concentrations therebetween. In some embodiments, $MgCl_2$ is present in the lysis solution in concentrations ranging from 0 mM to 2.5 mM. In certain embodiments, the $MgCl_2$ is present at about 0.5 mM, 1.0 mM, 1.5 mM, 2.0 mM, or 2.5 mM or any range of concentrations therebetween. Certain assays such as short tandem repeat detection assays use lower concentrations of $MgCl_2$ such as about 0.5 mM.

In some embodiments, the lysis mixture comprises at least one reducing agent. Use of reducing agents is well known by those of ordinary skill in the art. Exemplary reducing agents include dithiothreitol, β-mercaptoethanol, dithioerythritol, or combinations thereof.

In some embodiments, addition of a reducing agent at a final concentration of about 0.01 mM in the lysis mixture together with addition to the stop solution (as discussed below) improves cycle threshold values.

In some embodiments, the lysis mixture further comprises at least one additional catabolic enzyme. For example, a glycoside hydrolase such as amylase, lysozyme or cellulase can be included for degradation of polysaccharides, or lipase may be included for degradation of lipids, or a combination thereof may be used. In such cases, it may be necessary to balance the concentration, reaction conditions, or timing of addition of one or more catabolic enzymes, in order to prevent degradation of the at least one additional catabolic enzyme by the protease. Such reaction optimization is well within the skill of those of ordinary skill in the art in light of the teachings herein.

75. Exemplary non-limiting embodiments of lysis mixtures are prepared by obtaining stock solutions of 1M Tris-base pH 8.0, 1M $MgCl_2$, 1M $CaCl_2$, 1M DTT, proteinase K at 20 mg/ml, 20% TRITON X-114™ and nuclease-free water. Stock solutions are diluted to form a lysis solution of Tris pH 8.0, 10 mM; $MgCl_2$, 0.5 mM; $CaCl_2$, 0.5 mM; a reducing agent such as DTT, β-mercaptoethanol or dithioerythritol, 0.01 mM; proteinase K, 100 ug/ml; and TRITON X-114™, 0.1%, in nuclease free water. The pH is adjusted to pH 7.8+/− 0.1 with HCl at a temperature of 19° C.-25° C. (a range of pH values is about pH 7.5 to about pH 8.2). The lysis solution can be stored at −20° C., at 4° C., and has been found to be stable at 25° C. for one year. In some embodiments, lysis can be carried out in a 50 uL volume at a pH of about 7.8.

Stop Mixture: In some embodiments, a stop mixture comprises a cation chelator effective to inactivate the polypeptide having deoxyribonuclease activity of the lysis mixture, an inhibitor of proteinase K as described above, and generally, a stop mixture comprises a Tris-base or Tris-Cl buffer at about pH 8. For analysis embodiments by RT-PCR, the stopped mixture is compatible with reverse transcriptase and DNA polymerase reaction conditions. A stopped mixture can be included in such reactions up to 45% or up to 65% or more of the RT or PCR reaction volume depending upon the concentrations of the various components.

A cation chelator effective to inactivate the polypeptide having deoxyribonuclease activity of the stop mixture: For embodiments where the polypeptide having deoxyribonuclease activity is dependent upon calcium ions for stability and activity, the cation chelator comprises a calcium chelator such as EGTA, EDTA, or citrate, for example. For embodiments where the polypeptide having deoxyribonuclease activity is dependent upon magnesium ions for stability and activity, the cation chelator comprises a magnesium chelator such as EDTA, for example. Of course, divalent cation chelators bind a variety of divalent cations and overlap in specificity for divalent cations is expected. Cation chelators include EGTA, ethylenediamine tetraacetic acid (EDTA), sodium citrate, cation exchange beads such as SP SEPHAROSE™ beads (GE Healthcare), 1,10-phenanthroline, tetrakis-(2-pyridylmethyl)ethylenediamine (TPEN), 1,2-bis(2-aminophenoxy)ethane-N,N,N',N'-tetraacetic acid (BAPTA), or a combination thereof. EGTA inhibits DNase I at $\geq 4$ mM and is compatible with RT-PCR.

Optional Stop Mixture Ingredients: In some embodiments, the stop mixture comprise one or more ribonuclease inhibitors such as placental ribonuclease inhibitor protein (RIP, Promega, Madison, Wis.) at about 0.2 U/uL to about 0.002 U/ul, SUPERase-In™ (protein-based inhibitor for RNase A, B, C, 1, and T1, Catalog No. AM2694, Applied Biosystems), RNase inhibitor (a recombinant human placental protein having inhibitory activity for neutral pancreatic RNase A-type enzymes, Catalog No. AM2682, Applied Biosystems) and anti-RNase A (protein-based inhibitor for RNase A, Catalog No. AM2690, Applied Biosystems). The addition of RIP reduces PCR cycle threshold values at 30 min for both 5000 and 100,000 cell samples. Final RIP concentration (0.2 U/ul, after addition to lysate; 2.2 U/uL in the stop solution) helps prevent RNA degradation, particularly if the lysate is allowed to sit at room temperature for longer than about 20 minutes.

As recited supra, addition of a reducing agent to the stop solution at 0.11 mM improved cycle threshold results for PCR at 10 minutes post-stop. A reducing agent may be used in the stop solution at about 0.01 mM to about 1.1 mM. While not wanting to be bound by theory, a reducing agent is provided for the stop solution to improve functionality and stability of ribonuclease inhibitor protein (RIP).

A stop reaction is incubated for up to 2 minutes. After about 20 minutes, PCR cycle threshold values increase very gradually. In some embodiments, a stopped mixture has a pH of 7.3-7.8 as a result of the protease inhibition reaction.

Use of Proteinase K Inhibitors in Sample Preparation for RNA or DNA Analyses: Exemplary non-limiting embodiments of lysis solutions are prepared by obtaining stock solutions of 1M Tris-base pH 8.0, 1M $MgCl_2$, 1M $CaCl_2$, 1M DTT, proteinase K at 20 mg/ml, 20% TRITON X-114™ surfactant and nuclease-free water. Stock solutions are diluted to form a lysis solution of Tris pH 8.0, 10 mM; $MgCl_2$, 0.5 mM; $CaCl_2$, 0.5 mM; a reducing agent such as DTT, β-mercaptoethanol or dithioerythritol, 0.01 mM; protease such as proteinase K, 100 ug/ml; and TRITON X-114™ surfactant, 0.1%, in nuclease-free water. The pH is adjusted to pH 7.8+/−0.1 with HCl at a temperature of 19° C.-25° C. (a range of pH values is about 7.5 to 8.2). The lysis solution can be stored at −20° C., at 4° C., and has been found to be stable at 25° C. for one year.

An exemplary lysis mixture is prepared by combining the lysis solution with a deoxyribonuclease such as DNase I at a concentration of 300 U/ml (a range of 100 U/ml-600 U/ml can be used) for those embodiments in which it is desired to remove DNA. In certain embodiments, the volume of deoxyribonuclease added is less than about 1% of the volume of the final lysis reaction. Lysis can be carried out in a 50 uL volume at a pH of 7.8.

Exemplary embodiments of a stop mixture include a protease inhibitor comprising MeOSuc-AlaAlaProPhe-$CH_2Cl$ (SEQ ID NO:5), MeOSuc-AlaProAlaLeu-$CH_2Cl$ (SEQ ID NO:4), MeOSuc-AlaAlaAlaProLeu-$CH_2Cl$ (SEQ ID NO:7), MeOSuc-AlaAlaAlaProPhe-$CH_2Cl$ (SEQ ID NO:9), or a combination thereof; and a divalent cation chelator that, by chelating divalent cations of the lysis mixture, provides for inactivation of the deoxyribonuclease of the lysis mixture. Therefore a lysis mixture and a stop mixture are tailored to work together.

Stock solutions for an exemplary stop mixture include a protease inhibitor such as MeOSuc-AAPF-$CH_2Cl$ (SEQ ID NO:5) in DMSO (100 mM), 1M Tris-base pH 8.3, a cation chelator such as 200 mM EGTA, a reducing agent such as 1M DTT and nuclease free water. An exemplary stop mixture for use with proteinase K and DNase I includes MeOSuc-AAPF-$CH_2Cl$ (SEQ ID NO:5), 0.5 mM; Tris pH 8.3, 11 mM; EGTA, 88 mM; RNase Inhibitor such as RIP, 2.2 U/ul; and DTT, 0.11 mM in nuclease free water. The pH is adjusted to 8.0+/−0.1 (at 19° C.-25° C.) with HCl or KOH as needed. For this exemplary embodiment, 5 uL of stop solution is added to 50 uL of lysis mixture to form a stopped mixture.

Certain embodiments of the processes for preparing a sample for nucleic acid analysis are carried out as follows. DNase I is mixed with lysis solution and the resultant lysis mixture is stored on ice. For 1-$10^6$ cultured mammalian cells, cells are pelleted (~800×g for 5 min), the media is removed and the cells are washed with 50 uL of 1×PBS and re-pelleted. The supernatant is removed. Adhered cells in 96- or 384-well plates (1 to $10^6$ cells) can also be used with this procedure. No centrifugation is required since the cells remain adhered to the plate throughout the washing procedure.

Lysis mixture (50 ul) is added to the pellet and the pellet is resuspended by pipetting. The lysis reaction is incubated for 5 minutes at room temperature (19° C.-25° C.) or for about 8 minutes for miRNA sample preparation embodiments, also at room temperature. Stop solution (5 ul) is added directly into each lysis reaction, mixed 5× by pipetting, and incubated for 2 minutes at room temperature (19° C.-25° C.). The stopped lysate is ready for downstream nucleic acid analysis, detection and/or amplification and is used within about 20 minutes for such a downstream procedure or is frozen for later use.

A 5-minute lysis time, a 2-minute stop time, and mixing 5× with a pipette are provided for some embodiments of nucleic acid preparation methods of the present teachings. An 8-minute lysis time, a 2-minute stop time, and mixing 5× with a pipette are provided for embodiments of miRNA nucleic acid preparation methods of the present teachings. Temperatures between 16° C. and 28° C. are provided for certain embodiments of isothermal preparation methods. Washing with 50 uL PBS or media (without fetal bovine serum) is acceptable prior to lysis.

Nucleic acid analysis, detection and/or amplification can include a reverse transcription step, a real-time PCR reaction, and/or an RNA transcription step comprising use of an RNA polymerase. The sample preparation process provided by teachings herein provides components that minimally interfere with enzymatic activity and detection methods.

Sample preparation processes as provided by teachings herein are compatible with a large number of cell lines such as adherent cell lines and suspension cell lines, for example, HeLa, HepG2, Primary Hepatocytes, SK-N-AS, SK-N-SH, U-87 MG, ME-180, A549, Jurkat, PC-12, PT-K75, NIH/3T3, Raji, HEK-293, COS-7, CHO-K1, NCI-H460, DU 145, K562, U-2 OS, Huh-7, Neuro 2A, and BJ cell lines.

Sample preparation processes of embodiments herein are provided for microRNA quantitation and profiling without RNA isolation. Cells (up to $10^5$-$10^6$) are washed in phosphate-buffered saline and lysed for 8 minutes at room temperature. DNase treatment can be performed concurrently. Lysis is terminated at room temperature for two minutes with stop solution as described above. All of the small RNA species present in a cell are available for analysis since the samples are processed directly.

Sample preparation processes of embodiments herein also provide the ability to distinguish between highly homologous mature miRNA targets for accurate miRNA expression analysis.

Sample preparation processes of embodiments herein also provide methods for analyzing effects of siRNAs for RNA interference activity.

Sample preparation processes of embodiments herein also provide methods for single nucleotide polymorphism (SNP) detection.

Detection of DNA, RNA or a surrogate thereof: Embodiments of detecting DNA, RNA or a surrogate thereof in a stopped mixture as provided herein includes detection using emission by an emitter that is representative of the RNA or DNA in the stopped mixture.

In some embodiments, RNA of a stopped mixture as provided by teachings herein is detected in situ by adding or mixing at least a portion of the stopped mixture with a composition comprising reverse transcriptase to form a reverse transcriptase reaction mixture. A reverse transcription reaction provides a surrogate of the RNA that can be detectable. Any reverse transcriptase known to those of ordinary skill in the art can be used such as, for example, MMLV-RT (murine maloney leukemia virus-reverse transcriptase), avian myelogenous virus reverse transcriptase (AMV-RT), human immunodeficiency virus (HIV)-RT and the Tth DNA polymerase which has reverse transcriptase activity if $Mn^{++}$ is provided.

A positive control for detection of RNA or DNA can be a non-homologous RNA random sequence such as XENO™ RNA (Applied Biosystems, Foster City, Calif.). A control for qPCR can be a β-actin probe/primer set, also available from Applied Biosystems, for example. The positive control can be mixed with the stop solution and therefore is added at the time of adding stop solution to a sample.

Amplification: As used herein, "amplification" or "amplify" and the like refers to a process that results in an increase in the copy number of a molecule or set of related molecules. As the term applies to a stopped mixture herein, amplification means the production of multiple copies of the target nucleic acid, a surrogate of a target nucleic acid, or a portion thereof. Amplification can encompass a variety of chemical and enzymatic processes such as a polymerase chain reaction (PCR), a strand displacement amplification reaction, a transcription mediated amplification reaction, or a nucleic acid sequence-based amplification reaction, for example. Following at least one amplification cycle, the amplification products can be detected or can be separated from at least one other component of the amplification mixture based on their molecular weight or length or mobility prior to detection.

Polymerase Chain Reaction: PCR includes introducing a molar excess of two or more extendable oligonucleotide primers to a reaction mixture comprising the stopped mixture where the primers hybridize to opposite strands of a DNA, RNA or RNA surrogate. The reaction mixture is subjected to a program of thermal cycling in the presence of a DNA polymerase, resulting in the amplification of the DNA or RNA surrogate sequence flanked by the primers. Reverse transcriptase PCR is a PCR reaction that uses an RNA template and a reverse transcriptase, or a polypeptide having reverse transcriptase activity, to first generate a single stranded DNA molecule prior to the multiple cycles of DNA-dependent DNA polymerase primer elongation as cited above. Methods for a wide variety of PCR applications are widely known in the art, and described in many sources, for example, Ausubel et al. (eds.), Current Protocols in Molecular Biology, Section 15, John Wiley & Sons, Inc., New York (1994).

Criteria for designing sequence-specific primers are well known to persons of ordinary skill in the art. Detailed descriptions of primer design that provide for sequence-specific annealing can be found, among other places, in Diffenbach and Dveksler, PCR Primer, A Laboratory Manual, Cold Spring Harbor Press, 1995, and Kwok et al. (*Nucl. Acid Res.* 18:999-1005, 1990). The sequence-specific portions of the primers are of sufficient length to permit specific annealing to complementary sequences, as appropriate. A primer does not need to have 100% complementarity with a primer-specific portion for primer extension to occur. Further, a primer can be detectably labeled such that the label is detected by spectroscopy. A primer pair is sometimes said to consist of a "forward primer" and a "reverse primer," indicating that they are initiating nucleic acid polymerization in opposing directions from different strands of a duplex template.

In some embodiments, a primer as set forth herein can comprise a universal priming sequence. The term "universal primer" refers to a primer comprising a universal sequence that is able to hybridize to all, or essentially all, potential target sequences in a multiplexed reaction. The term "semi-universal primer" refers to a primer that is capable of hybridizing with more than one (e.g., a subset), but not all, of the potential target sequences in a multiplexed reaction. The terms "universal sequence," "universal priming sequence" or "universal primer sequence" or the like refer to a sequence contained in a plurality of primers, where the universal priming sequence that is found in a target is complementary to a universal primer.

For real time PCR, a passive reference dye, such as ROX™ dye, can be included in PCR reactions to provide an internal reference to which the reporter-dye signal can be normalized during data analysis. Normalization can be accomplished using Applied Biosystems' Sequence Detection System (SDS) software.

In certain embodiments, single-stranded amplification products can be generated by methods including, without limitation, asymmetric PCR, asymmetric reamplification, nuclease digestion, and chemical denaturation. For example, single-stranded sequences can be generated by combining at least one first primer or at least one second primer from a primer set, but not both, in an amplification reaction mixture, or by transcription, for example, when a promoter-primer is used in a first amplification mixture, a second amplification mixture, or both.

Polymerase: The term "polymerase," as used herein, refers to a polypeptide that is able to catalyze the addition of nucleotides or analogs thereof to a nucleic acid in a template dependent manner, for example, the addition of deoxyribonucleotides to the 3'-end of a primer that is annealed to a nucleic acid template during a primer extension reaction. Nucleic acid polymerases can be thermostable or thermally degradable. Suitable thermostable polymerases include, but are not limited to, polymerases isolated from *Thermus aquaticus, Thermus thermophilus, Pyrococcus woesei, Pyrococcus furiosus, Thermococcus litoralis,* and *Thermotoga maritima.* Suitable thermodegradable polymersases include, but are not limited to, *E. coli* DNA polymerase I, the Klenow fragment of *E. coli* DNA polymerase I, T4 DNA polymerase, T5 DNA polymerase, T7 DNA polymerase, and others. Examples of other polymerizing enzymes that can be used in the methods described herein include but are not limited to T7, T3, SP6 RNA polymerases; and AMV, M-MLV and HIV reverse transcriptases.

Commercially available polymerases include, but are not limited to AMBION'S SUPERTAQ®, TAQFS®, AMPLITAQ® CS (Applied Biosystems), AMPLITAQ® FS (Applied Biosystems), KENTAQ1® (AB Peptide, St. Louis, Mo.), TAQUENASE® (Scien Tech Corp., St. Louis, Mo.), THERMOSEQUENASE® (Amersham), Bst polymerase, READER™ Taq DNA polymerase, VENT® DNA polymerase, VENT$_R$® DNA Polymerase, VENT$_R$® (exo⁻) polymerase and DEEPVENT® DNA polymerase, (all VENT® polymerases can be obtained from New England Biolabs), PFUTurbo™ DNA polymerase (Stratagene), Pwo polymerase, Tth DNA polymerase, KlenTaq-1 polymerase, SEQUENASE™ 1.0 DNA polymerase (Amersham Biosciences), SEQUENASE™ 2.0 DNA polymerase (United States Biochemicals), and an enzymatically active mutant and variant thereof.

Descriptions of DNA polymerases can be found in, among other places, Lehninger *Principles of Biochemistry*, 3d ed., Nelson and Cox, Worth Publishing, New York, N.Y., 2000, particularly Chapters 26 and 29; Twyman, *Advanced Molecular Biology: A Concise Reference*, Bios Scientific Publishers, New York, N.Y., 1999; Ausubel et al., *Current Protocols in Molecular Biology*, John Wiley & Sons, Inc., including supplements through May 2005 (hereinafter "Ausubel et al."); Lin and Jaysena, *J. Mol. Biol.* 271:100-11, 1997; Pavlov et al., *Trends in Biotechnol.* 22:253-60, 2004; and *Enzymatic Resource Guide: Polymerases*, 1998, Promega, Madison, Wis.

In various detection embodiments, amplification is optionally followed by additional steps, for example, but not limited to, labeling, sequencing, purification, isolation, hybridization, size resolution, expression, detecting and/or cloning. In certain embodiments, one or both PCR primers can comprise a label, such as, for example, a fluorophore. A label can facilitate detection of an amplification product comprising a labeled PCR primer. In various detection embodiments, following the PCR, biotinylated strands can be captured, separated, and detected.

Multiplex Assays: The term "multiplex assays" refers to PCR reactions that use more than two primers in a single reaction and at the same time so that more than one different amplified product is produced and detected. For example, more than two pair of amplification primers are contacted at the same time and/or in the same solution. Several target RNAs or DNAs can be detected simultaneously using multiplex assays. A multiplex reaction can also include a multiplicity of singleplex PCR reactions run in parallel, e.g., the TAQMAN® Low Density Array (TLDA). Sample preparation processes described herein have been demonstrated to be compatible with multiplex assays.

Real-time PCR: As used herein, "real-time PCR" refers to the detection and quantitation of a DNA, a RNA or a surrogate thereof in a sample. In some embodiments, the amplified segment or "amplicon" can be detected using a 5'-nuclease assay, particularly the TAQMAN® assay as described by e.g., Holland et al. (*Proc. Natl. Acad. Sci. USA* 88:7276-7280, 1991); and Heid et al. (*Genome Research* 6:986-994, 1996). For use herein, a TAQMAN® nucleotide sequence to which a TAQMAN® probe binds can be designed into the primer portion, or known to be present in a RNA or a DNA of a sample.

"$T_m$" refers to the melting temperature (temperature at which 50% of the oligonucleotide is a duplex) of an oligonucleotide determined experimentally or calculated using the nearest-neighbor thermodynamic values of Breslauer et al. (*Proc. Natl. Acad. Sci. USA* 83:3746 3750, 1986) for DNA or Freier et al. (*Proc. Natl. Acad. Sci. USA* 83:9373-9377, 1986) for RNA. In general, the $T_m$ of the TAQMAN® probe is about 10 degrees above the $T_m$ of amplification primer pairs. Amplification primer sequences and double dye-labeled TAQMAN® probe sequences can be designed using PRIMER EXPRESS™ (Version 1.0, Applied Biosystems, Foster City, Calif.) or mFOLD™ software (now UNIFold™) (IDT, San Jose, Calif.).

When a TAQMAN® probe is hybridized to DNA, RNA or a surrogate thereof, the 5'-exonuclease activity of a thermostable DNA-dependent DNA polymerase such as SUPERTAQ® (a Taq polymerase from *Thermus aquaticus*, Ambion, Austin, Tex.) digests the hybridized TAQMAN® probe during the elongation cycle, separating the fluor dye from the quencher. The reporter fluor dye is then free from the quenching effect of the quencher moiety resulting in a decrease in FRET and an increase in emission of fluorescence from the fluor dye. One molecule of reporter dye is generated for each new molecule synthesized, and detection of the free reporter dye provides the basis for quantitative interpretation of the data. In real-time PCR, the amount of fluorescent signal is monitored with each cycle of PCR. Once the signal reaches a detectable level, it has reached the "threshold or cycle threshold (Ct)." A fluorogenic PCR signal of a sample can be considered to be above background if its Ct value is at least 1 cycle less than that of a no-template control sample. The term "Ct" represents the PCR cycle number when the signal is first recorded as statistically significant. Thus, the lower the Ct value, the greater the concentration of nucleic acid target. In the TAQMAN® assay, typically each cycle almost doubles the amount of PCR product and therefore, the fluorescent signal should double if there is no inhibition of the reaction and the reaction was nearly 100% efficient with purified nucleic acid. Certain systems such as the ABI 7700 and 7900HT Sequence Detection Systems (Applied Biosystems, Foster City, Calif.) conduct monitoring during each thermal cycle at a pre-determined or user-defined point.

Detection method embodiments using a TAQMAN® probe sequence comprise combining the stopped mixture or the reverse transcribed mixture with PCR reagents, including a primer set having a forward primer and a reverse primer, a DNA polymerase, and a fluorescent detector oligonucleotide TAQMAN® probe, as well as dNTP's and a salt, to form an amplification reaction mixture; subjecting the amplification reaction mixture to successive cycles of amplification to generate a fluorescent signal from the detector probe; and quantitating the nucleic acid presence based on the fluorescent signal cycle threshold of the amplification reaction.

Protocols and reagents for carrying out further 5'-nuclease assays are well known to one of skill in the art, and are described in various sources. For example, 5'-nuclease reactions and probes are described in U.S. Pat. No. 6,214,979 issued Apr. 10, 2001; U.S. Pat. No. 5,804,375 issued Sep. 8, 1998; U.S. Pat. No. 5,487,972 issued Jan. 30, 1996; and U.S. Pat. No. 5,210,015 issued May 11, 1993, all to Gelfand et al.

In various embodiments, a detection method can utilize any probe that can detect a nucleic acid sequence. In some configurations, a detection probe can be, for example, a TAQMAN® probe described supra, a stem-loop molecular beacon, a stemless or linear beacon, a PNA MOLECULAR BEACON™, a linear PNA beacon, non-FRET probes, SUNRISE®/AMPLIFLUOR® probes, stem-loop and duplex SCORPION™ probes, bulge loop probes, pseudo knot probes, cyclicons, MGB ECLIPSE™ probe, a probe complementary to a ZIPCODE™ sequence, hairpin probes, peptide nucleic acid (PNA) light-up probes, self-assembled nanoparticle probes, and ferrocene-modified probes as known by one of ordinary skill in the art. A detection probe having a sequence complementary to a detection probe hybridization sequence, such as a ZIPCODE™ sequence, a fluorphore and a mobility modifier can be, for example, a ZIPCHUTE™ probe supplied commercially by Applied Biosystems (Foster City, Calif.).

Label or Reporter: A "label" or "reporter," as used herein, refers to a moiety or property that allows the detection of that with which it is associated and, for use herein, has emission spectra at between and including 300 nm to 750 nm. In certain embodiments, the emission spectra is at less than about 499 nm such as for blue emitters such as certain Alexa Fluor emitters, Cascade Blue, and Pacific Blue; at 500 nm to 549 nm emitters such as for green emitters such as certain Alexa Fluor emitters, BODIPY FL, fluorescein (FITC), CYANINE™ 2 dye, Catskill Green, 5-FAM™ dye, 6-FAM™ dye, succinimidyl ester, JOE™ dye, MFP488, the Oregon Green emitters and TET™ dye; at 550 nm to 584 nm emitters such as yellow emitters such as certain Alexa Fluor emitters, CYANINE™ 3 dye, HEX™ dye, NED™ dye, R-Phycoerythrin (R-PE), 5-TAMRA™ dye, TRITC (Rhodamine), and VIC® dye; at 585 nm to 615 nm emitters such as orange emitters such as certain Alexa Fluor emitters, CYANINE™ 3.5 dye, Lissamine Rhodamine, ROX™ dye, and R-Phycoerythrin-TEXAS RED® dye; and at 616 nm to 700 nm emitters such as red emitters such as certain Alexa Fluor emitters, CYANINE™ 5 dye, Quantum Red, Rodamine Red-X, and TEXAS RED® dye.

The label can be attached covalently or non-covalently to a DNA product, to a RNA product, or to a surrogate thereof such as an amplicon thereof. Commonly used labels include dyes that are negatively charged, such as dyes of the fluorescein family including, e.g. FAM™ dye, HEX™ dye, TET™ dye, JOE™ dye, NAN and ZOE; or dyes that are neutral in charge, such as dyes of the rhodamine family including, e.g., TEXAS RED® dye, ROX™ dye, R110, R6G, and TAMRA™ dye; or dyes that are positively charged, such as dyes of the CYANINE™ family including e.g., Cy™ 2 dye, Cy™ 3 dye, Cy™ 5 dye, Cy™ 5.5 dye and Cy™ 7 dye. FAM™ dye, HEX™ dye, TET™ dye, JOE™ dye, NAN, ZOE, ROX™ dye, R110, R6G, and TAMRA™ dyes are available from, e.g., Applied Biosystems (Foster City, Calif.) or Perkin-Elmer, Inc. (Wellesley, Mass.); TEXAS RED® dye is available from, e.g., Molecular Probes, Inc. (Eugene, Oreg.); and Cy™ 2 dye, Cy™ 3 dye, Cy™ 5 dye, Cy™ 5.5 dye and Cy™ 7 dye, and are available from, e.g., Amersham Biosciences Corp. (Piscataway, N.J.). In certain amplification embodiments, the fluorescer molecule is a fluorescein dye and the quencher molecule is a rhodamine dye.

A label or reporter can comprise both a fluorophore and a fluorescence quencher. The fluorescence quencher can be a fluorescent fluorescence quencher, such as the fluorophore TAMRA™ dye, or a non-fluorescent fluorescence quencher (NFQ), for example, a combined NFQ-minor groove binder (MGB) such as an MGB ECLIPSE™ minor groove binder supplied by Epoch Biosciences (Bothell, Wash.) and used with TAQMAN™ probes (Applied Biosystems, Foster City, Calif.). The fluorophore can be any fluorophore that can be attached to a nucleic acid, such as, for example, FAM™ dye, HEX™ dye, TET™ dye, JOE™ dye, NAN, ZOE, TEXAS RED® dye, ROX™ dye, R110, R6G, TAMRA™ dye, Cy™ 2 dye, Cy™ 3 dye, Cy™ 5 dye, Cy™ 5.5 dye and Cy™ 7 dye as cited above as well as VIC® dye, NED™ dye, LIZ® dye, ALEXA, Cy™ 9 dye, and dR6G.

Further examples of labels include black hole quenchers (BHQ) (Biosearch), Iowa Black (IDT), QSY quencher (Molecular Probes), and Dabsyl and Dabcel sulfonate/carboxylate Quenchers (Epoch).

Labels can also comprise sulfonate derivatives of fluorescein dyes, phosphoramidite forms of fluorescein, phosphoramidite forms of CY™ 5 dye (available for example from Amersham), and intercalating labels such as ethidium bromide, SYBR™ Green I dye and PICOGREEN™ dye (Molecular Probes). Generally, an intercalating label is a molecule that reversibly inserts between two other molecules (or groups) such as between the bases of DNA.

In various embodiments, qPCR reactions can include master mixes such as the TAQMAN® Gene Expression Master Mix, TAQMAN® Universal PCR Master Mix, TAQMAN® Fast Universal PCR Master Mix, Power SYBR® Green PCR Master Mix, Fast SYBR® Green Master Mix, TAQMAN® RNA-to-$C_T$™ 1-Step Kit, and the Power SYBR® Green RNA-to-$C_T$™ 1-Step Kit, for example, all from Applied Biosystems.

In various embodiments, detection of emission such as fluorescence can be by any method known to skilled artisans, and can include, for example, real time detection for PCR or end point detection. Detection of fluorescence, for example, can be qualitative or quantitative. Quantitative results can be obtained, for example, with the aid of a fluorimeter, for example a fluorimeter as part of an integrated nucleic acid analysis system, such as, for example, an Applied Biosystems ABI PRISM™ 7900HT Sequence Detection System. Furthermore, quantitative results can be obtained in some configurations using a real-time PCR analysis. Some non-limiting examples of protocols for conducting fluorogenic assays such as TAQMAN® assays, including analytical methods for performing quantitative assays, can be found in publications such as, for example, "SNPLEX™ Genotyping System 48-plex", Applied Biosystems, 2004; "User Bulletin #2 ABI PRISM™ 7700 Sequence Detection System," Applied Biosystems 2001; "User Bulletin #5 ABI PRISM™ 7700 Sequence Detection System," Applied Biosystems, 2001; and "Essentials of Real Time PCR," Applied Biosystems (Foster City, Calif.). Fluorogenic PCR assays used in some configurations of the present teachings can be performed using an automated system, such as, for example, an ABI 7700 Sequence Detection System (Applied Biosystems).

In some embodiments, detection can be achieved using microarrays or bead arrays and related software, such as the Applied Biosystems Array System with the Applied Biosystems 1700 Chemiluminescent Microarray Analyzer, and other commercially available array systems available from Affymetrix, Agilent, and Illumina, among others (see also Gerry et al., *J. Mol. Biol.* 292:251-62, 1999; De Bellis et al., *Minerva Biotec* 14:247-52, 2002; and Stears et al., *Nat. Med.* 9:140-45, including supplements, 2003).

Further method embodiments for detection of DNA, RNA, or a surrogate thereof comprise use of a promoter sequence or a complement thereof and the method includes combining the DNA, RNA, or a surrogate thereof with PCR reagents, including at least one primer set and a DNA polymerase, to form a first amplification reaction mixture subjecting the first amplification reaction mixture to at least one cycle of amplification to generate a first amplification product comprising the promoter sequence; combining the first amplification product with an RNA polymerase and a ribonucleoside triphosphate solution comprising at least one of rATP, rCTP, rGTP, rUTP, or aminoallyl-rUTP to form a transcription reaction mixture;

incubating the transcription reaction mixture under appropriate conditions to generate an RNA transcription product; and detecting presence of the target nucleic acid by detection of the RNA transcription product or a portion thereof. In certain embodiments, the polymerase is reverse transcriptase.

Exemplary RNA polymerases include T7, T3, or SP6 RNA polymerase and exemplary promoters include the T7, T3, or SP6 promoters. The RNA transcription product or a portion thereof can be detected using, for example, the aminoallyl-rUTP which is available for coupling to a succinimide ester label for detection.

Enzymatically Active Mutants or Variants Thereof: The term "enzymatically active mutants or variants thereof" when used in reference herein to an enzyme such as a protease, deoxyribonuclease, a polymerase or the like, refers to a polypeptide derived from the corresponding enzyme that retains at least some of the desired enzymatic activity. Enzymatically active mutants or variants include, for example, fragments, recombinantly expressed fragments, naturally-occurring mutants, mutants generated using mutagens, genetically engineered mutants, mutants due to amino acid insertions or deletions or due to nucleic acid nonsense, missense, or frameshift mutations, reversibly modified enzymes, splice variants, polypeptides having modifications such as altered glycosylation, disulfide bonds, hydroxyl side chains, and phosphate side chains, or crosslinking, and the like. Protocols for measuring enzymatic activity using an appropriate assay are known to one of ordinary skill in the art.

Cell lysates provided herein are useful for any method of detection of nucleic acid that uses a dye that has a detectable emission. In particular, a dye or label that fluoresces in the 500 nm to 615 nm range such as used in PCR, RT-PCR, qRT-PCR, siRNA-mediated gene knockdown, high-throughput assessment of any kind particularly in 96-well or 384-well plates is envisioned for use herein. Samples can be processed directly in culture plates, minimizing sample handling and the potential for sample loss or transfer error. The cell lysis protocol in 384-well plates is readily automated on robotic platforms. cDNA can then be synthesized directly from the lysate using the High Capacity cDNA RT Kit, or the High Capacity RNA-to-cDNA kit, and real-time PCR performed using the TAQMAN® Gene Expression Master Mix (Applied Biosystems, Foster City, Calif.) on the 7900HT Real Time PCR System. Custom libraries of Silencer® Pre-designed siRNAs and TAQMAN® Gene Expression Assays plated to specification in 96-well or 384-well plates can be obtained directly from the manufacturer (Applied Biosystems). Processes provided by the teachings herein ensure high-throughput processing, efficient use of reagents and instruments, a minimal amount of hands-on time, and accurate and reliable results.

Kits: A "kit," as used herein, refers to a combination of items for performing a sample preparation process as set forth herein. Embodiments of kits comprise, for example, lysis mixture components and stop mixture components. Lysis mixture components comprise a polypeptide having protease activity such as proteinase K, a surfactant comprising TRITON X-114™, THESIT™, TRITON X-100™, NONIDET P-40™, or a combination thereof, and a polypeptide having deoxyribonuclease activity. The lysis mixture components are substantially free of a cation chelator. Stop mixture components comprise a cation chelator, and an inhibitor of the polypeptide having protease activity comprising an alkoxysuccinyl-peptidyl-haloalkyl ketone as provided herein. Components of kits may be packaged together or separately as desired for the processes described herein.

Kit embodiments can further comprise reagents for reverse transcription, such as reverse transcriptase, a reverse primer, dNTPs or a reverse transcriptase buffer, or can further comprise reagents for PCR, such as a DNA polymerase, for example.

Embodiments of kits can further comprise a detector probe such as a 5'-nuclease probe such as a TAQMAN® probe, an RNA or a DNA control nucleic acid, reagents for sample collection, an RNA polymerase or an enzymatically active mutant or variant thereof, or ribonucleotides rATP, rCTP, rGTP, rUTP, or aminoallyl-rUTP. In certain kit embodiments, amplification primers can be attached to a solid support such as a microarray.

In some kit embodiments, an enzyme comprising reverse transcriptase activity and thermostable DNA-dependent DNA polymerase activity are the same enzyme, e.g., *Thermus* sp. ZO5 polymerase or *Thermus thermophilus* polymerase.

When components of a kit are provided in one and/or more liquid solutions, the liquid solution comprises an aqueous solution that can be a sterile aqueous solution. In some embodiments, at least one component of the kit can be provided as a dried powder. When reagents and/or components are provided as a dry powder, the powder can be reconstituted by the addition of a suitable solvent. It is envisioned that the solvent can also be provided in another container means. The container means will generally include at least one vial, test tube, flask, bottle, syringe and/or other container means, into which the solutions are placed, and in some embodiments, suitably aliquoted. The kits can also comprise a further container means for containing a sterile, pharmaceutically acceptable buffer and/or other diluent.

A kit can also include instructions for employing the kit components as well the use of any other reagent not included in the kit. Instructions can include variations that can be implemented.

Aspects of the present teachings can be further understood in light of the following examples, which should not be construed as limiting the scope of the present teachings in any way.

Example 1

Synthesis of Methoxysuccinyl Tetrapeptide Chloromethylketone Compounds

Synthesis of methoxysuccinyl tetrapeptide chloromethyl ketone compounds is as follows. Characterization and confirmation of structure were by $^1$H NMR and mass spectroscopy. The synthons were purchased from Bachem (Torrence, Calif.) and Chemimpex (Wood Dale, Ill.) and used without further purification. Methoxysuccinyl-AlaAlaProVal chloromethyl ketone was purchased from Bachem. Organic solvents were purchased from Sigma-Aldrich (St. Louis, Mo.).

Synthesis of MeOSuc-AlaAlaProPhe-CH$_2$Cl 6:

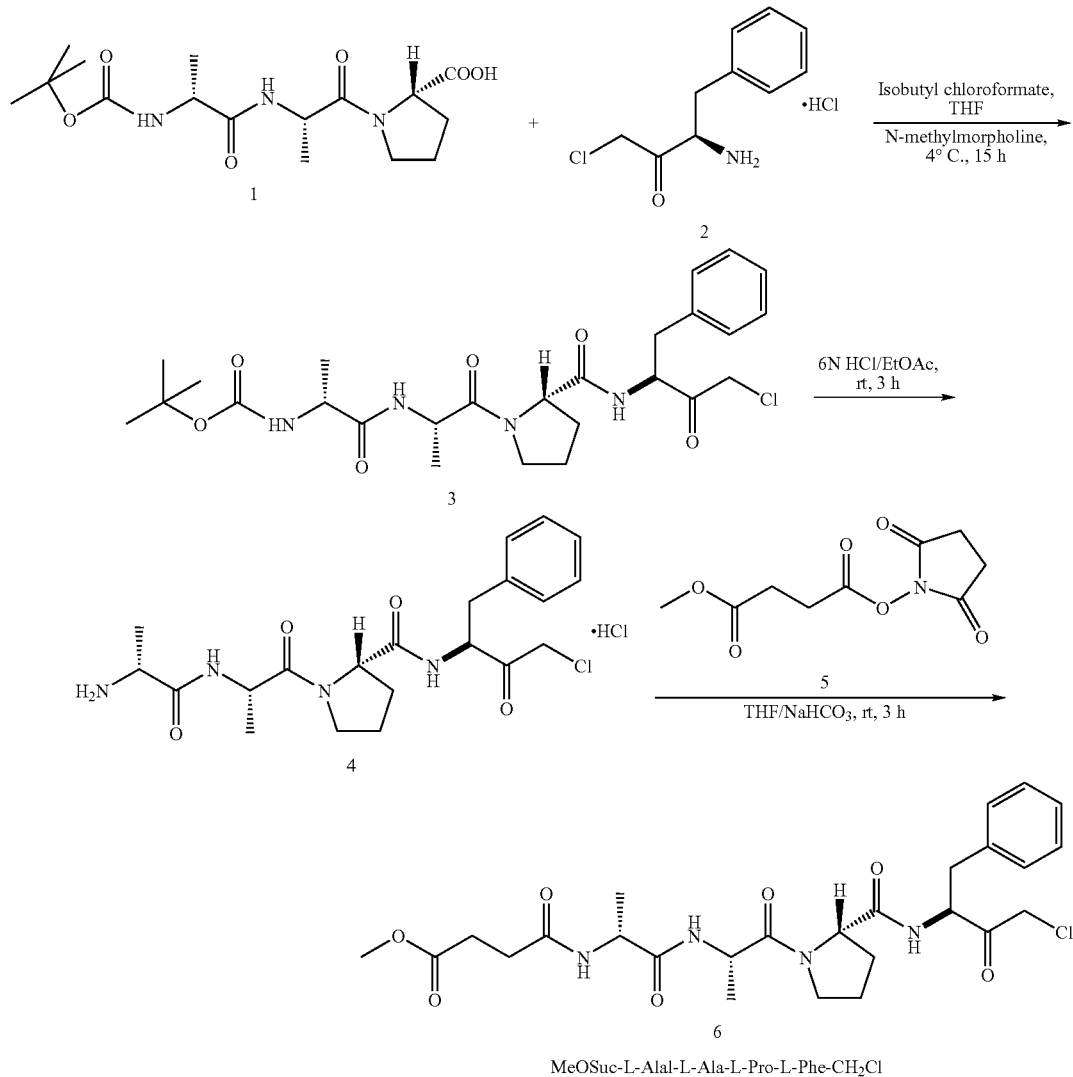

MeOSuc-L-AlaI-L-Ala-L-Pro-L-Phe-CH$_2$Cl

Preparation of Boc-AAPF-CH$_2$Cl (SEQ ID NO:5) 3: To a stirred solution of Boc-Ala-Ala-Pro-OH 1 (0.3 g, 0.84 mmol) in 10 mL of tetrahydrofuran (THF) under argon atmosphere at +4° C., isobutyl chloroformate (0.16 mL, 1.23 mmol) and N-methylmorpholine (0.37 mL, 3.37 mmol) were added and the reaction mixture was allowed to stir for 15 min. After 15 min, a solution of H-Phe-CH$_2$Cl.HCl 2 (0.26 g, 1.11 mmol) in 10 mL of THF was added by syringe over 15 min. The resulting reaction mixture was allowed to stir for 15 h and diluted with dichloromethane (DCM, 50 mL). The resulting solution was washed with 10 mL of 1N HCl, 10 mL of 5% NaHCO$_3$, and 10 mL of 2M NaCl solution. The collected organic layer was dried over MgSO$_4$, filtered and concentrated using a rotor evaporator. To the resulting residue, 50 mL hexane was added and stirred for 10 min. After stifling for 10 min, the resulting suspension was filtered and dried under vacuum for 10 min to give Boc-AAPF-CH$_2$Cl (SEQ ID NO:5) 3 (0.40 g, 89%) as a pale yellow colored solid.

Preparation of H-AAPF-CH$_2$Cl.HCl (SEQ ID NO:5) 4: To a stirred solution of Boc-AAPF-CH$_2$Cl (SEQ ID NO:5) 3 (0.38 g, 0.71 mmol) in 10 mL of ethyl acetate, 10 mL of 6N HCl was added. The resulting reaction mixture was allowed to stir at rt for 3 h. After 3 h, the resulting mixture was washed with 50 mL DCM. The collected aqueous solution was evaporated under rotor evaporator to give H-AAPF-CH$_2$Cl.HCl (SEQ ID NO:5) 4 (0.29 g, 88%) in an oil form.

Preparation of MeOSuc-AAPF-CH$_2$Cl (SEQ ID NO:5) 6: To a stirred solution of H-AAPF-CH$_2$Cl.HCl (SEQ ID NO:5) 4 (0.29 g, 0.61 mmol) in 10 mL of THF, a suspension of sodium bicarbonate (1.0 g in 1 mL water) was added and the resulting solution was allowed to stir at rt for 10 min. After 10 min, methyl succinimidosuccinate 5 (0.14 g, 0.61 mmol) was added and the resulting reaction mixture was allowed to stir at rt for 3 h. After 3 h, the reaction mixture was diluted with DCM (50 mL). The resulting organic layer was washed with water (15 mL) and brine (15 mL). The organic layer was evaporated using a rotor evaporator to give the product MeO-Suc-AAPF-CH$_2$Cl (SEQ ID NO:5) 6 (0.23 g, 70%) as a yellow colored solid. Data for MeOSuc-AAPF-CH$_2$Cl (SEQ ID NO:5) 6: $^1$H NMR (CDCl$_3$, 400 MHz) δ 7.76 (m, 2H), 7.26-7.11 (m, 5H), 6.43 (d, J=7.6 Hz, 1H), 4.78 (m, 1H), 4.64 (m, 2H), 4.49 (m, 1H), 4.10 (m, 2H), 3.72 (m, 1H), 3.65 (s, 3H), 3.56 (m, 1H), 3.11 (m, 1H), 2.95 (m, 1H), 2.59 (m, 2H), 2.47 (m, 2H), 2.14-1.93 (m, 4H), 1.35-1.19 (m, 6H); MS (m/z): 551 [M+H]+.

Synthesis of MeOSuc-AlaProAlaVal-CH$_2$Cl 11:

Preparation of MeOSuc-APAV-CH$_2$Cl (SEQ ID NO:3) 11: To a stirred solution of H-APAV-CH$_2$Cl.HCl (SEQ ID NO:3) 10 (0.36 g, 0.85 mmol) in 10 mL of THF, a suspension of sodium bicarbonate (1.0 g in 1 mL water) was added and

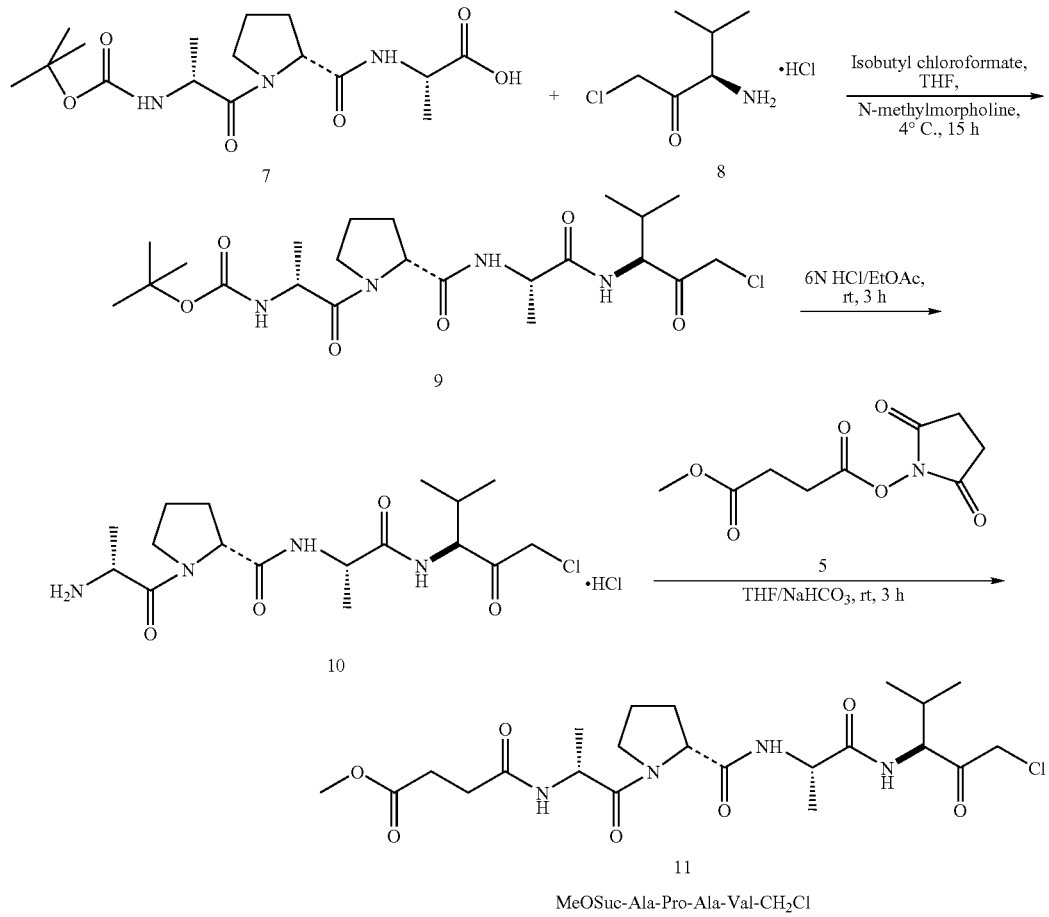

Preparation of Boc-APAV-CH$_2$Cl (SEQ ID NO:3) 9: To a stirred solution of Boc-Ala-Pro-Ala-OH 7 (0.5 g, 1.4 mmol) in 10 mL of THF under argon atmosphere at +4° C., isobutyl chloroformate (2.7 mL, 2.1 mmol) and N-methylmorpholine (6.0 mL, 5.5 mmol) were added and the reaction mixture was allowed to stir for 15 min. After 15 min, a solution H-Val-CH$_2$Cl.HCl 8 (0.34 g, 1.8 mmol) in 10 mL of THF was added by syringe over 15 min. The resulting reaction mixture was allowed to stir for 15 h and diluted with DCM (50 mL). The resulting solution was washed with 10 mL of 1N HCl, 10 mL of 5% NaHCO$_3$, and 10 mL of 2M NaCl solution. The collected organic layer was dried over MgSO$_4$, filtered and concentrated using a rotor evaporator. To the resulting residue, 50 mL hexane was added and stirred for 10 min. After stirring for 10 min, the resulting suspension was filtered and dried under vacuum for 10 min. to give Boc-APAV-CH$_2$Cl (SEQ ID NO:3) 9 (0.51 g, 75%) as a pale yellow colored solid.

Preparation of H-APAV-CH$_2$Cl.HCl (SEQ ID NO:3) 10: To a stirred solution of Boc-APAV-CH$_2$Cl (SEQ ID NO:3) 9 (0.50 g, 1.3 mmol) in 10 mL of ethyl acetate, 10 mL of 6N HCl was added. The resulting reaction mixture was allowed to stir at rt for 3 h. After 3 h, the resulting mixture was washed with 50 mL DCM. The collected aqueous solution was evaporated under rotor evaporator to give H-APAV-CH$_2$Cl.HCl (SEQ ID NO:3) 10 (0.36 g, 82%) in an oil form.

allowed to stir at rt for 10 min. After 10 min, methyl succinimidosuccinate 5 (0.18 g, 0.79 mmol) was added and the resulting reaction mixture was allowed to stir at rt for 3 h. After 3 h, the reaction mixture was diluted with DCM (50 mL). The resulting organic layer was washed with water (15 mL) and brine (15 mL). The organic layer was evaporated using a rotor evaporator to give the product MeOSuc-APAV-CH$_2$Cl (SEQ ID NO:3) 11 (0.30 g, 81%) as a white solid. Data for MeOSuc-APAV-CH$_2$Cl (SEQ ID NO:3) 11: $^1$H NMR (CDCl$_3$, 400 MHz) δ 7.18 (d, J=7.2 Hz, 1H), 7.05 (d, J=8.8 Hz, 1H), 6.57 (d, J=6.4 Hz, 1H), 4.62 (m, 2H), 4.48 (m, 1H), 4.39 (m, 1H), 4.32 (d, J=16.4 Hz, 1H), 4.22 (d, J=16.4 Hz, 1H), 3.65 (s, 3H), 3.60 (m, 2H), 2.62 (m, 2H), 2.51 (m, 2H), 2.27-1.95 (m, 4H), 1.80 (m, 1H), 1.34 (m, 4H), 0.93 (d, J=6.8 Hz, 3H), 0.84 (d, J=6.8 Hz, 3H); MS (m/z): 503 [M+H]+.

Synthesis of MeOSuc-AlaProAlaLeu-CH$_2$Cl 15: The synthesis of methoxysuccinyl-APAL-chloromethyl ketone (SEQ ID NO:4) followed the same procedure as for methoxysuccinyl-APAV-chloromethyl ketone (SEQ ID NO:3) above with the substitution of leucine for the valine at position four of the tetrapeptide. The specifics of synthesis are as follows.

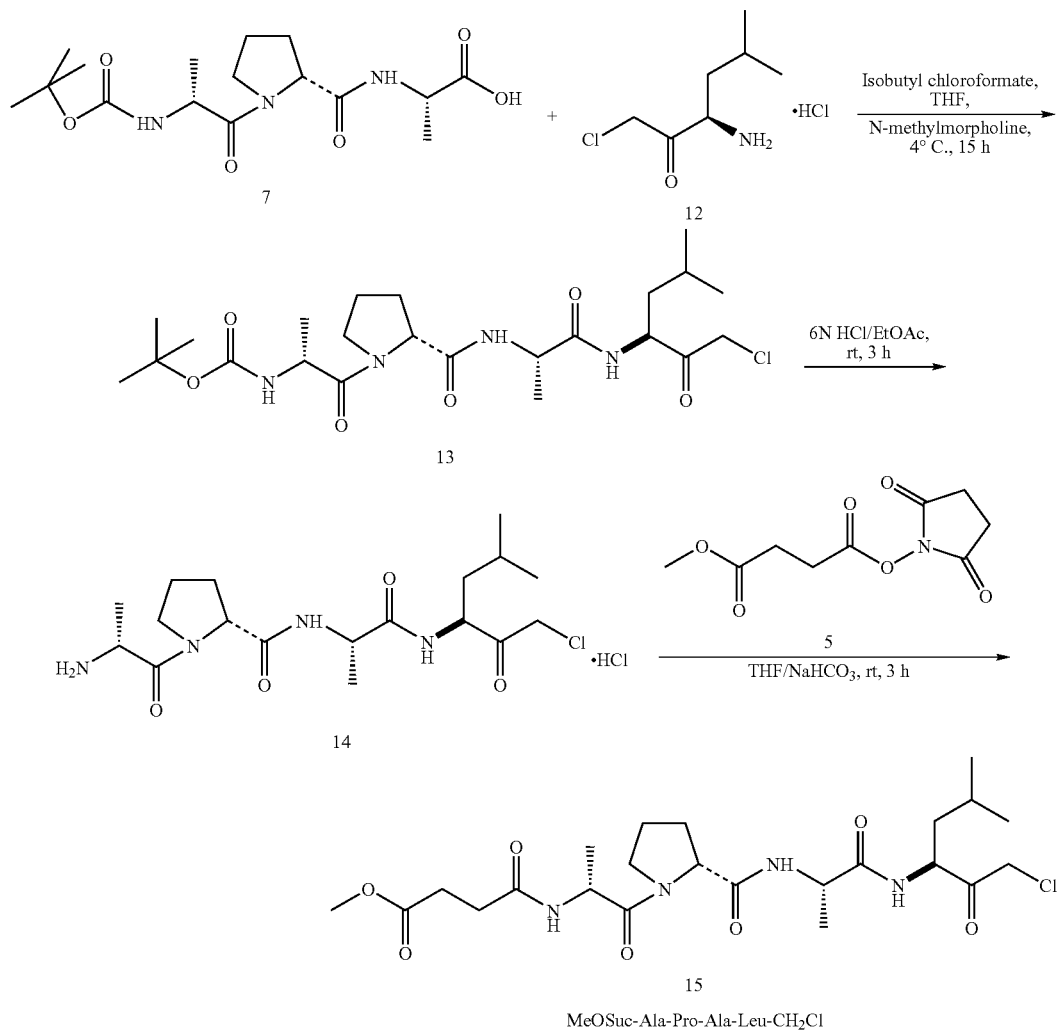

MeOSuc-Ala-Pro-Ala-Leu-CH₂Cl

Preparation of Boc-APAL-CH$_2$Cl (SEQ ID NO:4) 13: To a stirred solution of Boc-Ala-Pro-Ala-OH 7 (0.5 g, 1.4 mmol) in 10 mL of THF under argon atmosphere at +4° C., isobutyl chloroformate (2.7 mL, 2.1 mmol) and N-methylmorpholine (6.0 mL, 5.5 mmol) were added and the reaction mixture was allowed to stir for 15 min. After 15 min, a solution H-Leu-CH$_2$Cl.HCl 12 (0.36 g, 1.8 mmol) in 10 mL of THF was added by syringe over 15 min. The resulting reaction mixture was allowed to stir for 15 h and diluted with DCM (50 mL). The resulting solution was washed with 10 mL of 1N HCl, 10 mL of 5% NaHCO$_3$, and 10 mL of 2M NaCl solution. The collected organic layer was dried over MgSO$_4$, filtered and concentrated under a rotor evaporator. To the resulting residue, 50 mL hexane was added and stirred for 10 min. After stirring for 10 min, the resulting suspension was filtered and then dried under vacuum for 10 min to give Boc-APAL-CH$_2$Cl (SEQ ID NO:4) 13 (0.49 g, 70%) as a pale yellow colored solid.

Preparation of H-APAL-CH$_2$Cl.HCl (SEQ ID NO:4) 14: To a stirred solution of Boc-APAL-CH$_2$Cl (SEQ ID NO:4) (0.48 g, 0.95 mmol) in 10 mL of ethyl acetate, 10 mL of 6N HCl was added. The resulting reaction mixture was allowed to stir at rt for 3 h. After 3 h, the resulting mixture was washed with 50 mL DCM. The collected aqueous solution was evaporated under rotor evaporator to give H-APAL-CH$_2$Cl.HCl (SEQ ID NO:4) 14 (0.36 g, 71%) in an oil form.

Preparation of MeOSuc-APAL-CH$_2$Cl (SEQ ID NO:4) 15: To a stirred solution of H-APAL-CH$_2$Cl.HCl (SEQ ID NO:4) 14 (0.36 g, 0.82 mmol) in 10 mL of THF, a suspension of sodium bicarbonate (1.0 g in 1 mL water) was added and the resulting solution was allowed to stir at rt for 10 min. After 10 min, methyl succinimidosuccinate 5 (0.17 g, 0.74 mmol) was added and the resulting reaction mixture was allowed to stir at rt for 3 h. After 3 h, the reaction mixture was diluted with DCM (50 mL). The resulting organic layer was washed with water (15 mL) and brine (15 mL). The organic layer was evaporated under rotor evaporation to give the product MeOSuc-APAL-CH$_2$Cl (SEQ ID NO:4) 15 (0.29 g, 76%) as a white solid. Data for MeOSuc-APAL-CH$_2$Cl (SEQ ID NO:4) 15: $^1$H NMR (CDCl$_3$, 400 MHz) δ 7.06 (d, J=7.2 Hz, 1H), 7.00 (d, J=7.6 Hz, 1H), 6.45 (d, J=6.4 Hz, 1H), 4.61 (m, 2H), 4.47 (m, 1H), 4.37 (m, 1H), 4.35 (d, J=15.6 Hz, 1H), 4.26 (d, J=16.4 Hz, 1H), 3.65 (s, 3H), 3.58 (m, 2H), 2.62 (m, 2H), 2.51 (m, 2H), 2.15-1.95 (m, 4H), 1.83 (m, 1H), 1.63-1.51 (m, 2H), 1.37 (d, J=6.8 Hz, 3H); 1.34 (d, J=7.2 Hz, 3H), 0.90 (m, 6H); MS (m/z): 517 [M+H]$^+$.

Synthesis of MeOSuc-AlaProAlaPhe-CH$_2$Cl (SEQ ID NO:6) 18: The synthesis of methoxysuccinyl-APAF-chloromethyl ketone (SEQ ID NO:6) followed the same procedure as for methoxysuccinyl-APAL-chloromethyl ketone (SEQ ID NO:4) above with the substitution of phenylalanine for the leucine at position four of the tetrapeptide. The specifics of synthesis are as follows.

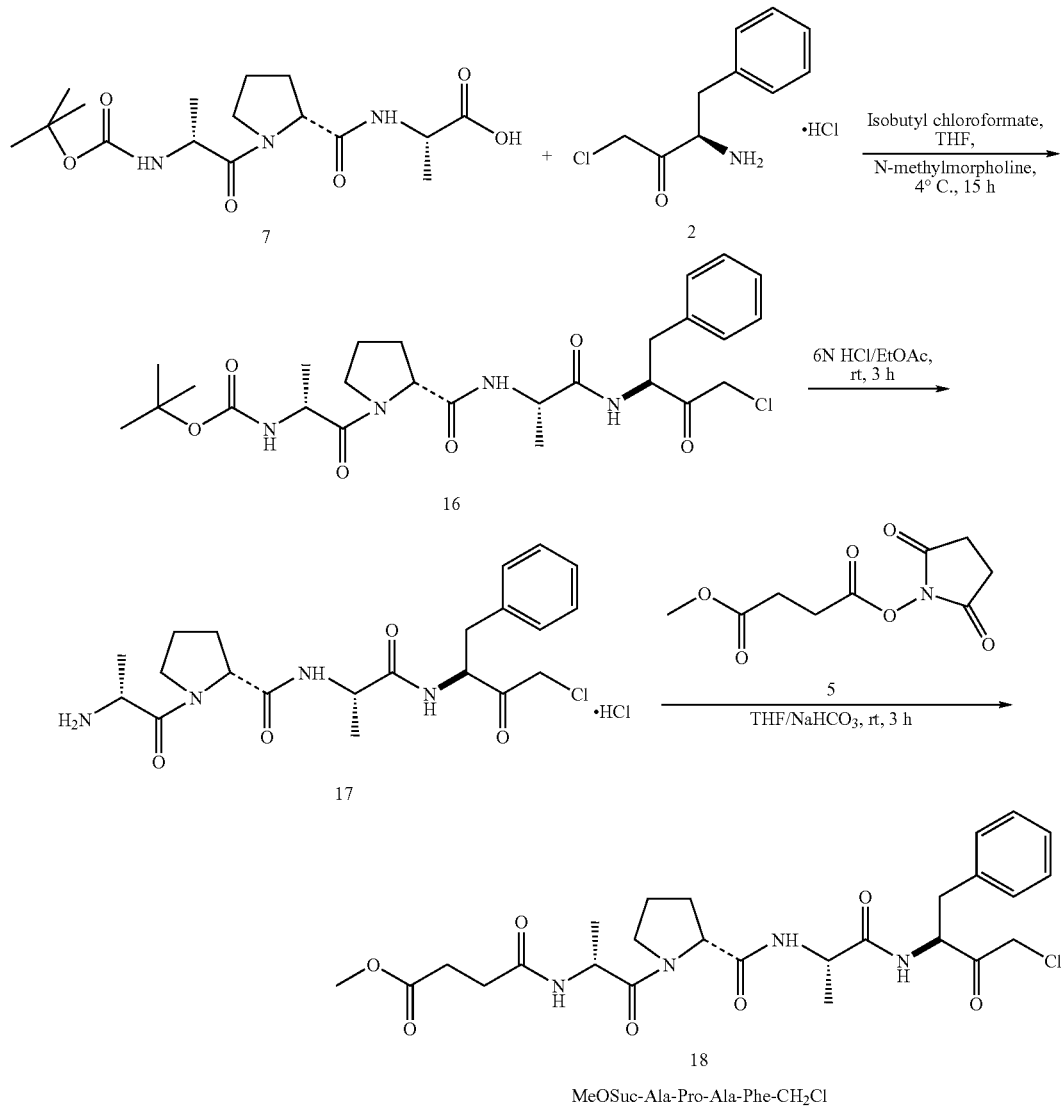

MeOSuc-Ala-Pro-Ala-Phe-CH$_2$Cl

Preparation of Boc-APAF-CH$_2$Cl (SEQ ID NO:6) 16: To a stirred solution of Boc-Ala-Pro-Ala-OH 7 (0.5 g, 1.4 mmol) in 10 mL of THF under argon atmosphere at +4° C., isobutyl chloroformate (2.7 mL, 2.1 mmol) and N-methylmorpholine (6.0 mL, 5.5 mmol) were added and the reaction mixture was allowed to stir for 15 min. After 15 min, a solution H-Phe-CH$_2$Cl.HCl 7 (0.36 g, 1.8 mmol) in 10 mL of THF was added by syringe over 15 min. The resulting reaction mixture was allowed to stir for 15 h and diluted with DCM (50 mL). The resulting solution was washed with 10 mL of 1N HCl, 10 mL of 5% NaHCO$_3$, and 10 mL of 2M NaCl solution. The collected organic layer was dried over MgSO$_4$, filtered and concentrated under a rotor evaporator. To the resulting residue, 50 mL hexane was added and stirred for 10 min. After stirring for 10 min, the resulting suspension was filtered and dried under vacuum for 10 min to give Boc-APAF-CH$_2$Cl (SEQ ID NO:6) 16 (0.64 g, 85%) as a pale yellow colored solid.

Preparation of H-APAF-CH$_2$Cl.HCl (SEQ ID NO:6) 17: To a stirred solution of Boc-APAF-CH$_2$Cl (SEQ ID NO:6) 16 (0.63 g, 1.17 mmol) in 10 mL of ethyl acetate, 10 mL of 6N HCl was added. The resulting reaction mixture was allowed to stir at rt for 3 h. After 3 h, the resulting mixture was washed with 50 mL DCM. The collected aqueous solution was evaporated under rotor evaporator to give H-APAF-CH$_2$Cl.HCl (SEQ ID NO:6) 17 (0.51 g, 93%) in an oil form.

Preparation of MeOSuc-APAF-CH$_2$Cl (SEQ ID NO:6) 18: To a stirred solution of H-APAF-CH$_2$Cl.HCl (SEQ ID NO:6) 17 (0.51 g, 1.08 mmol) in 10 mL of THF, a suspension of sodium bicarbonate (1.0 g in 1 mL water) was added and the resulting solution was allowed to stir at rt for 10 min. After 10 min, methyl succinimidosuccinate 5 (0.23 g, 1.00 mmol) was added and the resulting reaction mixture was allowed to stir at rt for 3 h. After 3 h, the reaction mixture was diluted with DCM (50 mL). The resulting organic layer was washed with water (15 mL) and brine (15 mL). The organic layer was evaporated under rotor evaporator to give the product MeO-Suc-APAF-CH$_2$Cl (SEQ ID NO:6) 18 (0.42 g, 76%) as a white solid. Data for MeOSuc-APAF-CH$_2$Cl (SEQ ID NO:6) 18: $^1$H NMR (CDCl$_3$, 400 MHz) δ 7.27-7.07 (m, 7H), 6.52 (d, J=6.8 Hz, 1H), 4.81 (m, 1H), 4.61 (m, 1H), 4.35 (m, 2H), 4.28

(d, J=16.4 Hz, 1H), 4.04 (d, J=16.4 Hz, 1H), 3.72 (m, 1H), 3.64 (s, 3H), 3.54 (m, 1H), 3.16 (m, 1H), 2.96 (m, 1H), 2.61 (m, 2H), 2.50 (m, 2H), 2.11-1.81 (m, 4H), 1.32 (d, J=6.8 Hz, 3H), 1.21 (d, J=7.2 Hz, 3H); MS (m/z): 551 [M+H]$^+$.

Synthesis of MeOSuc-AlaAlaProLeu-CH$_2$Cl (SEQ ID NO:10): The synthesis of methoxysuccinyl-AAPL-chloromethyl ketone (SEQ ID NO:10) followed the same procedure as for methoxysuccinyl-AAPV-chloromethyl ketone (SEQ ID NO:2) above with the substitution of leucine for the valine at position four of the tetrapeptide. The specifics of synthesis are as follows.

Preparation of Boc-AAPL-CH$_2$Cl (SEQ ID NO:10): To a stirred solution of Boc-Ala-Ala-Pro-OH 1 (0.5 g, 1.4 mmol) in 10 mL of tetrahydrofuran (THF) under argon atmosphere at +4° C., isobutyl chloroformate (2.7 mL, 2.1 mmol) and N-methylmorpholine (6.0 mL, 5.5 mmol) were added and the reaction mixture was allowed to stir for 15 min. After 15 min, a solution of Leu-CH$_2$Cl.HCl 12 (0.39 g, 2.0 mmol) in 10 mL of THF was added by syringe over 15 min. The resulting reaction mixture was allowed to stir for 15 h and diluted with dichloromethane (DCM, 50 mL). The resulting solution was washed with 10 mL of 1N HCl, 10 mL of 5% NaHCO$_3$, and 10 mL of 2M NaCl solution. The collected organic layer was dried over MgSO$_4$, filtered and concentrated under rotor evaporator. To the resulting residue, 50 mL hexane was added and stirred for 10 min. After stifling for 10 min the resulting suspension was filtered and dried under vacuum for 10 min to give Boc-AAPL-CH$_2$Cl (SEQ ID NO:10) (0.63 g, 90%) as a pale yellow colored solid.

Preparation of H-AAPL-CH$_2$Cl.HCl (SEQ ID NO:10): To a stirred solution of Boc-AAPL-CH$_2$Cl (SEQ ID NO:10) (0.62 g, 1.3 mmol) in 10 mL of ethyl acetate, 10 mL of 6N HCl was added. The resulting reaction mixture was allowed to stir at room temperature (rt) for 3 h. After 3 h, the resulting mixture was washed with 50 mL DCM. The collected aqueous solution was evaporated under rotor evaporator to give H-AAPL-CH$_2$Cl.HCl (SEQ ID NO:10) (0.47 g, 87%) in an oil form.

Preparation of MeOSuc-AAPL-CH$_2$Cl (SEQ ID NO:10): To a stirred solution of H-AAPL-CH$_2$Cl.HCl (SEQ ID NO:10) (0.47 g, 1.1 mmol) in 10 mL of THF, a suspension of sodium bicarbonate (1.0 g in 1 mL water) was added and allowed to stir at rt for 10 min. After 10 min, methyl succinimidosuccinate 5 (0.24 g, 1.0 mmol) was added and the resulting reaction mixture was allowed to stir at rt for 3 h. After 3 h, the reaction mixture was diluted with DCM (50 mL). The resulting organic layer was washed with water (15 mL) and brine (a saturated solution of NaCl) (15 mL). The organic layer was evaporated under a rotor evaporator to give the product MeOSuc-AAPL-CH$_2$Cl (SEQ ID NO:10) (0.40 g, 74%) as a white solid. Data for MeOSuc-AAPL-CH$_2$Cl (SEQ ID NO:10): $^1$H NMR (CDCl$_3$, 400 MHz) δ 7.15 (d, J=8.4 Hz, 1H), 7.80 (d, J=7.6 Hz, 1H), 6.60 (d, J=8.0 Hz, 1H), 4.83 (m, 2H), 4.55 (m, 1H), 4.49 (m, 1H), 4.23 (s, 2H), 3.75 (m, 1H), 3.65 (s, 3H), 3.63 (m, 1H), 2.61 (m, 2H), 2.49 (m, 2H), 2.22-1.96 (m, 5H), 1.55 (m, 2H), 1.32 (d, J=7.6 Hz, 3H), 1.16 (d, J=6.8 Hz, 3H), 0.85 (d, J=6.4 Hz, 6H); MS (m/z): 517 [M+H]$^+$.

Example 2

Analysis of Methoxysuccinyl Tetrapeptide Chloromethylketone Compounds for Proteinase K Inhibitory Activity, Indirect Linked Assay The present example provides for inhibition of proteinase K in the context of preparing samples for nucleic acid detection. Said preparation of samples is described by pending U.S. patent application Ser. No. 12/122,274 filed May 16, 2008 entitled "Sample Preparation for In Situ Nucleic Acid Analysis, Methods and Compositions Therefor," hereby incorporated by reference in its entirety. Embodiments of said patent application provide a process for preparing a sample containing RNA for in situ analysis of RNA or a surrogate thereof. In some embodiments, the process comprises contacting the sample containing RNA with a lysis mixture comprising a polypeptide having protease activity under conditions and for a time to produce a lysate, and admixing at least a portion of the lysate with a stop mixture that comprises an inhibitor of the polypeptide having protease activity at substantially the same temperature as the contacting step to form a stopped mixture. The resultant stopped mixture is preferably compatible with in situ reverse transcriptase and DNA polymerase reactions.

Methoxysuccinyl tetrapeptide chloromethylketone compounds synthesized as set forth in Example 1 herein were analyzed for inhibitory activity of proteinase K in such stopped mixtures as described below. Functional validation for the nucleic acid detection system using inhibitors of embodiments herein was carried out by measuring mRNA levels in biological samples using the TaqMan® Gene Expression Cells-to-C$_T$™ Kit and the TaqMan® Cells-to-C$_T$™ Control Kit (Applied Biosystems, Foster City, Calif.). MicroAmp® optical 96-well reaction plates were purchased from Applied Biosystems. Disposable reagent reservoirs were purchased from VistaLab Technologies, Inc (Mt. Kisco, N.Y.). Reverse transcription (RT) reactions were performed at 37° C. for 60 min, 95° C. for 5 min, and cooled to 4° C. by using GeneAmp® PCR systems 9700 (Applied Biosystems). Real time PCR was performed by using 7500 Fast Real-Time PCR System. (Applied Biosystems).

The present indirect linked assay measures the amount of inhibition of proteinase K activity by assaying reverse transcriptase real time PCR amplification of a template, which amplification is dependent upon reverse transcriptase activity. The effectiveness of a test inhibitor is determined by whether proteinase K in the stopped mixture is able to digest RT, thereby rendering RT inactive for transcription.

Stop solutions (100 µL) contained the following reagents (10× concentration):
 Tris pH 8.0, 11 mM;
 EGTA pH 9.0, 88 mM;
 RNase inhibitor (RIP protein), 2.2 U/µL;
 DTT, 0.11 mM and
 Test inhibitor, 11 mM (final concentration when diluted into stopped mixture is 1 mM). Test inhibitor was also used at concentrations such that, when diluted with a lysis mixture to form a stopped mixture as described below, the final concentration of inhibitor in the stopped mixture was 0.75 mM, 0.5 mM, 0.25 mM, 0.10 mM, 0.05 mM and 0 mM (control).

The stop solution was mixed well and its pH was adjusted to 8.0, if required, by dilute HCl.

Proteinase K lysis solution (50 µL (no added DNase)) from the TaqMan® gene expression Cells-to-C$_T$™ kit (Applied Biosystems) was aliquoted into 18 tubes. To the test samples (these are a working equivalent to lysis mixtures in the Cells-to-C$_T$™ workflow), stop solution (5 µL) was added; the tubes were mixed and held for 2 min at room temperature. For the control reactions, 50 µl of proteinase K buffer was mixed with 5 µl of stop mix without inhibitor and the resulting reaction mixture was heated at 95° C. for 10 min to thermally inactivate the proteinase K reaction. Next, reverse transcription reagents were prepared, i.e. 15 µL 2×RT buffer, and 1.5 µL of 20×RT enzyme mix, were aliquoted and mixed in the wells of a 96 well plate. To this RT solution, 13.5 μL of each proteinase K containing stopped mixture was added and the solution was mixed well. The resulting mixtures were incubated at room temperature for 1 hr for residual proteinase K activity to degrade the RT enzyme. After 1 hr incubation at room temperature, 1 μL of Xeno™ RNA Control template (Applied Biosystems P/N 4386995 diluted to 25,000 copies/μL in 10 ng/μL poly A) was added to all wells except for the no template control wells. Then the reverse transcription (RT) reaction was incubated at 37° C. for 60 min, 95° C. for 5 min, and cooled to 4° C. by using GeneAmp® PCR systems 9700. (Applied Biosystems). Proteinase K inhibition assays were carried out in triplicate.

Real time PCR was performed using the TaqMan® Cells-to-Ct™ Xeno AOD (Assay on Demand) primers and probe (Applied Biosystems) on the 7500 Fast Real-Time PCR instrument (Applied Biosystems). In each reaction, the equivalent of 12.5 μl of TaqMan® Gene Expression master mix mixed with 1.25 μl of 20× Xeno AOD was dispensed in each well of a 96 well plate. A volume of 11.25 μl of each RT reaction was then added to each well. For three control reactions, 11.25 μl of water was added to the three wells. Then the 96 well plate was run by using the gene expression parameters as per manufacturer's instruction.

The results of the assays for inhibitory activity of test methoxysuccinyl tetrapeptide chloromethylketone compounds are provided by the histogram of FIG. 1 in which average Ct (cycle threshold) values are plotted against various concentrations of each tetrapeptide in the stopped reactions. Control reactions included 100% heat killed mixtures in which proteinase K activity is fully inactivated, MeOSuc-AAPV-CH$_2$Cl (SEQ ID NO:2) as a positive control inhibitor, 0 mM inhibitor, control Xeno™ RNA template only spiked into deionized water, lysis solution only, and no template control reaction (NTCRT). Ct values of ~40 represent samples with active proteinase K activity since the RT reaction is inhibited while Ct values of ~30 represent samples lacking proteinase K activity due to inhibition by the test compound. In such samples, RT generates template for amplification.

The histogram of FIG. 1 provides results for the known proteinase K inhibitor MeOSuc-AAPV-CH$_2$Cl (SEQ ID NO:2) (positive control), and for four test inhibitors MeOSuc-APAV-CH$_2$Cl (SEQ ID NO:3), MeOSuc-APAL-CH$_2$Cl (SEQ ID NO:4), MeOSuc-AAPF-CH$_2$Cl (SEQ ID NO:5) and MeOSuc-APAF-CH$_2$Cl (SEQ ID NO:6) ranging in concentration from 1 mM to 0.05 mM in the stopped mixtures.

The positive control inhibitor, MeOSuc-AAPV-CH$_2$Cl (SEQ ID NO:2), is inhibitory for proteinase K activity at concentrations as low as about 0.25 mM concentration (FIG. 1) and as stated by U.S. patent application Ser. No. 12/122,274, previously incorporated by reference herein. The Ct values increase from about 30 at 0.5 mM to about 33 at 0.25 mM and to 40 at 0.1 mM.

The test inhibitors MeOSuc-APAV-CH$_2$Cl (SEQ ID NO:3) and MeOSuc-APAF-CH$_2$Cl (SEQ ID NO:6) are inactive at all concentrations tested (FIG. 1). No Xeno RNA is detected in any of the reactions (CT=40), indicating that the proteinase K retained activity so as to eradicate reverse transcriptase activity.

The test inhibitor MeOSuc-APAL-CH$_2$Cl (SEQ ID NO:4) is inhibitory for proteinase K activity at concentrations as low as about 0.5 mM (FIG. 1). This result is unexpected since MeOSuc-APAV-CH$_2$Cl (SEQ ID NO:3) and MeOSuc-APAF-CH$_2$Cl (SEQ ID NO:6), each also having a proline at the second amino acid position of the tetrapeptide, are inactive.

The test inhibitor MeOSuc-AAPF-CH$_2$Cl (SEQ ID NO:5) is an even better inhibitor than MeOSuc-AAPV-CH$_2$Cl (SEQ ID NO:2) since MeOSuc-AAPF-CH$_2$Cl (SEQ ID NO:5) has inhibitory activity for proteinase K at concentrations as low as about 0.05 mM (FIG. 1), having a Ct value of about 30 at that concentration. In contrast, MeOSuc-AAPV-CH$_2$Cl (SEQ ID NO:2) begins to lose efficacy at a concentration greater than 0.25 mM (FIG. 1). This result is also unexpected since the phenylalanine side chain of MeOSuc-AAPF-CH$_2$Cl (SEQ ID NO:5) has significant bulk as compared to the valine side chain of MeOSuc-AAPV-CH$_2$Cl (SEQ ID NO:2).

Example 3

Analysis of MeOSuc-AAPF-CH$_2$Cl (SEQ ID NO:5) for Proteinase K Inhibitory Activity, Direct Assay A direct assay for inhibition of proteinase K activity by MeOSuc-AAPF-CH$_2$Cl (SEQ ID NO:5) was carried out using bovine serum albumin (BSA) as substrate and analyzing products using each Bioanalyzer chips and precast protein gels. Such direct assays were carried out to separate inhibition of proteinase K by a test inhibitor from any effects the stopped mixture may have on an RT-PCR reaction.

Figure 2:
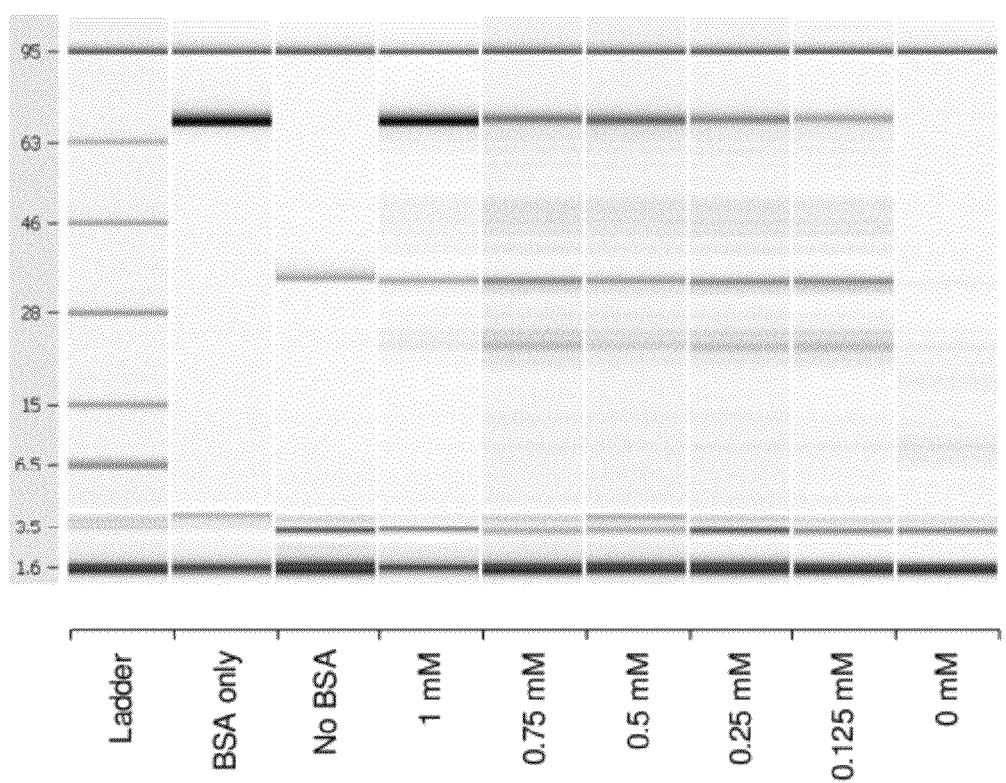

The reaction mixtures included the proteinase K solution (50 μL, 100 μg/ml) mixed with 5 μL of stop solution having varying amounts of tetrapeptide, MeOSuc-AAPF-CH$_2$Cl (SEQ ID NO:5), as for Example 2. Incubation was for 10 min at room temperature. To assay for proteinase K activity, ultrapure BSA (12 μL of 50 mg/ml) was added to each sample and the samples were held for 10 min at room temperature. Resultant mixtures were heated for 30 min at 95° C. and analyzed using a Protein 80 Bioanalyzer chip (2100 Bioanalyzer, Agilent, Santa Clara, Calif.). The Bioanalyzer protein gel data is provided in FIG. 2, in which intact Ultrapure BSA (Applied Biosystems) is at about 70 kDa, and proteinase K is at about 35 kDa. The lanes of FIG. 2 are labeled as follows from left to right: Ladder; BSA only; No BSA (proteinase K only); MeOSuc-AAPF-CH$_2$Cl (SEQ ID NO:5) in the stopped mixture at 1 mM, 0.75 mM, 0.5 mM, 0.25 mM, 0.125 mM, and 0 mM.

As shown by FIG. 2, MeOSuc-AAPF-CH$_2$Cl (SEQ ID NO:5) was capable of inhibiting proteinase K at concentrations as low as 0.125 mM and at even lower concentrations when incubated with proteinase K for a longer period of time prior to addition of the BSA substrate.

Figure 3:
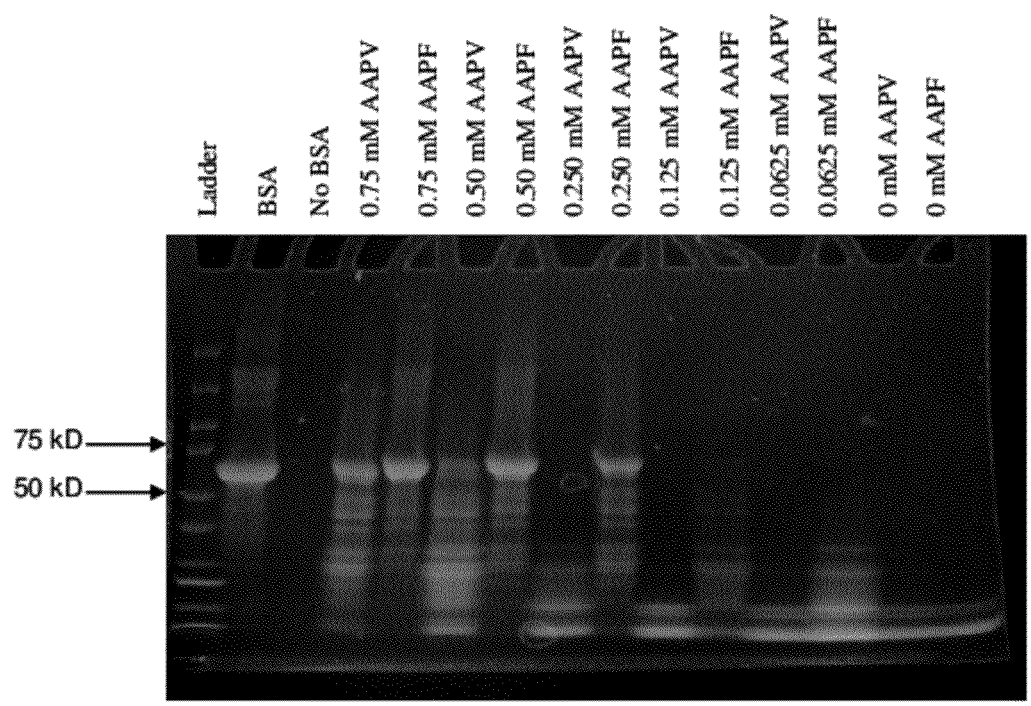

For the precast SDS denaturing protein gel analysis data of FIG. 3, proteinase K (50 μl of 100 μg/ml) lysis mixture without DNase (as for Example 2) was mixed with 5 μl of stop solution with varying amounts of MeOSuc-AAPF-CH$_2$Cl (SEQ ID NO:5) and incubated for 10 min at room temperature. Ultrapure BSA (10 μl of 5 mg/ml, Applied Biosystems) was added to each sample and the samples were held for 10 min at room temperature. The reaction mixture was heated for 30 min at 95° C. and analyzed using precast protein gels (BIO-RAD, Hercules, Calif.). From the 65 μl of total reaction mixture, 10 μl reaction mixture was mixed with 5 μl of gel loading dye and further heated at 95° C. for 5 min. Then, the reactions were kept on ice for 2 min and loaded on the gel. Control reactions, with and without BSA, were also carried out. The Precision Plus Protein™ Standards from Bio-Rad were used as the marker ladder.

The precast protein gel was run at 120 V for 1 h using 1× Tris/glycine/SDS buffer (BIO-RAD, Hercules, Calif.). The gel was stained with Coomassie blue stain for 1 h at room temp and destained with destaining solution (20% acetic acid, 10% methanol in 1 L). The gel was analyzed using AlphaEase™ FC software (Alpha Innotech, San Leandro, Calif.).

The protein gel data are summarized in FIG. 3, in which the ladder ranges in size from 10 kD to 250 kD. Intact Ultrapure BSA is at about 70 Kd, and proteinase K is at about 35 kDa. The lanes of FIG. 3 are labeled as follows: Ladder, BSA, No BSA (proteinase K only), 0.75 mM MeOSuc-AAPV-CH$_2$Cl (SEQ ID NO:2), 0.75 mM MeOSuc-AAPF-CH$_2$Cl (SEQ ID NO:5), 0.5 mM MeOSuc-AAPV-CH$_2$Cl (SEQ ID NO:2), 0.5 mM MeOSuc-AAPF-CH$_2$Cl (SEQ ID NO:5), 0.250 mM MeOSuc-AAPV-CH$_2$Cl (SEQ ID NO:2), 0.250 mM MeOSuc-AAPF-CH$_2$Cl (SEQ ID NO:5), 0.125 mM MeOSuc-AAPV-CH$_2$Cl (SEQ ID NO:2), 0.125 mM MeOSuc-AAPF-CH$_2$Cl (SEQ ID NO:5), 0.065 mM MeOSuc-AAPV-CH$_2$Cl (SEQ ID NO:2), 0.065 mM MeOSuc-AAPF-CH$_2$Cl (SEQ ID NO:5), 0 mM MeOSuc-AAPV-CH$_2$Cl (SEQ ID NO:2), and 0 mM MeOSuc-AAPF-CH$_2$Cl (SEQ ID NO:5). The MeOSuc-AAPF-CH$_2$Cl (SEQ ID NO:5) compound was capable of inhibiting proteinase K at concentrations at least half that of MeOSuc-AAPV-CH$_2$Cl (SEQ ID NO:2) (compare the lanes at 0.5 mM and at 0.25 mM), although protein gel data are less sensitive than the RT-PCR indirect linked assay of Example 2.

These data demonstrate that the results of the indirect linked assay of Example 2 are due to inhibition of the proteinase K by the test inhibitors and are not due to an inhibition of the RT-PCR reaction.

Example 4

Figures 4A, 4B, 4C, 4D:
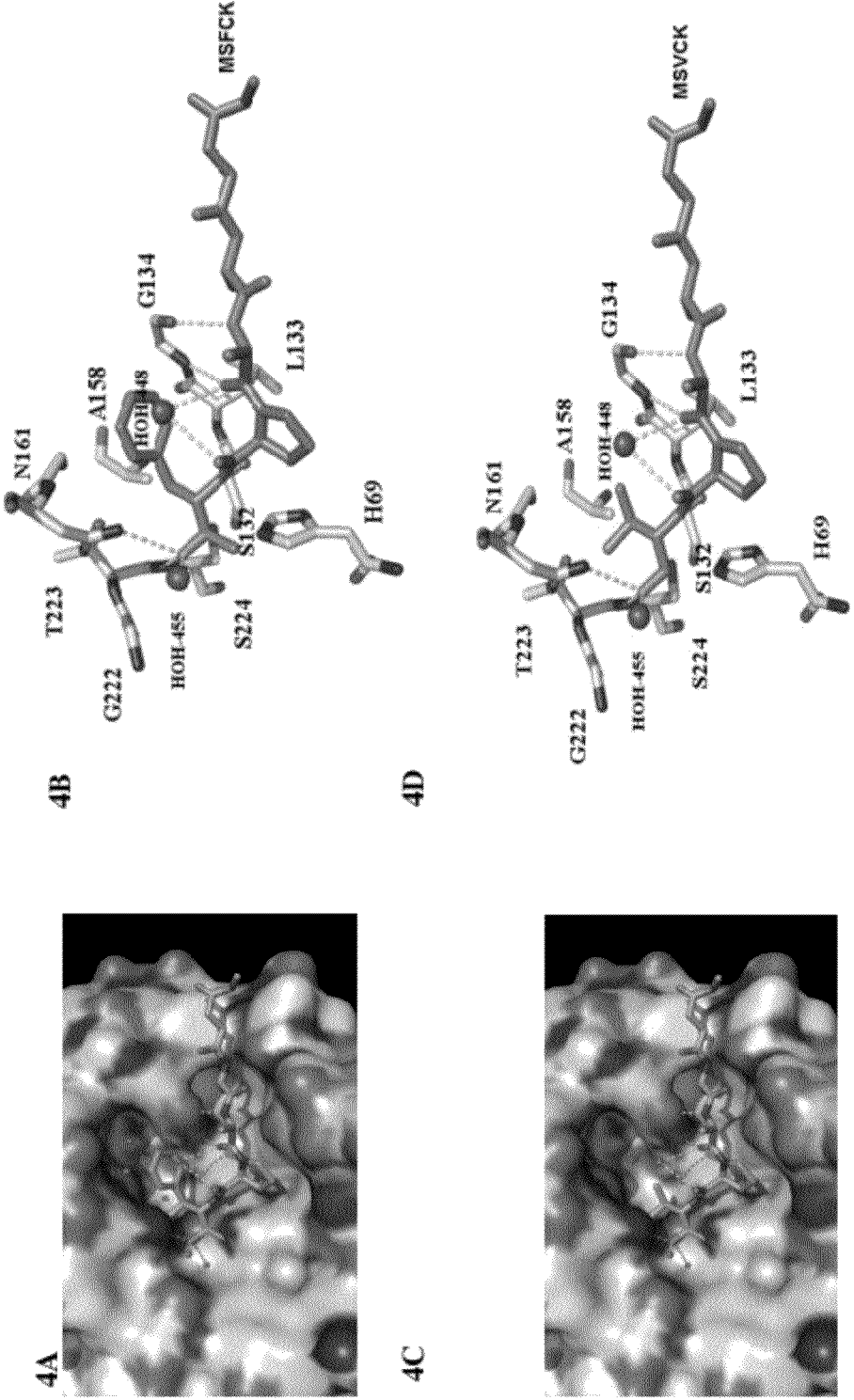

Molecular Model Building Studies of MeOSuc-AAPF-CH$_2$Cl (SEQ ID NO:5) Positioned in the Binding Site of Proteinase K In light of the results of Examples 2 and 3 where large changes in inhibitory activity were found depending on inhibitor amino acid sequence and side chain size, computer model building studies were carried out on MeOSuc-AAPF-CH$_2$Cl (SEQ ID NO:5) bound to proteinase K. The coordinates of proteinase K and human neutrophil elastase, also a serine protease, each in a complex with MeOSuc-AAPA-CH$_2$Cl (SEQ ID NO:1) at 2.2 Å resolution (Wolf, W. M. et al., *Journal of Biological Chemistry* 1991, 266, 17695) or at 1.84 Å resolution (Navia, M. A. et al., *Proc. Natl. Acad. Sci.* 1989, 86:7-11) were used as a starting point for molecular model building. The program WinCoot (Emsley, P., et al., *Acta Crystallographica Section D Biological Crystallography* 2004, 60, 2126) was used to model the inhibitors MeOSuc-AAPV-CH$_2$Cl (SEQ ID NO:2) and MeOSuc-AAPF-CH$_2$Cl (SEQ ID NO:5) in place of MeOSuc-AAPA-CH$_2$Cl (SEQ ID NO:1). The model building shown in FIG. 4A-FIG. 4D were constructed using the visualization program PyMol (DeLano, W. L. The PyMOL Molecular Graphics System, DeLano Scientific, Palo Alto, 2002, CA). Examination of the active site around the fourth amino acid of the tetrapeptide inhibitor (P1 according to the Schechter nomenclature referred to in Wolf et al.) revealed a small binding pocket, shown by surface representations in FIG. 4A (for MeOSuc-AAPF-CH$_2$Cl (SEQ ID NO:5)) and FIG. 4C (for MeOSuc-AAPV-CH$_2$Cl (SEQ ID NO:2)). This binding pocket potentially offers additional van der Waals, hydrogen bond, and/or hydrophobic interactions to enhance inhibitor potency as depicted in the model building of FIG. 4B for MeOSuc-AAPF-CH$_2$Cl (SEQ ID NO:5) as compared to the model building of FIG. 4D for MeOSuc-AAPV-CH$_2$Cl (SEQ ID NO:2). In light of the potent inhibitory activity of the MeOSuc-AAPF-CH$_2$Cl (SEQ ID NO:5) compound for proteinase K as demonstrated herein, the compounds MeOSuc-AAPY-CH$_2$Cl (SEQ ID NO:11) and MeOSuc-AAPW-CH$_2$Cl (SEQ ID NO:12) having a tyrosine or tryptophan in place of phenylalanine in the fourth amino acid position (P1 position), respectively, are likely to be effective inhibitors of proteinase K also.

While not wanting to be bound by theory, the greater inhibitory activity of the MeOSuc-AAPF-CH$_2$Cl (SEQ ID NO:5) compound as compared to the MeOSuc-AAPV-CH$_2$Cl (SEQ ID NO:2) compound is possibly due, in part, to the nature of the chloromethyl ketone-bearing amino acid. In the case of MeOSuc-AAPF-CH$_2$Cl (SEQ ID NO:5), the phenylalanine has an aromatic side chain phenyl group that appears to fit into the binding pocket which may contribute to the greater inhibitory activity.

In light of the inactivity of MeOSuc-APAF-CH$_2$Cl (SEQ ID NO:6) and MeOSuc-APAV-CH$_2$Cl (SEQ ID NO:3) as inhibitors and the activity of MeOSuc-AAPF-CH$_2$Cl (SEQ ID NO:5) and MeOSuc-AAPV-CH$_2$Cl (SEQ ID NO:2) as inhibitors, the activity of MeOSuc-APAL-CH$_2$Cl (SEQ ID NO:4) is unexpected. The inactivity of MeOSuc-APAF-CH$_2$Cl (SEQ ID NO:6) and MeOSuc-APAV-CH$_2$Cl (SEQ ID NO:3) suggests that a proline at amino acid position 2 of the inhibitor (P3 in Schechter nomenclature referred to in Wolf et al.) is incompatible with inhibitor activity. However, the data of Example 2 teach otherwise.

Example 5

Synthesis of Methoxysuccinyl Pentapeptide Chloromethylketone Compounds

Synthesis of methoxysuccinyl pentapeptide chloromethyl ketone compounds is as follows. Characterization and confirmation of structure were by $^1$H NMR and mass spectroscopy. The synthons were purchased from Bachem (Torrence, Calif.) and Chemimpex (Wood Dale, Ill.) and used without further purification. Methoxysuccinyl-AlaAlaProVal chloromethyl ketone was purchased from Bachem. Organic solvents were purchased from Sigma-Aldrich (St. Louis, Mo.).

Synthesis of MeOSuc-AlaAlaAlaProVal-CH$_2$Cl 22 (SEQ ID NO:8):

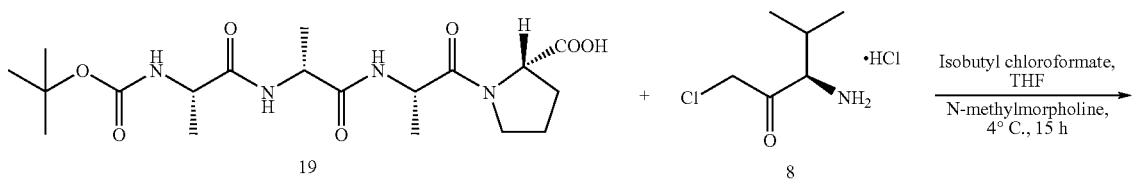

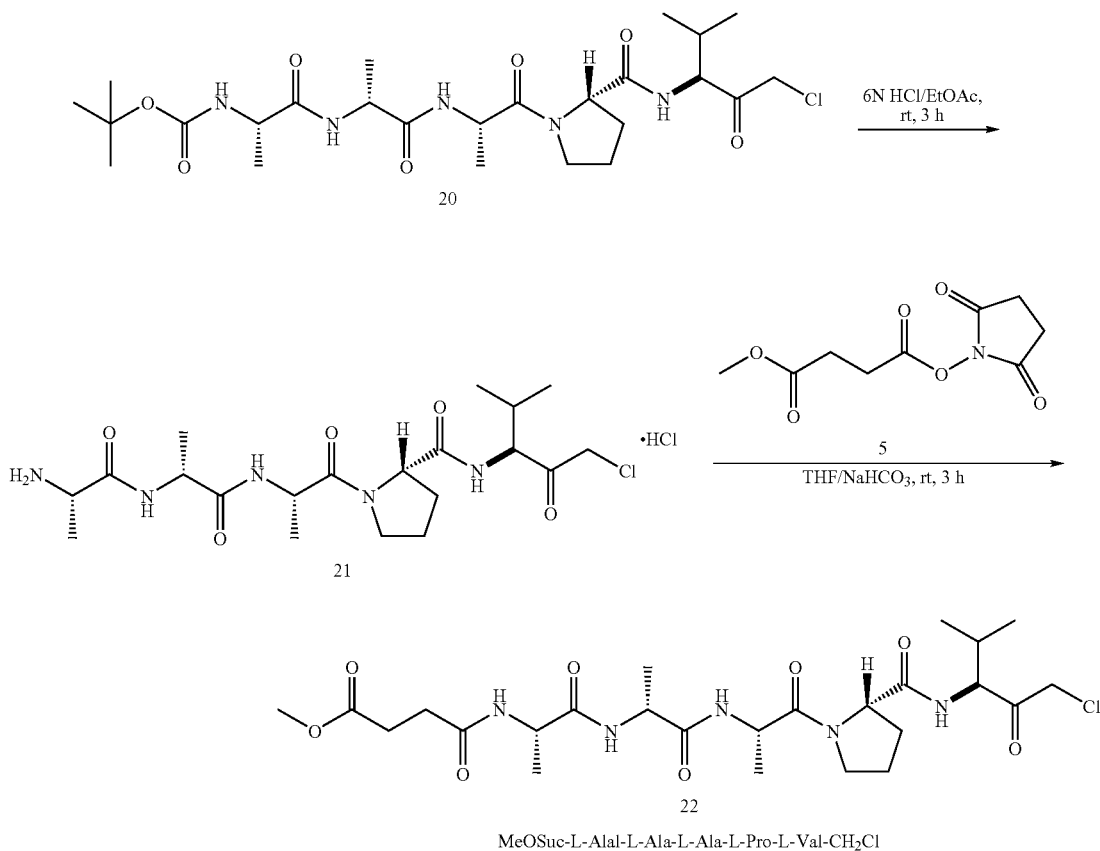

MeOSuc-L-Alal-L-Ala-L-Ala-L-Pro-L-Val-CH₂Cl

Preparation of Boc-AAAPV-CH₂Cl (SEQ ID NO:8) 20: To a stirred solution of Boc-Ala-Ala-Ala-Pro-OH 19 (0.5 g, 1.17 mmol) in 10 mL of THF under argon atmosphere at +4° C., isobutyl chloroformate (0.23 mL, 1.76 mmol) and N-methylmorpholine (0.51 mL, 4.65 mmol) were added and the reaction mixture was allowed to stir for 15 min. After 15 min. a solution of Val-CMK.HCl 8 (0.30 g, 1.62 mmol) in 10 mL of THF was added by syringe over 15 min. The resulting reaction mixture was allowed to stir for 15 h and diluted with DCM (50 mL). The resulting solution was washed with 10 mL of 1N HCl, 10 mL of 5% NaHCO₃, and 10 mL of 2M NaCl solution. The collected organic layer was dried over MgSO₄, filtered and concentrated under rotor evaporator. To the resulting residue, 50 mL hexane was added and stirred for 10 min. After stirring for 10 min, the resulting suspension was filtered and dried under vacuum for 10 min. to give Boc-AAAPV-CMK (SEQ ID NO:8) 20 (0.62 g, 95%) as a pale yellow colored solid.

Preparation of H-AAAPV-CH₂Cl.HCl (SEQ ID NO:8) 21: To a stirred solution of Boc-AAAPV-CH₂Cl (SEQ ID NO:8) 20 (0.61 g, 1.09 mmol) in 10 mL of ethyl acetate, 10 mL of 6N HCl was added. The resulting reaction mixture was allowed to stir at room temperature for 3 h. After 3 h, the resulting mixture was washed with 50 mL DCM. The collected aqueous solution was evaporated under rotor evaporator to give H-AAAPV-CH₂Cl.HCl (SEQ ID NO:8) 21 (0.52 g, 96%) as an oil.

Preparation of MeOSuc-AAAPV-CH₂Cl (SEQ ID NO:8) 22: To a stirred solution of H-AAAPV-CH₂Cl.HCl (SEQ ID NO:8) 21 (0.52 g, 1.05 mmol) in 10 mL of THF, a suspension of sodium bicarbonate (1.0 g in 1 mL water) was added and the resulting solution was allowed to stir at room temperature for 10 min. After 10 min, methyl succinimidosuccinate 5 (0.22 g, 0.96 mmol) was added and the resulting reaction mixture was allowed to stir at room temperature for 3 h. After 3 h, the reaction mixture was diluted with DCM (50 mL). The resulting organic layer was washed with water (15 mL) and brine (15 mL). The organic layer was evaporated under rotor evaporator to give the product MeOSuc-AAAPV-CH₂Cl (SEQ ID NO:8) 22 (0.45 g, 82%) as a white colored solid. Data for MeOSuc-AAAPV-CH₂Cl (SEQ ID NO:8) 22: $^1$H NMR (CDCl₃, 400 MHz) δ 7.58 (d, J=8.4 Hz, 1H), 7.52 (d, J=7.2 Hz, 1H), 6.97 (d, J=8.0 Hz, 1H), 6.39 (d, J=6.4 Hz, 1H), 4.59 (m, 3H), 4.54 (m, 1H), 4.41 (m, 1H), 4.36 (d, J=16.4 Hz, 1H), 4.24 (d, J=16.4 Hz, 1H), 3.74 (m, 1H), 3.65 (s, 3H), 3.57 (m, 1H), 2.80 (m, 1H), 2.63 (m, 1H), 2.49 (m, 2H), 2.26-1.94 (m, 5H), 1.39 (d, J=6.8 Hz, 3H), 1.34 (d, J=6.8 Hz, 3H), 1.32 (d, J=6.8 Hz, 3H), 0.90 (d, J=6.8 Hz, 3H), 0.81 (d, J=8.4 Hz, 3H); MS (m/z): 574 [M+H]⁺.

Synthesis of MeOSuc-AlaAlaAlaProLeu-CH$_2$Cl $25$ (SEQ ID NO:7):

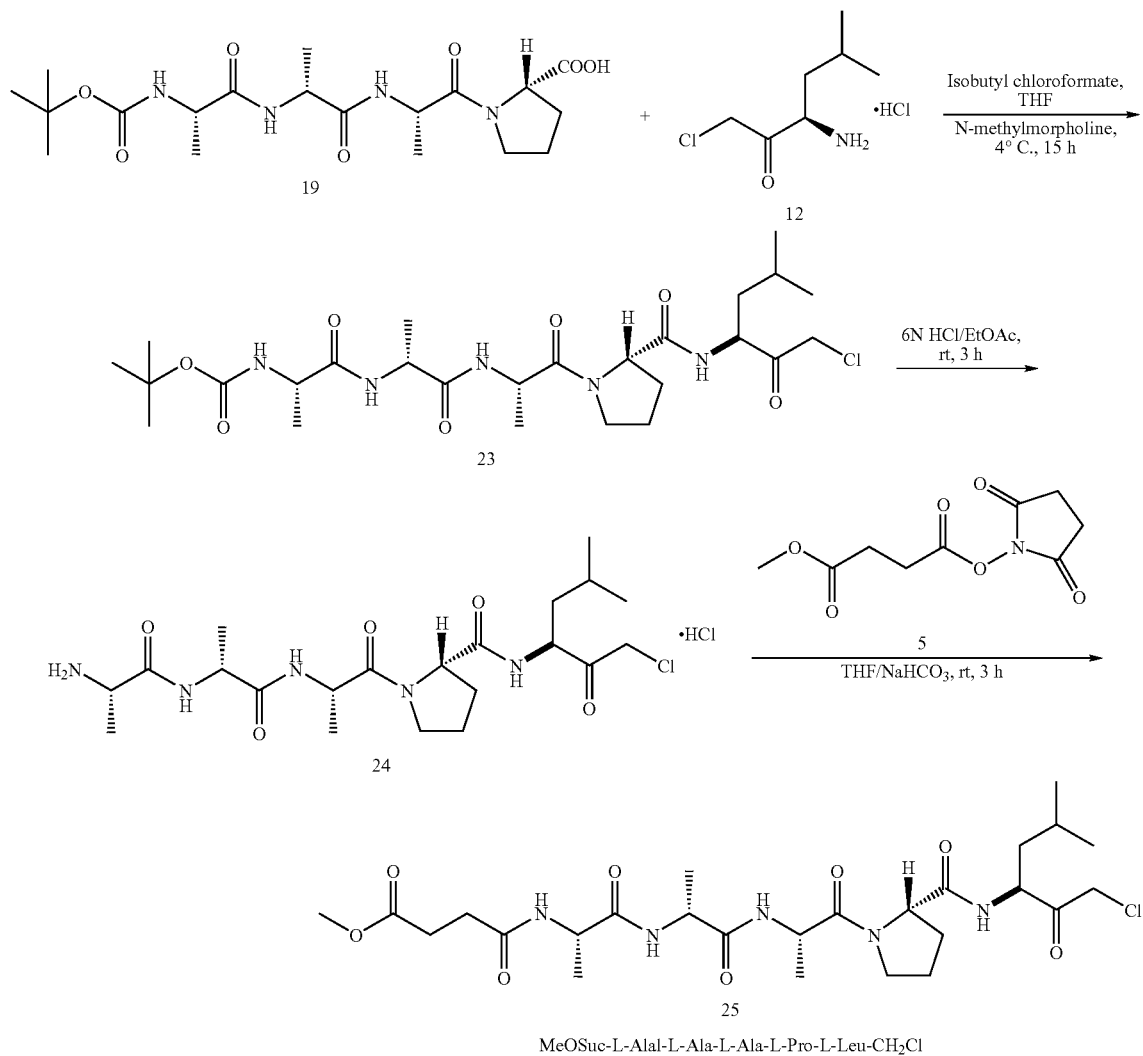

MeOSuc-L-Ala1-L-Ala-L-Ala-L-Pro-L-Leu-CH$_2$Cl

Preparation of Boc-AAAPL-CH$_2$Cl (SEQ ID NO:7) 23: To a stirred solution of Boc-Ala-Ala-Ala-Pro-OH 19 (0.50 g, 1.17 mmol) in 10 mL of THF under argon atmosphere at +4° C., isobutyl chloroformate (0.23 mL, 1.76 mmol) and N-methylmorpholine (0.51 mL, 4.65 mmol) were added and the reaction mixture was allowed to stir for 15 min. After 15 min. a solution of Leu-CH$_2$Cl.HCl 12 (0.33 g, 1.66 mmol) in 10 mL of THF was added by syringe over 15 min. The resulting reaction mixture was allowed to stir for 15 h and diluted with DCM (50 mL). The resulting solution was washed with 10 mL of 1N HCl, 10 mL of 5% NaHCO$_3$, and 10 mL of 2M NaCl solution. The collected organic layer was dried over MgSO$_4$, filtered and concentrated under rotor evaporator. To the resulting residue, 50 mL hexane was added and stirred for 10 min. After stirring for 10 min, the resulting suspension was filtered and dried under vacuum for 10 min to give Boc-AAAPL-CH$_2$Cl (SEQ ID NO:7) 23 (0.63 g, 94%) as a pale yellow colored solid.

Preparation of H-AAAPL-CH$_2$Cl.HCl (SEQ ID NO:7) 24: To a stirred solution of Boc-AAAPL-CH$_2$Cl (SEQ ID NO:7) 23 (0.62 g, 1.08 mmol) in 10 mL of ethyl acetate, 10 mL of 6N HCl was added. The resulting reaction mixture was allowed to stir at room temperature for 3 h. After 3 h, the resulting mixture was washed with 50 mL DCM. The collected aqueous solution was evaporated under rotor evaporator to give H-AAAPL-CH$_2$Cl (SEQ ID NO:7) 24 (0.50 g, 91%) as an oil.

185. Preparation of MeOSuc-AAAPL-CH$_2$Cl (SEQ ID NO:7) 25: To a stirred solution of H-AAAPL-CH$_2$Cl.HCl (SEQ ID NO:7) 24 (0.50 g, 0.98 mmol) in 10 mL of THF, a suspension of sodium bicarbonate (1.0 g in 1 mL water) was added and the resulting solution was allowed to stir at room temperature for 10 min. After 10 min, methyl succinimidosuccinate 5 (0.20 g, 0.87 mmol) was added and the resulting reaction mixture was allowed to stir at room temperature for 3 h. After 3 h, the reaction mixture was diluted with DCM (50 mL). The resulting organic layer was washed with water (15 mL) and brine (15 mL). The organic layer was evaporated under rotor evaporator to give the product MeOSuc-AAAPL-CH$_2$Cl (SEQ ID NO:7) 25 (0.43 g, 84%) as a white colored solid. Data for MeOSuc-AAAPL-CH$_2$Cl (SEQ ID NO:7) 25: $^1$H NMR (CDCl$_3$, 400 MHz) δ 7.44 (d, J=7.6 Hz, 1H), 7.42 (d, J=7.2 Hz, 1H), 7.02 (d, J=8.4 Hz, 1H), 6.32 (d, J=6.0 Hz, 1H), 4.55 (m, 4H), 4.40 (d, J=16.4 Hz, 1H), 4.36 (m, 1H), 4.26 (d, J=16.4 Hz, 1H), 3.68 (m, 1H), 3.64 (s, 3H), 3.55 (m, 1H), 2.83

(m, 1H), 2.62 (m, 1H), 2.47 (m, 2H), 2.12-1.90 (m, 5H), 1.58 (m, 2H), 1.41 (d, J=6.8 Hz, 3H), 1.35 (d, J=8.0 Hz, 6H), 0.90 (d, J=6.0 Hz, 3H), 0.85 (d, J=6.4 Hz, 3H); MS (m/z): 588 [M+H]⁺.

Synthesis of MeOSuc-AlaAlaAlaProPhe-CH$_2$Cl$_{28}$ (SEQ ID NO:9):

Preparation of Boc-AAAPF-CH$_2$Cl (SEQ ID NO:9) 26: To a stirred solution of Boc-AlaAlaAlaPro-OH 19 (0.5 g, 1.17 mmol) in 10 mL of THF under argon atmosphere at +4° C., isobutyl chloroformate (0.23 mL, 1.76 mmol) and N-methylmorpholine (0.51 mL, 4.65 mmol) were added and the reaction mixture was allowed to stir for 15 min. After 15 min, a solution of Phe-CH$_2$Cl.HCl 2 (0.38 g, 1.63 mmol) in 10 mL of THF was added by syringe over 15 min. The resulting reaction mixture was allowed to stir for 15 h and diluted with DCM (50 mL). The resulting solution was washed with 10 mL of 1N HCl, 10 mL of 5% NaHCO$_3$, and 10 mL of 2M NaCl solution. The collected organic layer was dried over MgSO$_4$, filtered and concentrated under rotor evaporator. To the resulting residue, 50 mL hexane was added and stirred for 10 min. After stirring for 10 min, the resulting suspension was filtered and dried under vacuum for 10 min to give Boc-AAAPF-CH$_2$Cl (SEQ ID NO:9) 26 (0.63 g, 89%) as a pale yellow colored solid.

Preparation of H-AAAPF-CH$_2$Cl.HCl (SEQ ID NO:9) 27: To a stirred solution of Boc-AAAPF-CH$_2$Cl (SEQ ID NO:9) 26 (0.62 g, 1.02 mmol) in 10 mL of ethyl acetate, 10 mL of 6N

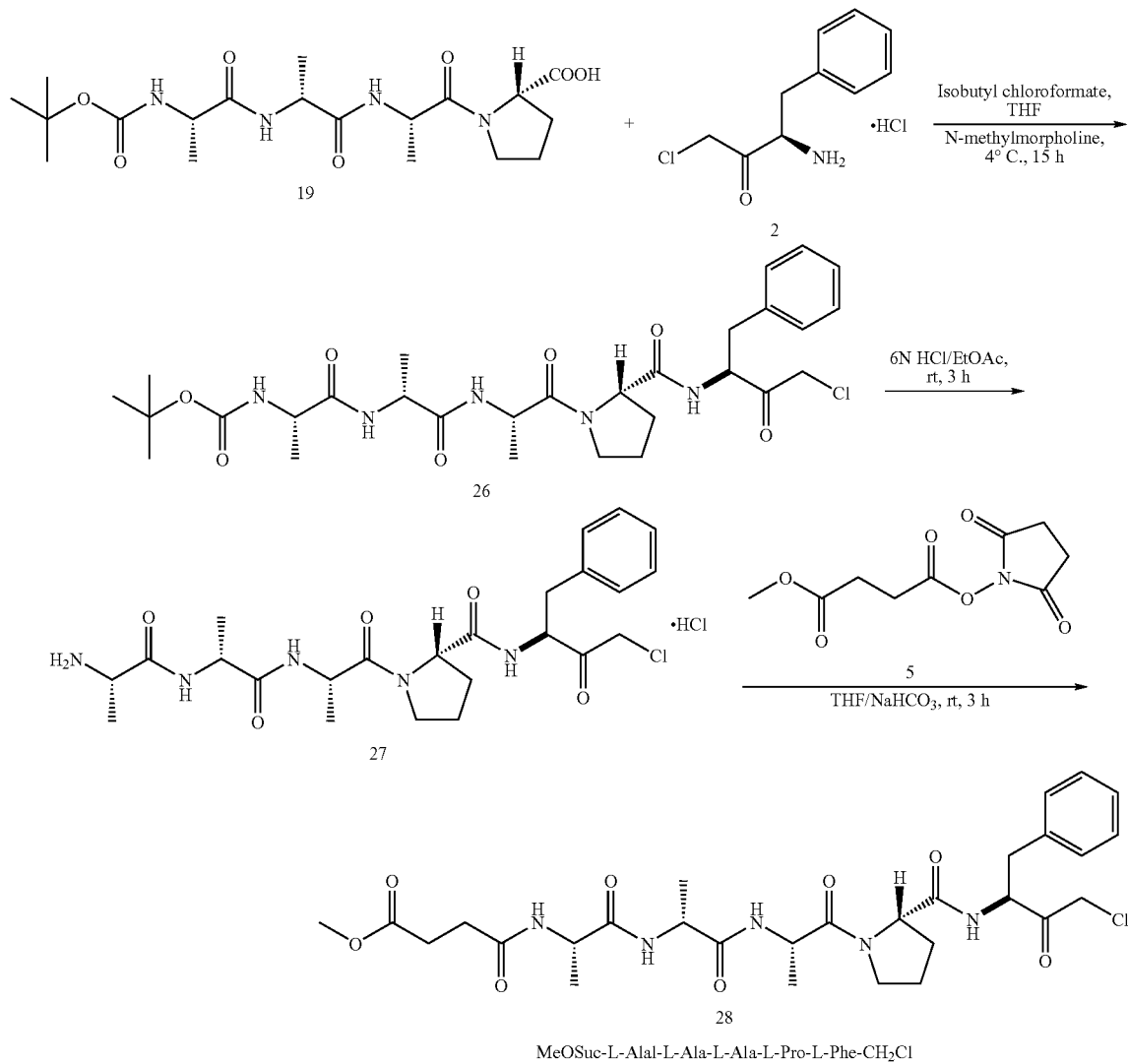

MeOSuc-L-Ala1-L-Ala-L-Ala-L-Pro-L-Phe-CH$_2$Cl

HCl was added. The resulting reaction mixture was allowed to stir at room temperature for 3 h. After 3 h, the resulting mixture was washed with 50 mL DCM. The collected aqueous solution was evaporated under rotor evaporator to give H-AAAPF-CH$_2$Cl.HCl (SEQ ID NO:9) 27 (0.51 g, 91%) as oil.

Preparation of MeOSuc-AAAPF-CH$_2$Cl (SEQ ID NO:9) 28: To a stirred solution of H-AAAPF-CH$_2$Cl.HCl (SEQ ID NO:9) 27 (0.51 g, 0.94 mmol) in 10 mL of THF, a suspension of sodium bicarbonate (1.0 g in 1 mL water) was added and the resulting solution was allowed to stir at room temperature for 10 min. After 10 min, methyl succinimidosuccinate 5 (0.19 g, 0.83 mmol) was added and the resulting reaction mixture was allowed to stir at room temperature for 3 h. After 3 h, the reaction mixture was diluted with DCM (50 mL). The resulting organic layer was washed with water (15 mL) and brine (15 mL). The organic layer was evaporated under rotor evaporator to give the product MeOSuc-AAAPF-CH$_2$Cl (SEQ ID NO:9) 28 (0.41 g, 79%) as a white colored solid. Data for MeOSuc-AAAPF-CH$_2$Cl (SEQ ID NO:9) 28: $^1$H NMR (CDCl$_3$, 400 MHz) δ 7.57 (d, J=8.0 Hz, 1H), 7.47 (d, J=5.6 Hz, 1H), 7.29-7.13 (m, 5H), 7.05 (d, J=8.4 Hz, 1H), 6.38 (d, J=6.0 Hz, 1H), 4.71 (m, 1H), 4.61 (m, 1H), 4.46 (m, 2H), 4.36 (d, J=16.8 Hz, 1H), 4.32 (m, 1H), 4.15 (d, J=16.8 Hz, 1H), 3.65 (m, 1H), 3.63 (s, 3H), 3.56 (m, 1H), 3.21 (m, 1H), 2.87 (m, 2H), 2.61 (m, 1H), 2.46 (m, 2H), 2.01-1.81 (m, 4H), 1.41 (d, J=7.2 Hz, 3H), 1.36 (d, J=7.6 Hz, 3H), 1.31 (d, J=6.8 Hz, 3H); MS (m/z): 622 [M+H]$^+$.

Example 6

Analysis of Methoxysuccinyl Pentapeptide Chloromethylketone Compounds for Proteinase K Inhibitory Activity, Indirect Linked Assay The present example provides for inhibition of proteinase K in the context of preparing samples for nucleic acid detection as for Example 2 using the test pentapeptides of Example 5.

As in Example 2, the indirect linked assay measures the amount of inhibition of proteinase K activity by assaying reverse transcriptase real time PCR amplification of a template, which amplification is dependent upon reverse transcriptase activity. The effectiveness of a test inhibitor is determined by whether proteinase K in the stopped mixture is able to digest RT, thereby rendering RT inactive for transcription.

Figure 5:
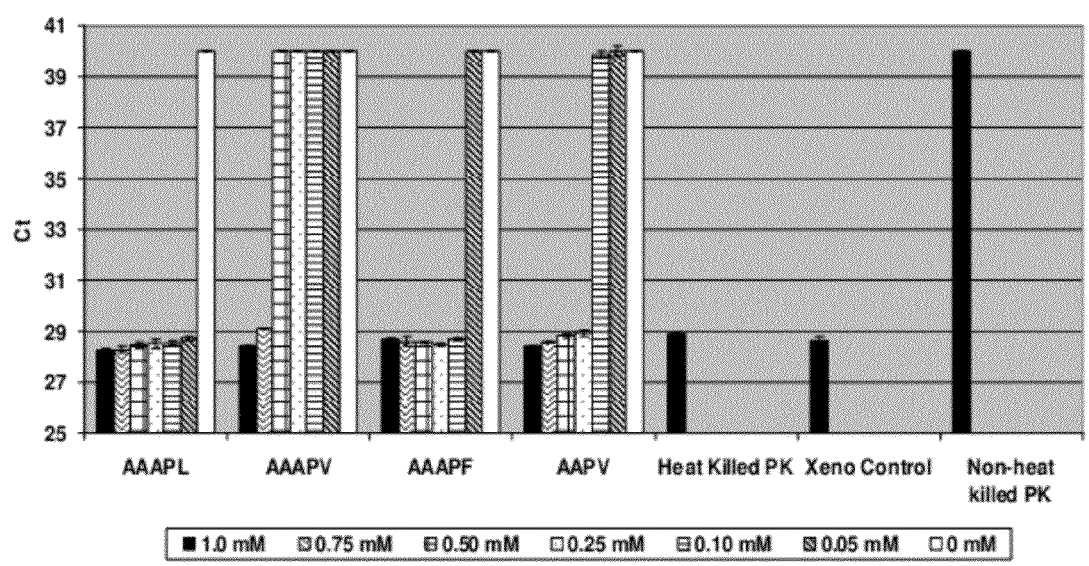

The results of assays for inhibitory activity of test methoxysuccinyl pentapeptide chloromethylketone compounds are provided by the histogram of FIG. 5 in which average Ct (cycle threshold) values are plotted against various concentrations of each compound in the stopped reactions. Results are provided for the proteinase K tetrapeptide inhibitor MeOSuc-AAPV-CH$_2$Cl (SEQ ID NO:2) (positive control), and for three test pentapeptide inhibitors MeOSuc-AAAPV-CH$_2$Cl (SEQ ID NO:8), MeOSuc-AAAPL-CH$_2$Cl (SEQ ID NO:7), and MeOSuc-AAAPF-CH$_2$Cl (SEQ ID NO:9), ranging in concentration from 1 mM to 0.05 mM in the stopped mixtures. Control reactions included 100% heat killed mixtures in which proteinase K activity is fully inactivated, MeOSuc-AAPV-CH$_2$Cl (SEQ ID NO:2) as a positive control inhibitor (AAPV (SEQ ID NO:2)), 0 mM inhibitor, control non-heat killed PK, and control Xeno™ RNA template. Ct values of ~40 represent samples with active proteinase K activity since the RT reaction is inhibited while Ct values of ~30 represent samples lacking proteinase K activity due to inhibition by the test compound. In such samples, RT generates template for amplification.

The positive control inhibitor, MeOSuc-AAPV-CH$_2$Cl (SEQ ID NO:2), is inhibitory for proteinase K activity at concentrations as low as about 0.25 mM concentration (FIG. 5) as shown by the Ct values that increase from about 29 at 0.25 mM to about 40 at 0.1 mM.

194. Interestingly, a comparison of the inhibitory activity of MeOSuc-AAAPV-CH$_2$Cl (SEQ ID NO:8) with that of MeOSuc-AAPV-CH$_2$Cl (SEQ ID NO:2) (FIG. 5) demonstrates that adding an N-terminal alanine is detrimental to inhibition of PK since a concentration of 0.75 mM MeOSuc-AAAPV-CH$_2$Cl (SEQ ID NO:8) is required to achieve the same level of inhibition demonstrated by MeOSuc-AAPV-CH$_2$Cl (SEQ ID NO:2) at 0.25 mM.

Similarly, a comparison of the inhibitory activity of MeOSuc-AAAPF-CH$_2$Cl (SEQ ID NO:9) (FIG. 5) to that of MeOSuc-AAPF-CH$_2$Cl (SEQ ID NO:5) (FIG. 1) demonstrates that adding an N-terminal alanine is detrimental to inhibition of PK since a concentration of 0.1 mM MeOSuc-AAAPF-CH$_2$Cl (SEQ ID NO:9) is required to achieve the same level of inhibition of MeOSuc-AAPF-CH$_2$Cl (SEQ ID NO:5) at 0.05 mM.

In light of these results, it was unexpected that the pentapeptide MeOSuc-AAAPL-CH$_2$Cl (SEQ ID NO:7) (FIG. 5) provides for inhibition of proteinase K activity at concentrations as low as about 0.05 mM, equal to that of the tetrapeptide MeOSuc-AAPF-CH$_2$Cl (SEQ ID NO:5) described in Example 2 and FIG. 1.

Example 7

Detection of β-Actin RNA in HeLa Cells Provides in vitro Validation

The present example provides for in vitro validation of the sample preparation and detection methods provided herein.

HeLa cells (~10,000 cells) were lysed in 500 lysis solution for 5 minutes at room temperature. Stop solution (5 μl) was then added; the lysate-stop solution was mixed, and incubated for 2 minutes at room temperature. A volume of 10 μl of stopped lysate was added to a 50 μl RT reaction followed by addition of 4 μl of RT reaction into a 200 μl PCR reaction using the β-actin primers/probe of the TaqMan® Gene Expression Cells-to-CT™ Kit (Applied Biosystems).

Figure 6:
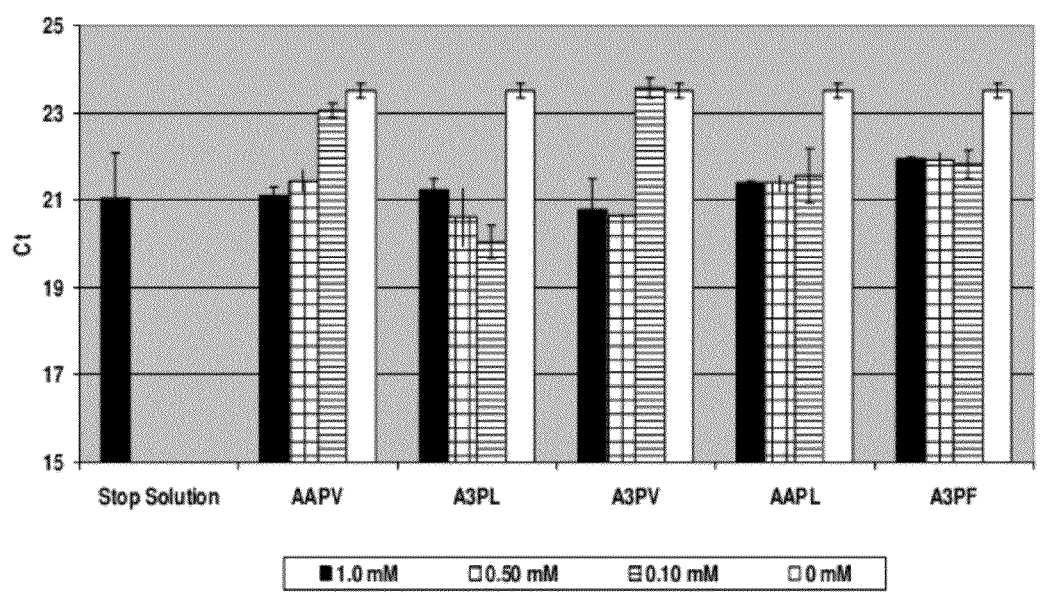

FIG. 6 provides data showing the detection of β-actin in HeLa cell cultures. The control inhibitor MeOSuc-AAPV-CH$_2$Cl (SEQ ID NO:2) effectively inhibits proteinase K at a concentration of 0.5 mM. Similarly, MeOSuc-AAAPV-CH$_2$Cl (SEQ ID NO:8) provides inhibition of proteinase K at a concentration of 0.5 mM. The peptide compounds MeOSuc-AAAPL-CH$_2$Cl (SEQ ID NO:7), MeOSuc-AAAPF-CH$_2$Cl (SEQ ID NO:9), and MeOSuc-AAPL-CH$_2$Cl (SEQ ID NO:10) appear to provide effective inhibition of proteinase K at about 0.1 mM.

Example 8

Analysis of MeOSuc-AAAPL-CH$_2$Cl (SEQ ID NO:7) for Proteinase K Inhibitory Activity, Direct Assay A direct assay for inhibition of proteinase K activity by MeOSuc-AAAPL-CH$_2$Cl (SEQ ID NO:7) was carried out using bovine serum albumin (BSA) as substrate and analyzing products using precast protein gels. Such direct assays were carried out to separate inhibition of proteinase K by a test inhibitor from any effects the stopped mixture may have on an RT-PCR reaction.

Proteinase K (50 μl of 100 μg/ml) lysis mixture without DNase (as for Example 2) was mixed with 5 μl of stop solution with varying amounts of MeOSuc-AAAPL-CH$_2$Cl (SEQ ID NO:7) and incubated for 10 min at room temperature. Ultrapure BSA (10 μl of 5 mg/ml, Applied Biosystems) was added to each sample and the samples were held for 10 min at room temperature. The reaction mixture was heated for 30 min at 95° C. and analyzed using precast protein gels (BIO-RAD, Hercules, Calif.). From the 65 μl of total reaction mixture, 10 μl reaction mixture was mixed with 5 μl of gel loading dye and further heated at 95° C. for 5 min. Then, the reactions were kept on ice for 2 min and loaded on the gel. Control reactions, with and without BSA, were also carried out.

The precast protein gel was run at 120 V for 1 h using 1× Tris/glycine/SDS buffer (BIO-RAD, Hercules, Calif.). The gel was stained with Coomassie blue stain for 1 h at room temp and destained with destaining solution (20% acetic acid, 10% methanol in 1 L). The gel was analyzed using AlphaEase™ FC software (Alpha Innotech, San Leandro, Calif.).

Figure 7:
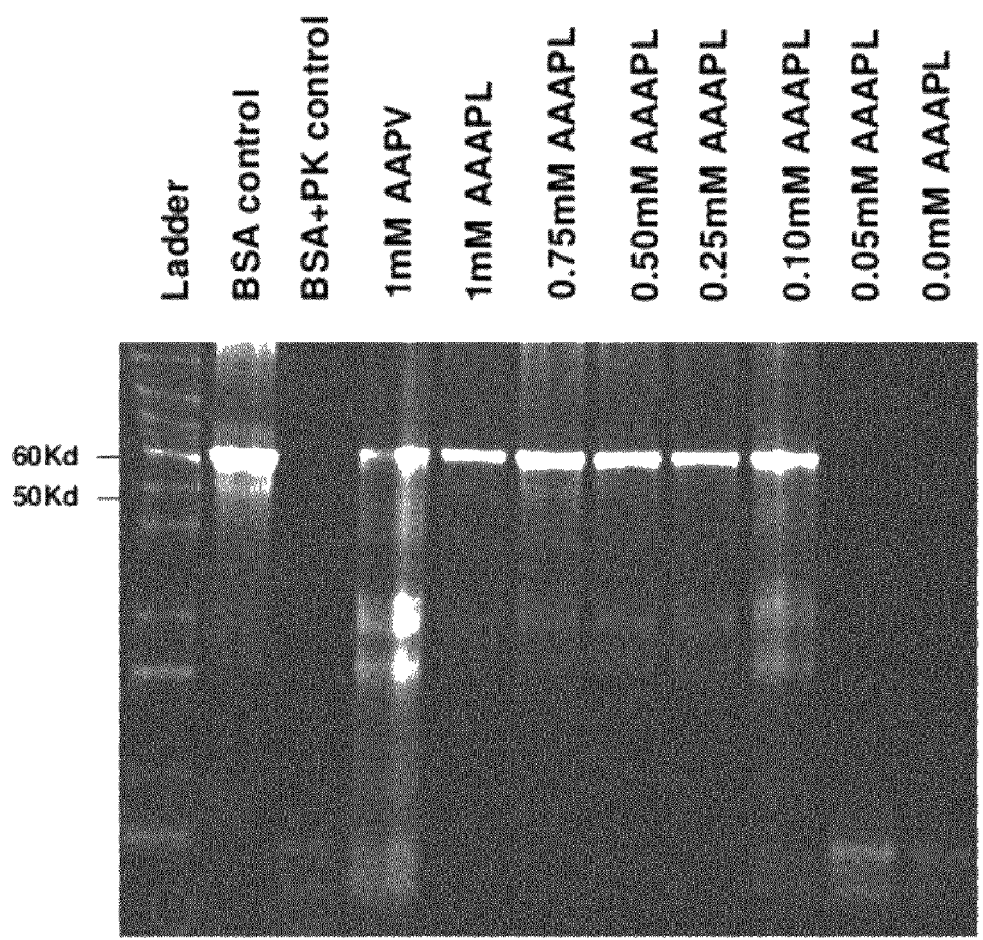

The protein gel data are summarized in FIG. 7, in which the protein marker ladder ranges in size from 10 kDa to 260 kDa (Novex® Sharp Pre-Stained Protein Standard (Invitrogen, Carlsbad Calif.)). Intact Ultrapure BSA is at about 70 Kd, and proteinase K is at about 35 kDa. The lanes of FIG. 7 are labeled as follows: Ladder, BSA control, BSA+proteinase K control, 1 mM MeOSuc-AAPV-$CH_2Cl$ (SEQ ID NO:2) as a positive control, MeOSuc-AAAPL-$CH_2Cl$ (SEQ ID NO:7) at 1 mM, 0.75 mM, 0.5 mM, 0.25 mM, 0.10 mM, 0.05 mM, and 0.0 mM. The MeOSuc-AAAPL-$CH_2Cl$ (SEQ ID NO:7) compound was capable of inhibiting proteinase K at concentrations of 0.1 mM as evidenced by the presence of BSA in the gel lane labeled as 0.10 mM AAAPL (SEQ ID NO:7).

These data demonstrate that the results of the indirect linked assay of Example 6 are due to inhibition of the proteinase K by the test inhibitors and are not due to an inhibition of the RT-PCR reaction.

Example 9

Figure 8A:
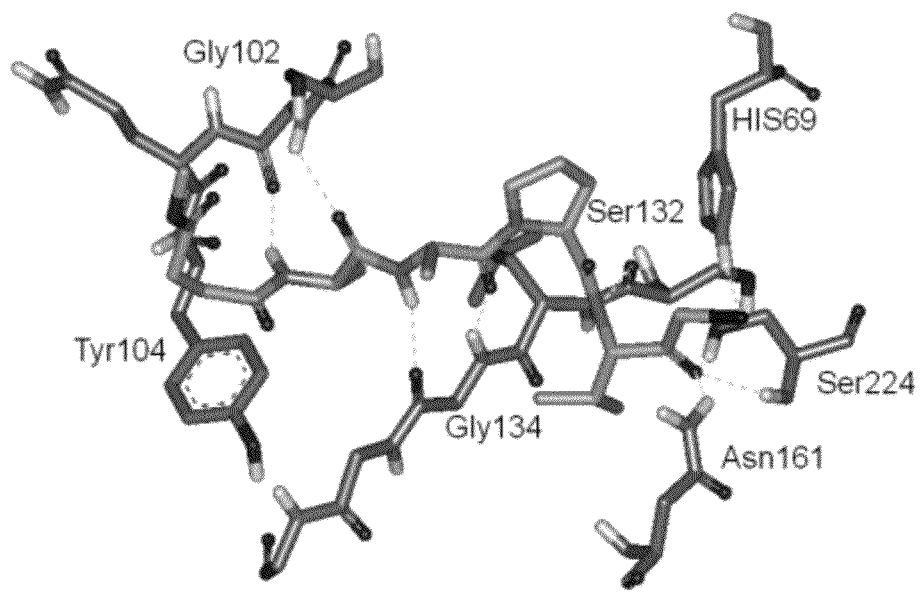
FIG. 8A and FIG. 8B show molecular modeling of proteinase K inhibitor complexes with MeOSuc-AAPV-CH$_2$Cl (SEQ ID NO:2) and MeOSuc-AAAPV-CH$_2$Cl (SEQ ID NO:8), respectively. Total binding free energy of binding inhibitor to proteinase K was calculated as in Example 9.
Figure 8B:
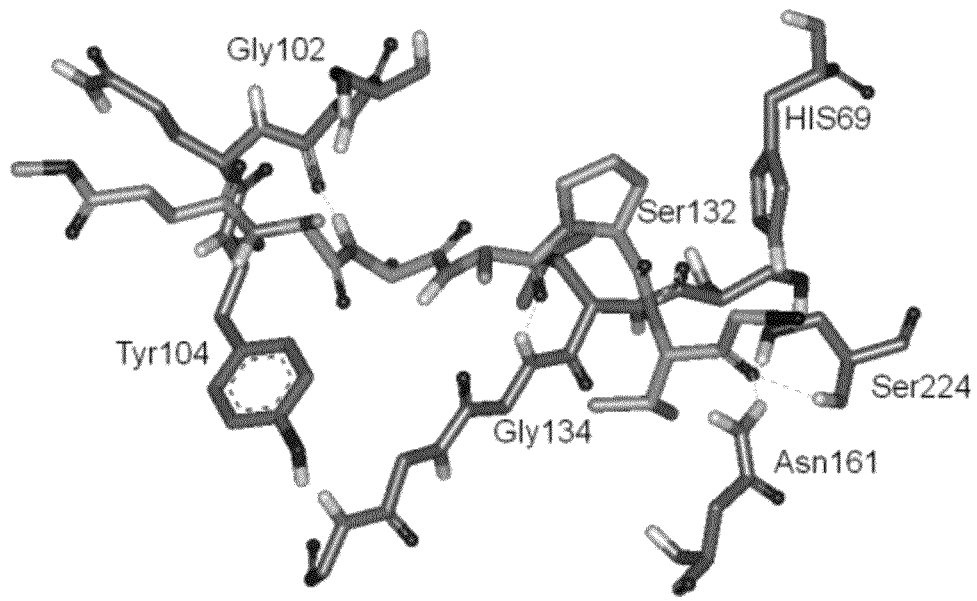
Figure 9A:
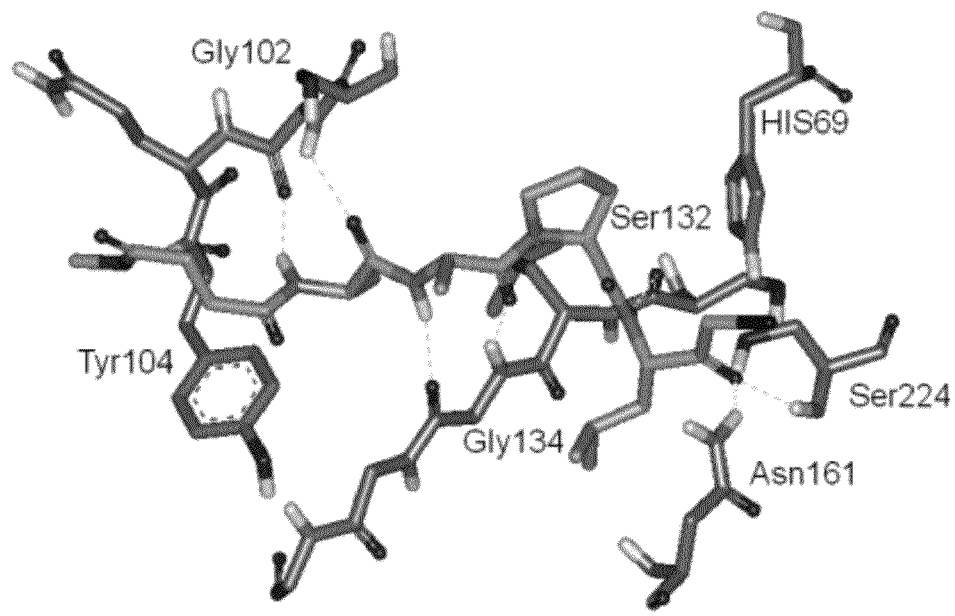
FIG. 9A and FIG. 9B show molecular modeling of proteinase K inhibitor complexes with MeOSuc-AAPL-CH$_2$Cl (SEQ ID NO:10) and MeOSuc-AAAPL-CH$_2$Cl (SEQ ID NO:7), respectively. Total binding free energy of binding inhibitor to proteinase K was calculated as in Example 9.
Figure 9B:
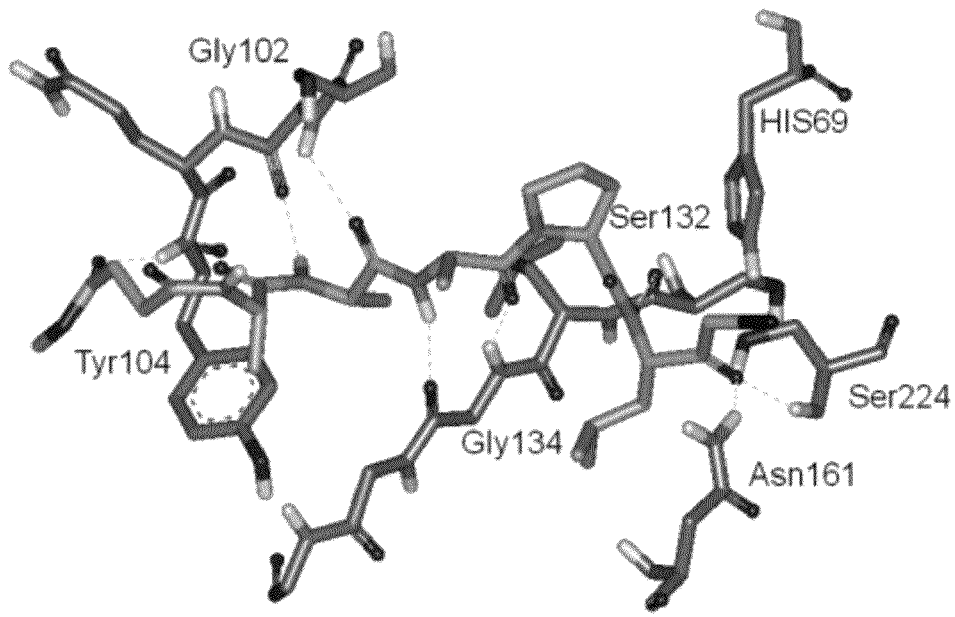
Figure 10:
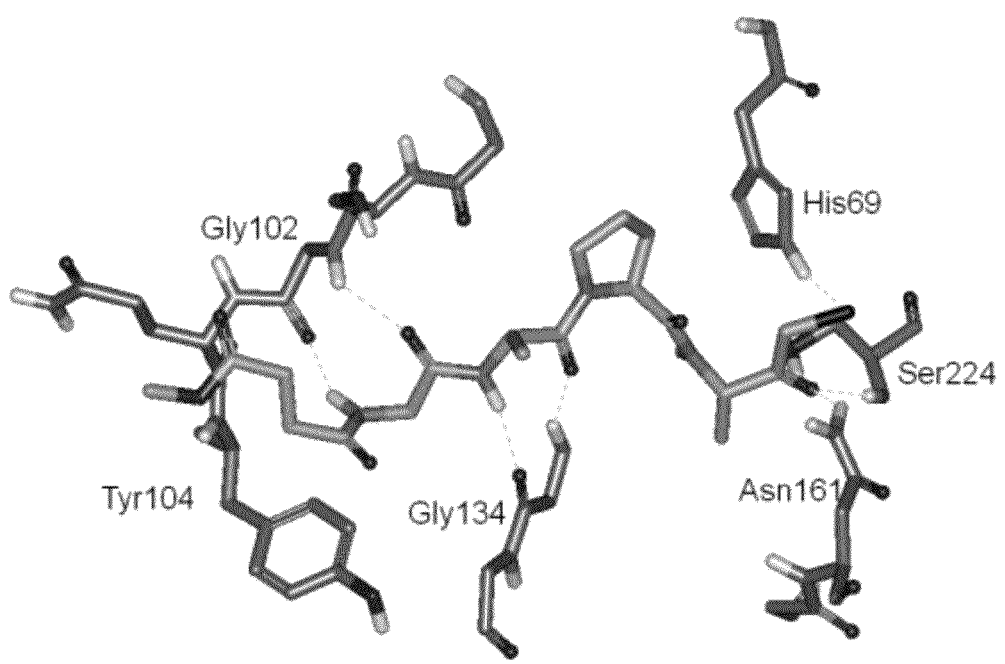
FIG. 10 shows molecular modeling of proteinase K inhibitor complexes with MeOSuc-AAPA-CH$_2$Cl (SEQ ID NO:1). Total binding free energy of binding inhibitor to proteinase K was calculated as in Example 9.
Figure 11A:
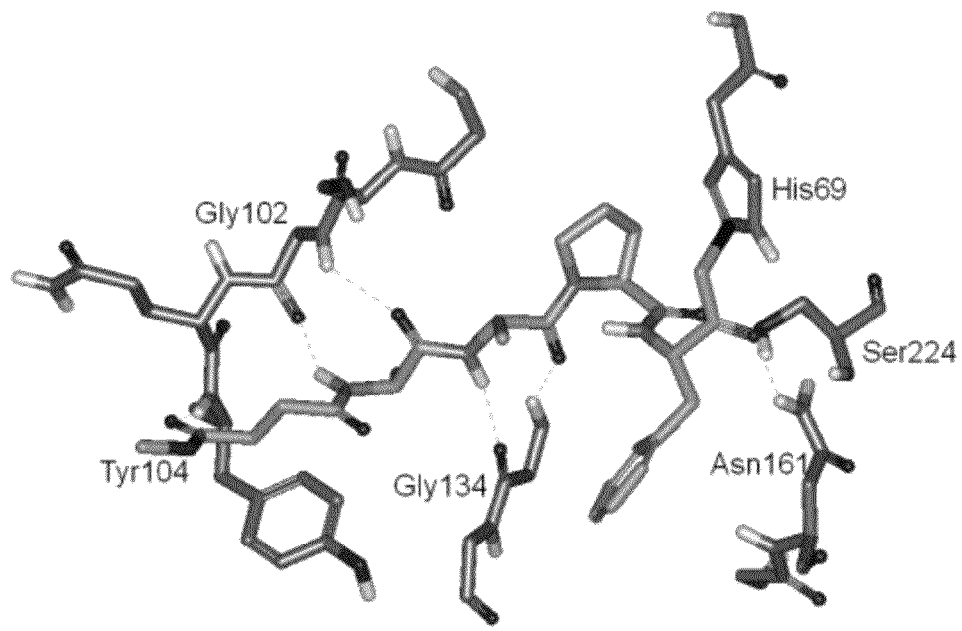
FIG. 11A and FIG. 11B show molecular modeling of proteinase K inhibitor complexes with MeOSuc-AAPF-CH$_2$Cl (SEQ ID NO:5) and MeOSuc-AAAPF-CH$_2$Cl (SEQ ID NO:9), respectively. Total binding free energy of binding inhibitor to proteinase K was calculated as in Example 9.
Figure 11B:
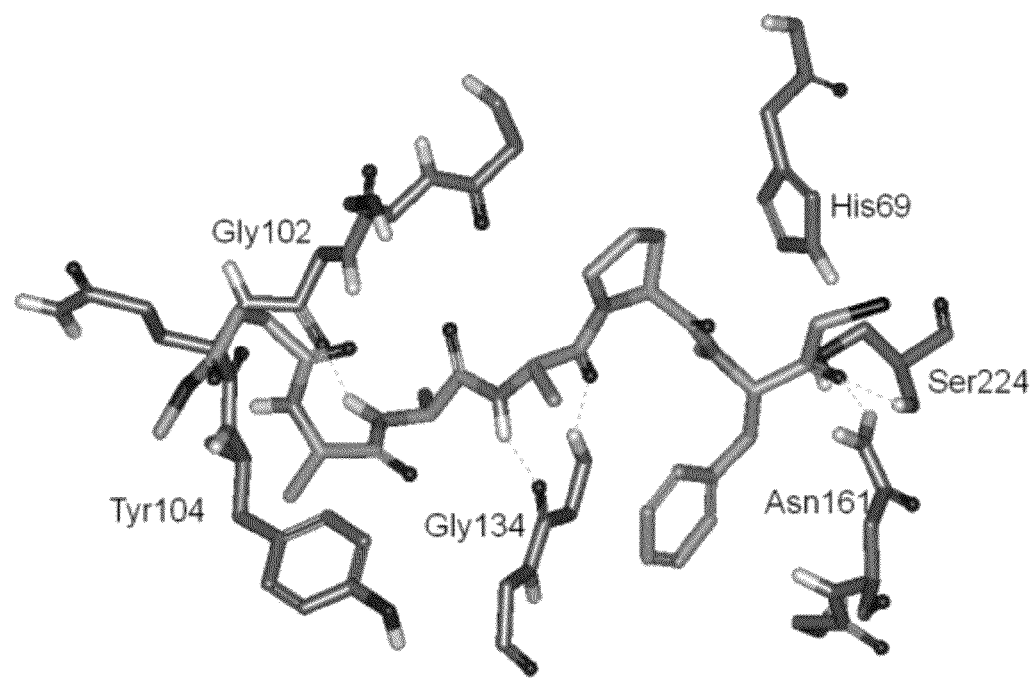

Analysis of Change in Total Binding Free Energy of Inhibitor to Proteinase K Based on Molecular Modeling Based on the studies cited in the previous examples, a study was carried out to examine the change in total binding free energy of peptide inhibitor to proteinase K to form the peptide-inhibitor complex. The molecular docking of inhibitors MeOSuc-AAPV-$CH_2Cl$ (SEQ ID NO:2), MeOSuc-AAPL-$CH_2Cl$ (SEQ ID NO:10), MeOSuc-AAAPV-$CH_2Cl$ (SEQ ID NO:8), MeOSuc-AAAPL-$CH_2Cl$ (SEQ ID NO:7), MeOSuc-AAAPF-$CH_2Cl$ (SEQ ID NO:9), MeOSuc-AAPA-$CH_2Cl$ (SEQ ID NO:1), and MeOSuc-AAPF-$CH_2Cl$ (SEQ ID NO:5) into the binding site of Proteinase K was performed using CDOCKER of Discovery Studio V2.01 (1. (Accelrys Software Inc., *Discovery Studio Modeling Environment, Release 2.01*, San Diego: Accelrys Software Inc., 2008., trial version) which uses a CHARMm based Molecular Dynamics docking algorithm. The crystal structure of the protein complex covalently formed between proteinase K and MeOSuc-AAPA-$CH_2Cl$ (SEQ ID NO:1) was used as a starting structure for molecular simulation (PDB CODE: 3PRK; Wolf W M et al. *J. Biol. Chem.* 1991, 266, 17695). Water molecules were removed from the protein complex, protonated at pH 8.0 and the structure was energy minimized using CHARMm force field with a convergence threshold of 0.05 kcal/mol A. Then, the inhibitor part was removed from the protein complex and was used to build the structures of MeOSuc-AAPV-$CH_2Cl$ (SEQ ID NO:2) (see FIG. 8A), MeOSuc-AAPL-$CH_2Cl$ (SEQ ID NO:10) (see FIG. 9A), MeOSuc-AAAPV-$CH_2Cl$ (SEQ ID NO:8) (see FIG. 8B), MeOSuc-AAAPL-$CH_2Cl$ (SEQ ID NO:7) (see FIG. 9B), MeOSuc-AAAPF-$CH_2Cl$ (SEQ ID NO:9) (see FIG. 11B), MeOSuc-AAPA-$CH_2Cl$ (SEQ ID NO:1) (see FIG. 10), and MeOSuc-AAPF-$CH_2Cl$ (SEQ ID NO:5) (see FIG. 11A). A site sphere with a radius of 13 Å was created at center of the active site of inhibitor-free proteinase K.

The CDOCKER algorithm can generate several different orientations for each inhibitor in the active site of proteinase K within the site sphere and perform MD-based simulated annealing followed by final minimization. Only 20 different poses were generated for the present study as more number of simulations were shown to display only little improvement and needs extensive computational resources. The MD simulation for each orientation consisted of 1000 steps at 2 fs per step and at 1000 K. No inherent restrictions were placed on the conformers of inhibitors. To avoid potential high energy clashes between them and the protein, each conformer was core-constrained docked and minimized using steepest-descent in Proteinase K binding site after imposing softened van der Waals and repulsive/attractive electrostatic terms within the defined grid which should facilitate greater conformational sampling. In the final simulated annealing orientation refinement stage, the grid was removed, and a full molecular mechanics force field minimization was performed for each generated conformation. The top 3 docked poses that have less inter-atomic distance (generally less than 3.5 A) between the chloromethyl carbon of the inhibitor and $His^{69}$ ($N_\epsilon$) of proteinase K were selected for further analysis. It is to be noted that the interaction pattern of these inhibitors were similar to the one that is observed with the original proteinase K-MeOSuc-AAPA-chloromethyl ketone (SEQ ID NO:1) inhibitor structure (PDB: 3PRK). In general, formation of bifurcated hydrogen bonds between Ser224 and Asn161 of proteinase K with the carbonyl of the most C-terminal amino acid residue of the inhibitor was observed in all the complexes which is similar to the one observed in the original structure (that of MeOSuc-AAPA-$CH_2Cl$ (SEQ ID NO:1) (see FIG. 10)). Other common hydrogen bonding interactions of Ser132, Gly134 and Gly102 of proteinase K with Pro, Ala and Ala of inhibitors were also observed, respectively. A difference between the proteinase K complexes of MeOSuc-AAPV-$CH_2Cl$ (SEQ ID NO:2) and MeOSuc-AAAPV-$CH_2Cl$ (SEQ ID NO:8) is that the former has three additional intramolecular hydrogen bonds which can add additional stabilization to the protein inhibitor complex (compare FIG. 8A and FIG. 8B). The number of intramolecular hydrogen bonding interactions of proteinase K and the inhibitors MeOSuc-AAPL-$CH_2Cl$ (SEQ ID NO:10) and MeOSuc-AAAPL-$CH_2Cl$ (SEQ ID NO:7) were the same (compare FIG. 9A and FIG. 9B).

The selected three poses for each inhibitor were rescored using a physics-based molecular mechanics Poisson-Boltzmann surface area (MM-PBSA) implicit solvation model that ranks the docked inhibitor poses in terms of their total binding free energy. The total binding free energy was then calculated from the following equation in which $\Delta\Delta G_{Bind}$ is the change in free energy, also referred to as the total binding free energy; $\Delta G_{complex}$ is free energy of the complex; $\Delta G_{Ligand}$ is free energy of the ligand and $\Delta G_{Protein}$ is the free energy of the protein (Pearce B C et al., *J. Chem. Inf. Model.* 2009, 49, 1797).

$$\Delta\Delta G_{Bind} = \Delta G_{complex} - \Delta G_{Ligand} - \Delta G_{protein}$$

The average of the total binding free energy of the three poses for each inhibitor were then calculated and the results were tabulated in Table 2.

TABLE 2

Total Binding Free Energies of Tetra- and Penta-Peptide Inhibitors into the Binding Site of Proteinase K.

| SEQ ID NO: | Inhibitors | $\Delta G_{Ligand}$ (kcal/mol) | $\Delta G_{Protein}$ (kcal/mol) | $\Delta G_{Complex}$ (kcal/mol) | $\Delta\Delta G_{Bind}$ (kcal/mol) |
|---|---|---|---|---|---|
| 1 | MeOSuc-AAPA-CH$_2$Cl | −143.60 | −14001.10 | −14159.30 | −14.60 |
| 2 | MeOSuc-AAPV-CH$_2$Cl | −144.10 | −14001.10 | −14151.83 | −6.63 |
| 5 | MeOSuc-AAPF-CH$_2$Cl | −144.62 | −14001.10 | −14148.27 | −2.55 |
| 7 | MeOSuc-AAAPL-CH$_2$Cl | −161.41 | −14001.10 | −14193.40 | −30.89 |
| 8 | MeOSuc-AAAPV-CH$_2$Cl | −173.72 | −14001.10 | −14173.50 | 1.32 |
| 9 | MeOSuc-AAAPF-CH$_2$Cl | −177.41 | −14001.10 | −14168.57 | 9.95 |
| 10 | MeOSuc-AAPL-CH$_2$Cl | −141.04 | −14001.10 | −14154.80 | −12.66 |

The results of the comparison of the total binding free energies of MeOSuc-AAPV-CH$_2$Cl (SEQ ID NO:2) (−6.63 kcal/mol) and MeOSuc-AAAPV-CH$_2$Cl (SEQ ID NO:8) (+1.32 kcal/mol) to proteinase K are corroborated by the higher inhibitory efficiency of MeOSuc-AAPV-CH$_2$Cl (SEQ ID NO:2) demonstrated experimentally (see the data of FIG. 5). As observed above from the molecular modeling studies, the proteinase K complex of MeOSuc-AAPV-CH$_2$Cl (SEQ ID NO:2) has three additional intramolecular hydrogen bonds as compared to the proteinase K complex with MeOSuc-AAAPV-CH$_2$Cl (SEQ ID NO:8).

Both the MeOSuc-AAAPL-CH$_2$Cl-proteinase K complex (SEQ ID NO:7) (−30.89 kcal/mol) and the MeOSuc-AAPL-CH$_2$Cl-proteinase K complex (SEQ ID NO:10) (−12.66 kcal/mol) demonstrate lower total binding free energy to proteinase K than does MeOSuc-AAPV-CH$_2$Cl (SEQ ID NO:2) (−6.63 kcal/mol). These data are supported again by the experimental data of FIG. 5 (compare the data for methoxysuccinyl-AAAPL-chloromethyl ketone (SEQ ID NO:7) with the data for methoxysuccinyl-AAPV-chloromethyl ketone (SEQ ID NO:2) data) and FIG. 6 (compare the data for methoxysuccinyl-AAAPL-chloromethyl ketone (SEQ ID NO:7) data or the data for methoxysuccinyl-AAPL-chloromethyl ketone (SEQ ID NO:10) with the data for methoxysuccinyl-AAPV-chloromethyl ketone (SEQ ID NO:2) data).

However, MeOSuc-AAPF-CH$_2$Cl (SEQ ID NO:5) has a total binding free energy to proteinase K of −2.55 kcal/mol which is greater than that of MeOSuc-AAPV-CH$_2$Cl to proteinase K (SEQ ID NO:2) (−6.63 kcal/mol). Nevertheless, MeOSuc-AAPF-CH$_2$Cl (SEQ ID NO:5) was demonstrated to be an effective inhibitor for proteinase K as shown by the data of FIG. 1, FIG. 2 and FIG. 3. Similarly, MeOSuc-AAAPF-CH$_2$Cl (SEQ ID NO:9) is an effective inhibitor of proteinase K as shown by the data of FIG. 5, yet the total binding free energy is +9.95. Among all seven inhibitors tested using molecular modeling, MeOSuc-AAAPL-CH$_2$Cl binding to proteinase K (SEQ ID NO:7) exhibited the lowest total binding free energy with good inhibitory efficiency against proteinase K.

The compositions, methods, and kits of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

Although the disclosed teachings have been described with reference to various applications, methods, and compositions, it will be appreciated that various changes and modifications can be made without departing from the teachings herein. The foregoing examples are provided to better illustrate the present teachings and are not intended to limit the scope of the teachings herein. Certain aspects of the present teachings can be further understood in light of the following claims.

What is claimed is:

1. A process for preparing a sample containing RNA for in situ analysis of RNA or a surrogate thereof, the process comprising:
   contacting the sample containing RNA with a lysis mixture under conditions and for a time to produce a lysate, wherein the lysis mixture comprises:
      proteinase K or an enzymatically active mutant or variant thereof,
      a polypeptide having deoxyribonuclease activity, and
      a surfactant that substantially lacks fluorescence between 300 nm and 750 nm when in use for in situ analysis of RNA or a surrogate thereof,
      wherein the lysis mixture is substantially free of a cation chelator;
   and
   admixing the lysate with a stop mixture at substantially the same temperature as the contacting step to form a stopped mixture, wherein the stop mixture comprises:
      a cation chelator effective to inactivate the polypeptide having deoxyribonuclease activity, and
      at least one alkoxysuccinyl-peptidyl-haloalkyl ketone wherein the peptidyl portion of the ketone comprises SEQ ID NO:5;
      wherein the halo of haloalkyl is mono- or di-chloro, bromo, or iodo and the alkyl of haloalkyl or alkoxy is $C_1$-$C_3$ alkyl, and
   wherein the stopped mixture is thereby prepared for in situ analysis of RNA or a surrogate thereof.

2. The process of claim 1 further comprising contacting the stopped mixture with reagents for reverse transcription to form a first amplification mixture.

3. The process of claim 2 further comprising contacting the first amplification mixture with reagents for q-PCR amplification.

4. The process of claim 1 wherein the contacting and admixing are carried out at 16° C. to 28° C.

5. The process of claim 1 wherein the sample comprises a cell or cell culture.

6. The process of claim 1 wherein the sample comprises a tissue sample or a sample comprising a virus.

7. The process of claim 1 wherein the polypeptide having deoxyribonuclease activity is stabilized by calcium cations and the lysis mixture further comprises a calcium salt.

8. The process of claim 1 wherein the surfactant comprises TRITON X-114™.

9. The process of claim 1 wherein the peptidyl portion of the at least one alkoxysuccinyl-peptidyl-haloalkyl ketone is a tetrapeptide or a pentapeptide.

10. The process of claim 1 wherein the alkoxysuccinyl-peptidyl-haloalkyl ketone is methoxysuccinyl-AAPF-chloromethyl ketone (SEQ ID NO:5).

11. A process for preparing a sample containing RNA for in situ analysis of RNA, the process comprising:
   contacting the sample containing RNA with a lysis mixture comprising proteinase K under conditions and for a time to produce a lysate,
   and
   admixing the lysate with a stop mixture at substantially the same temperature as the contacting step to form a stopped mixture, wherein the stop mixture comprises:
      at least one alkoxysuccinyl-peptidyl-haloalkyl ketone wherein the peptidyl portion of the ketone comprises SEQ ID NO:5; and wherein the halo of haloalkyl is mono- or di-chloro, bromo, or iodo and the alkyl of haloalkyl or alkoxy is $C_1$-$C_3$ alkyl.

12. The process of claim 11 further comprising contacting the stopped mixture with reagents for reverse transcription to form a first amplification mixture.

13. The process of claim 11 further comprising contacting the first amplification mixture with reagents for q-PCR amplification.

* * * * *